(12) United States Patent
Claremon et al.

(10) Patent No.: US 9,163,012 B2
(45) Date of Patent: Oct. 20, 2015

(54) CARBAMATE AND UREA INHIBITORS OF 11β-HYDROXYSTEROID DEHYDROGENASE 1

(75) Inventors: David A. Claremon, Maple Glen, PA (US); Colin M. Tice, Ambler, PA (US); Linghang Zhuang, Chalfont, PA (US); Katerina Leftheris, Skillman, NJ (US); Yuanjie Ye, Ambler, PA (US); Suresh B. Singh, Kendall Park, NJ (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 563 days.

(21) Appl. No.: 12/791,592

(22) Filed: Jun. 1, 2010

(65) Prior Publication Data

US 2011/0053943 A1    Mar. 3, 2011

Related U.S. Application Data

(60) Provisional application No. 61/217,593, filed on Jun. 2, 2009, provisional application No. 61/269,406, filed on Jun. 24, 2009.

(51) Int. Cl.

| | |
|---|---|
| *A61K 31/40* | (2006.01) |
| *A61K 31/50* | (2006.01) |
| *A61K 31/495* | (2006.01) |
| *C07D 239/42* | (2006.01) |
| *A61K 31/47* | (2006.01) |
| *A61K 31/445* | (2006.01) |
| *A61K 31/44* | (2006.01) |
| *A61K 31/41* | (2006.01) |
| *C07D 417/04* | (2006.01) |
| *C07D 207/16* | (2006.01) |
| *C07D 211/22* | (2006.01) |
| *C07D 211/34* | (2006.01) |
| *C07D 211/60* | (2006.01) |
| *C07D 401/12* | (2006.01) |
| *C07D 403/12* | (2006.01) |
| *C07D 413/04* | (2006.01) |
| *C07D 417/12* | (2006.01) |
| *C07D 471/04* | (2006.01) |

(52) U.S. Cl.
CPC ............ *C07D 417/04* (2013.01); *C07D 207/16* (2013.01); *C07D 211/22* (2013.01); *C07D 211/34* (2013.01); *C07D 211/60* (2013.01); *C07D 401/12* (2013.01); *C07D 403/12* (2013.01); *C07D 413/04* (2013.01); *C07D 417/12* (2013.01); *C07D 471/04* (2013.01)

(58) Field of Classification Search
None
See application file for complete search history.

(56) References Cited

U.S. PATENT DOCUMENTS

2004/0229902 A1 * 11/2004 Josien .......................... 514/304

FOREIGN PATENT DOCUMENTS

| JP | 2006-511554 A | 4/2006 | | |
|---|---|---|---|---|
| JP | 2007-501859 A | 2/2007 | | |
| JP | 2011-518218 A | 6/2011 | | |
| WO | WO-2004/020140 | 3/2004 | | |
| WO | 2008/024497 A2 | 2/2008 | | |
| WO | WO-2008/024497 | 2/2008 | | |
| WO | 2008/083238 A2 | 7/2008 | | |
| WO | 2009/001817 A1 | 12/2008 | | |
| WO | 2009/020140 A1 | 2/2009 | | |
| WO | 2009/052319 A1 | 4/2009 | | |
| WO | WO 2009/052319 | * 4/2009 | ............ | C07C 231/00 |
| WO | WO-2009/131669 | 10/2009 | | |
| WO | WO-2010/141424 | 12/2010 | | |

OTHER PUBLICATIONS

CAS RN 796042-91-6 (entered into STN Dec. 10, 2004).*
International Search Report and Written Opinion for PCT/US2010/036832, mailed Aug. 10, 2010.
T.J. Donohoe et al., "Stereoselectivity in the double reductive alkylation of pyrroles: synthesis of cis-3,4-disubstituted pyrrolidines" *Chemical Communications*, 1999(2), pp. 141-142 (1999).
Fincham, Christopher, I., et al., "The Use of a Proline Ring as a Conformational Restraint in CCK-B Receptor 'Dipeptoids,'" Bioorganic & Medicinal Chemistry Letters, vol. 2, No. 5, pp. 403-406, 1992.
Donohoe, Timothy, J., et al., "Stereoselectivity in the Double Reductive Alkylation of Pyrroles: Synthesis of cis-3,4-disubstituted Pyrrolidines," Chem. Commun., 1999, pp. 141-142.

* cited by examiner

*Primary Examiner* — Craig Ricci
(74) *Attorney, Agent, or Firm* — McCarter & English LLP; Steven G. Davis; Michael J. DeGrazia

(57) ABSTRACT

This invention relates to novel compounds of the invention pharmaceutically acceptable salts thereof, and pharmaceutical compositions thereof, which are useful for the therapeutic treatment of diseases associated with the modulation or inhibition of 11β-HSD1 in mammals. The invention further relates to pharmaceutical compositions of the novel compounds and methods for their use in the reduction or control of the production of cortisol in a cell or the inhibition of the conversion of cortisone to cortisol in a cell.

27 Claims, No Drawings

CARBAMATE AND UREA INHIBITORS OF 11β-HYDROXYSTEROID DEHYDROGENASE 1

RELATED APPLICATIONS

This application claims the benefit of U.S. Provisional Application No. 61/217,593, filed Jun. 2, 2009, and U.S. Provisional Application No. 61/269,406, filed Jun. 24, 2009. The entire teachings of these two applications are incorporated herein by reference.

FIELD OF THE INVENTION

The present invention relates to inhibitors of 11β-hydroxysteroid dehydrogenase type 1 (11β-HSD1), pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-

14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Ophthalmol. Vis. Sci. 41: 1629-1683; Rauz et al. (2001) Invest. Ophthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metab. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043,951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula I or pharmaceutically acceptable salts thereof are effective inhibitors of 11β-HSD1. Formula I and its constituent members are defined herein as follows:

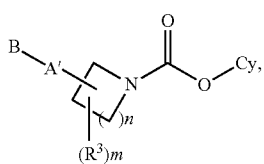

wherein
Cy is $(C_7-C_{12})$bicycloalkyl or $(C_9-C_{12})$tricycloalkyl, in which 1-2 carbon atoms are optionally replaced with a heteroatom independently selected from N and O, and which is optionally substituted with 1-3 groups independently selected from halogen, nitro, cyano, $(C_1-C_3)$ alkyl, halo$(C_1-C_3)$alkyl, hydroxy$(C_1-C_3)$alkyl, $OR^4$, halo$(C_1-C_3)$alkoxy, $N(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl, optionally substituted heteroaryl, optionally substituted heterocyclyl and optionally substituted cycloalkyl, wherein the aryl, heteroaryl, heterocyclyl and cycloalkyl are optionally substituted with one to three groups represented by $R^7$;

B is aryl, heterocyclyl or heteroaryl, each optionally substituted with 1-4 groups represented by $R^6$;

$R^3$ is $(C_1-C_8)$alkyl, $(C_2-C_8)$alkenyl, $(C_2-C_8)$alkynyl, cycloalkyl$(C_0-C_3)$alkyl, heterocyclyl$(C_0-C_3)$alkyl, aryl$(C_0-C_3)$alkyl, heteroaryl$(C_0-C_3)$alkyl or $(CH_2)_xCO_2R^4$, each optionally substituted by 1-4 groups independently selected from halogen, nitro, cyano, $(C_1-C_3)$alkyl, halo$(C_1-C_3)$alkyl, halo$(C_1-C_3)$alkoxy, hydroxy$(C_1-C_3)$ alkyl, $OR^4$, $N(R^4)_2$, $(CH_2)_xC(=NOH)NH_2$, $(CH_2)_x NR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, $(CH_2)_xOR^4$, $(CH_2)_xO(CH_2)_xCO_2R^4$, optionally substituted aryl, optionally substituted heteroaryl, optionally substituted heterocyclyl and optionally substituted cycloalkyl, wherein aryl, heteroaryl, heterocyclyl and cycloalkyl are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, cycloalkyl$(C_0-C_3)$ alkyl, heterocyclyl$(C_0-C_3)$alkyl, alkyl portion of aryl $(C_0-C_3)$alkyl and heteroaryl$(C_0-C_3)$alkyl are further optionally substituted with oxo;

each $R^4$ is independently (a) hydrogen; or (b) $(C_1-C_{10})$ alkyl, aryl$(C_0-C_3)$alkyl, each optionally substituted with 1-4 groups selected from halogen, $(C_1-C_3)$alkoxy, $(C_1-C_3)$alkyl, halo$(C_1-C_3)$alkyl, halo$(C_1-C_3)$alkoxy, cyano and nitro;

$R^5$ is hydrogen or $(C_1-C_6)$alkyl;

each $R^6$ is independently selected from halogen, nitro, cyano, $(C_1-C_3)$alkyl, cyclo$(C_3-C_6)$alkyl, halo$(C_1-C_3)$ alkyl, hydroxy$(C_1-C_3)$alkyl, oxo, $OR^4$, halo$(C_1-C_3)$ alkoxy, $(CH_2)_xN(R^4)_2$, $(CH_2)_xC(=NOH)NH_2$, $(CH_2)_x NR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_x(OC(=O)N(R^4)_2$, $(CH_2)_xOR^4$, $(CH_2)_xO(CH_2)_xCO_2R^4$, optionally substituted aryl, optionally substituted heteroaryl, optionally substituted heterocyclyl and optionally substituted cycloalkyl, wherein the aryl, heteroaryl, heterocyclyl and cycloalkyl are further optionally substituted with one to three groups represented by $R^7$;

$R^7$ is halogen, nitro, cyano, $(C_1-C_3)$alkyl, halo$(C_1-C_3)$ alkyl, cyclo$(C_3-C_6)$alkyl, $(C_1-C_3)$alkoxy, halo$(C_1-C_3)$ alkoxy, $N(R^4)_2$, or $CON(R^4)_2$, provided that $R^7$ also includes oxo when the heteroaryl, heterocyclyl and cycloalkyl are substituted with $R^7$;

x is 0, 1, 2 or 3;

A' is a bond, $CH_2$ or -AO—;

A is a bond, or $CH_2$;

m is 0, 1, 2, or 3;

n is 1, 2 or 3;

or a pharmaceutically acceptable salt thereof.

Another embodiment of the invention are compounds of Formula II and III, or a pharmaceutically acceptable salt thereof:

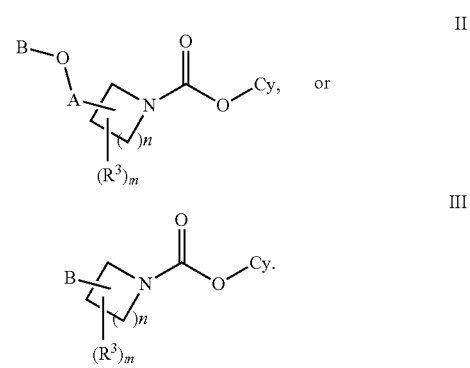

The variables in Formulas II and III are as defined for Formula I above.

Another embodiment is a pharmaceutical composition comprising: i) the compounds of the invention or a pharmaceutically acceptable salt thereof; and ii) a pharmaceutically acceptable carrier or diluent.

Another embodiment is a method of treating a subject with a disease associated with the activity or expression of 11β-HSD1, comprising the step of administering to the subject an effective amount of a compound of the invention or a pharmaceutically acceptable salt thereof.

Another embodiment of the invention is a compound of the invention or a pharmaceutically acceptable salt thereof for use in treating a subject with a disease associated with the activity or expression of 11β-HSD1.

Another embodiment of the invention is the use of a compound of the invention or a pharmaceutically acceptable salt thereof for the manufacture of a medicament for treating a subject with a disease associated with the activity or expression of 11β-HSD1.

Another embodiment of the invention is a method of inhibiting 11β-HSD1 activity comprising the step of administering to a mammal in need of such treatment an effective amount of a compound of the invention or a pharmaceutically acceptable salt thereof.

Another embodiment of the invention is the use of a compound of the invention or a pharmaceutically acceptable salt thereof for the manufacture of a medicament for inhibiting 11β-HSD1 activity in a mammal in need of such treatment.

Another embodiment of the invention is a compound of the invention or a pharmaceutically acceptable salt thereof for use in inhibiting 11β-HSD1 activity in a mammal in need of such treatment.

DETAILED DESCRIPTION OF THE INVENTION

The present invention provides novel compounds that are effective inhibitors of 11β-hydroxysteroid dehydrogenase type 1 (11β-HSD1).

Values and specific values for the variables in the above-described Structural Formulas I, II or III are provided herein:

Cy is $(C_7-C_{12})$bicycloalkyl or $(C_9-C_{12})$tricycloalkyl, in which 1-2 carbon atoms are optionally replaced with heteroatoms independently selected from N and O. The group represented by Cy is optionally substituted with 1-3 groups independently selected from halogen, nitro, cyano, $(C_1-C_3)$alkyl, halo$(C_1-C_3)$alkyl, hydroxy$(C_1-C_3)$alkyl, $OR^4$, halo$(C_1-C_3)$alkoxy, $N(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$. The groups represented by $Ar_1$, $HetAr_1$, $HetCy_1$ and $Cy_1$ are optionally substituted with one to three groups represented by $R^7$. In a specific embodiment, Cy is $(C_7-C_{12})$bicycloalkyl or $(C_9-C_{12})$tricycloalkyl. The group represented by Cy is optionally substituted with 1-3 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$. In a specific embodiment, Cy is adamantyl. In another specific embodiment Cy is 2-adamantyl. Adamantyl in the group represented by Cy is optionally substituted with 1-3 groups independently selected from halogen, cyano, hydroxy, hydroxy$(C_1-C_3)$alkyl, $N(R^4)_2$, $CO_2R^4$, $CON(R^4)_2$, $CH_2CON(R^4)_2$, $SO_2N(R^4)_2$, $SO_2R^4$, $NR^4COR^4$ and $OC(=O)N(R^4)_2$.

B is aryl, heterocyclyl or heteroaryl, each optionally substituted with 1-4 groups represented by $R^6$. In a specific embodiment, B is heteroaryl, optionally substituted with 1-4 groups represented by $R^6$. In a specific embodiment B is furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, benzo[b]furyl, benzo[b]thienyl, indazolyl, benzimidazolyl, benzthiazolyl, purinyl, 4H-quinolizinyl, quinolinyl, isoquinolinyl, quinazolinyl, benzothienyl, benzofuranyl, 2,3-dihydrobenzofuranyl, benzodioxolyl, benzimidazolyl, indazolyl, benzisoxazolyl, benzoxazolyl, benzothiazolyl, cinnolinyl, phthalzinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,3,4-thiadiazolyl, 1,2,4-triazinyl, 1,3,5-triazinyl, tetrazolyl, pteridinyl, imidazopyridazinyl, triazolopyridyl imidazopyridinyl, oxodihydroimidazopyridyl, oxodihydroindolinyl substituted with 1-4 groups represented by $R^6$. In a specific embodiment, B is aryl, optionally substituted with 1-4 groups represented by $R^6$. In a specific embodiment B is

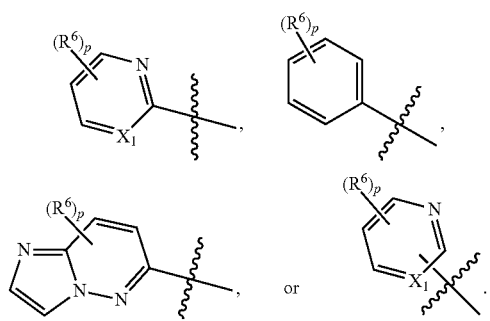

In another specific embodiment B is oxodihydroquinolinyl. In a specific embodiment B is heterocyclyl. In another specific embodiment B is oxodihydropyridyl, oxodihydropyridazinyl, oxodihydropyrimidinyl or oxodihydropyrazinyl.

$R^3$ is $(C_1-C_8)$alkyl, $(C_2-C_8)$alkenyl, $(C_2-C_8)$alkynyl, $(C_3-C_8)$cycloalkyl$(C_0-C_3)$alkyl, heterocyclyl$(C_0-C_3)$alkyl, aryl$(C_0-C_3)$alkyl, heteroaryl$(C_0-C_3)$alkyl or $(CH_2)_xCO_2R^4$. The group represented by $R^3$ is optionally substituted by 1-4 groups independently selected from halogen, nitro, cyano, $(C_1-C_3)$alkyl, halo$(C_1-C_3)$alkyl, halo$(C_1-C_3)$alkoxy, hydroxy$(C_1-C_3)$alkyl, $OR^4$, $N(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, $(CH_2)_xOR^4$, $(CH_2)_xO(CH_2)_xCO_2R^4$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$. The group represented by $Ar_1$, $HetAr_1$, $HetCy_1$ and $Cy_1$ is optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl $(C_1-C_3)$alkyl are further optionally substituted with oxo. In a specific embodiment $R^3$ is $(C_1-C_8)$alkyl, $(C_2-C_8)$alkenyl, $(C_2-C_8)$alkynyl, $(C_3-C_8)$cycloalkyl$(C_0-C_3)$alkyl, heterocyclyl$(C_0-C_3)$alkyl, aryl$(C_0-C_3)$alkyl or heteroaryl$(C_0-C_3)$alkyl. The group represented by $R^3$ is optionally substituted by 1-4 groups independently selected from halogen, nitro, cyano, $(C_1-C_3)$alkyl, halo$(C_1-C_3)$alkyl, halo$(C_1-C_3)$alkoxy, hydroxy$(C_1-C_3)$alkyl, $OR^4$, $N(R^4)_2$, $(CH_2)_xC(=NOH)NH_2$, $(CH_2)_x$ $NR^4CON(R^4)_2$, $(CH_2)_xCON(R^4)_2$, $(CH_2)_xSO_2N(R^4)_2$, $(CH_2)_x$ $SO_2R^4$, $(CH_2)_xNR^4COR^4$, $(CH_2)_xNR^4CO_2R^4$, $(CH_2)_x$ $NR^4SO_2R^4$, $(CH_2)_xOC(=O)N(R^4)_2$, $(CH_2)_xOR^4$, $(CH_2)_xO(CH_2)_xCO_2R^4$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$. The group represented by $Ar_1$, $HetAr_1$, $HetCy_1$ and $Cy_1$ is optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo. In a specific embodiment, $R^3$ is $(C_1-C_8)$alkyl, aryl$(C_0-C_3)$alkyl or $CO_2R^4$. Each group represented by $R^3$ is optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$, $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$, wherein the $(C_1-C_0)$alkyl and the alkyl portion of aryl$(C_1-C_3)$alkyl in the group represented by $R^3$ is further optionally substituted with oxo. In a specific embodiment, $R^3$ is $CO_2R^4$, phenyl, $(C_1-C_3)$alkyl or benzyl, each group represented by $R^3$ is optionally substituted with halogen, nitro, cyano, $(C_1-C_3)$alkyl, halo$(C_1-C_3)$alkyl, $(C_1-C_3)$alkoxy, halo$(C_1-C_3)$alkoxy, $N(R^4)_2$ or $CON(R^4)_2$. In a specific embodiment, $R^3$ is phenyl, $(C_1-C_3)$alkyl or benzyl, each group represented by $R^3$ is optionally substituted with halogen, nitro, cyano, $(C_1-C_3)$alkyl, halo$(C_1-C_3)$alkyl, $(C_1-C_3)$alkoxy, halo$(C_1-C_3)$alkoxy, $N(R^4)_2$ or $CON(R^4)_2$.

Each $R^4$ is independently (a) hydrogen; or (b) $(C_1-C_{10})$alkyl, aryl$(C_0-C_3)$alkyl, $(C_1-C_{10})$alkyl and aryl$(C_0-C_3)$alkyl in the group represented by $R^4$ are optionally substituted with halogen, $(C_1-C_3)$alkoxy, $(C_1-C_3)$alkyl, halo$(C_1-C_3)$alkyl, halo($C_1$-$C_3$)alkoxy, cyano or nitro. In a specific embodiment, $R^4$ is independently hydrogen or ($C_1$-$C_3$)alkyl.

$R^5$ is hydrogen or ($C_1$-$C_6$)alkyl. In a specific embodiment, $R^5$ is hydrogen.

Each $R^6$ is independently selected from halogen, nitro, cyano, ($C_1$-$C_3$)alkyl, cyclo($C_3$-$C_6$)alkyl, halo($C_1$-$C_3$)alkyl, hydroxy($C_1$-$C_3$)alkyl, oxo, $OR^4$, halo($C_1$-$C_3$)alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, $(CH_2)_xOR^4$, $(CH_2)_xO(CH_2)_xCO_2R^4$, optionally substituted aryl, optionally substituted heteroaryl, optionally substituted heterocyclyl and optionally substituted cycloalkyl, wherein the aryl, heteroaryl, heterocyclyl and cycloalkyl in the group represented by $R^6$ are further optionally substituted with one to three groups represented by $R^7$. In a specific embodiment, each $R^6$ is independently selected from halogen, cyano, ($C_1$-$C_3$)alkyl, cyclo($C_3$-$C_6$)alkyl, halo($C_1$-$C_3$)alkyl, hydroxy($C_1$-$C_3$)alkyl, oxo, $OR^4$, halo($C_1$-$C_3$)alkoxy, $(CH_2)_xN(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xNR^4CON(R^4)_2$, and $(CH_2)_xOC(=O)N(R^4)_2$. In another specific embodiment each $R^6$ is independently selected from halogen, cyano, ($C_1$-$C_3$)alkyl, cyclo($C_3$-$C_6$)alkyl, halo($C_1$-$C_3$)alkyl, hydroxy($C_1$-$C_3$)alkyl, $OR^4$, halo($C_1$-$C_3$)alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, $(CH_2)_xOR^4$, $(CH_2)_xO(CH_2)_xCO_2R^4$, optionally substituted aryl, optionally substituted heteroaryl, optionally substituted heterocyclyl and optionally substituted cycloalkyl, wherein the aryl, heteroaryl, heterocyclyl and cycloalkyl in the group represented by $R^6$ are further optionally substituted with one to three groups represented by $R^7$. Exemplary aryl, heterocyclyl and heteroaryl groups represented by $R^6$ are described later in the definitions of these terms. Preferred aryls include naphthyl and phenyl. Preferred heteroaryls include furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, quinazolinyl, benzothienyl, benzofuranyl, 2,3-dihydrobenzofuranyl, benzodioxolyl, benzimidazolyl, indazolyl, benzisoxazolyl, benzoxazolyl, benzothiazolyl, cinnolinyl, phthalzinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,3,4-thiadiazolyl, 1,2,4-triazinyl, 1,3,5-triazinyl, tetrazolyl, and pteridinyl. Preferred heterocyclyl include oxodihydropyridyl, oxodihydropyridazinyl, oxodihydropyrimidinyl or oxodihydropyrazinyl.

Each $R^7$ is independently selected from halogen, nitro, cyano, ($C_1$-$C_3$)alkyl, halo($C_1$-$C_3$)alkyl, cyclo($C_3$-$C_6$)alkyl, hydroxyl($C_1$-$C_6$)alkyl, ($C_1$-$C_3$)alkoxy, halo($C_1$-$C_3$)alkoxy, $N(R^4)_2$ and $CON(R^4)_2$, provided that $R^7$ also includes oxo when, heteroaryl, heterocyclyl and cycloalkyl in the group represented by $R^6$ are substituted with $R^7$.

x is 0, 1, 2 or 3. In a specific embodiment, x is 0 or 1. In a specific embodiment x is 1. In a specific embodiment, x is 0.

A' is a bond, $CH_2$, or -AO—. In a specific embodiment A' is a bond. In a specific embodiment, A' is $CH_2$. In a specific embodiment, A' is -AO—. In a specific embodiment, A' is —O—. In yet another specific embodiment, A' is —$CH_2$O—. In a specific embodiment, O in the group represented by -AO— is connected to B.

A is a bond or $CH_2$. In a specific embodiment, A is a bond. In a specific embodiment, A is $CH_2$.

m is 0, 1, 2, 3 or 4. In a specific embodiment, m is 0. In a specific embodiment, m is 1. In a specific embodiment, m is 2. In a specific embodiment, m is 3. In a specific embodiment, m is 4.

n is 1, 2, 3 or 4. In a specific embodiment, n is 1. In a specific embodiment, n is 2. In a specific embodiment, n is 3. In a specific embodiment, n is 4.

p is 0, 1, 2 or 3. In a specific embodiment, p is 0 or 1.

$X_1$ is N or $CR^5$. In a specific embodiment, $X_1$ is N. In a specific embodiment, $X_1$ is $CR^5$.

A first embodiment of the invention is a compound of any one of Formulas IV-XX:

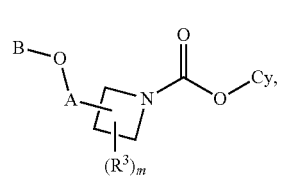

IV

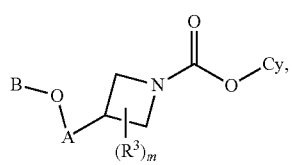

V

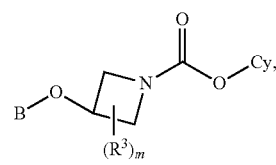

VI

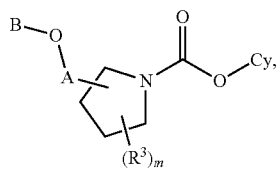

VII

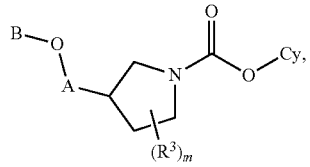

VIII

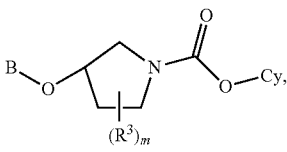

IX

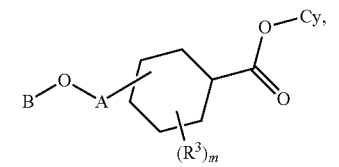  X

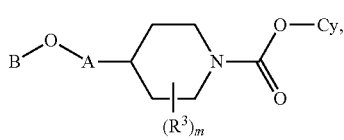  XI

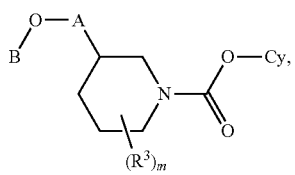  XII

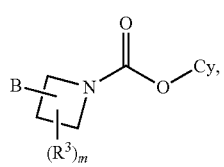  XIII

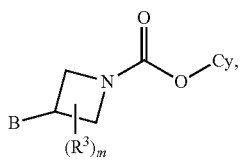  XIV

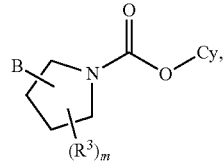  XV

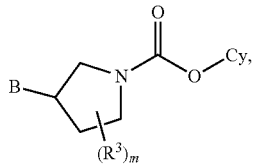  XVI

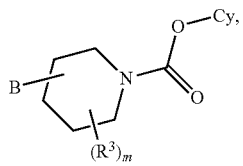  XVII

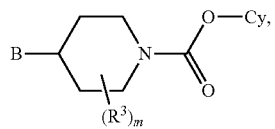  XIII

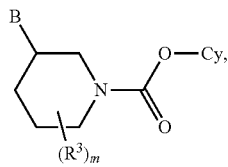  XIX

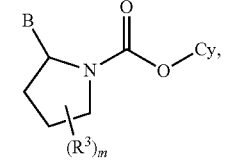  XX or a pharmaceutically acceptable salt thereof, wherein values and specific values for the variables in Formulas IV-XX are as defined for Formulas I, II and III above.

A second embodiment of the invention is a compound of any one of Formulas IV-XX, wherein:

Cy is $(C_7-C_{12})$bicycloalkyl or $(C_9-C_{12})$tricycloalkyl, wherein each $C_7-C_{12}$)bicycloalkyl or $(C_9-C_{12})$tricycloalkyl in the group represented by Cy is optionally substituted with 1-3 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$. Alternatively, Cy is adamantyl, optionally substituted with 1-3 groups independently selected from halogen, cyano, hydroxy, hydroxy$(C_1-C_3)$alkyl, $N(R^4)_2$, $CO_2R^4$; $CON(R^4)_2$, $CH_2CON(R^4)_2$, $SO_2N(R^4)_2$, $SO_2R^4$, $NR^4COR^4$ or $OC(=O)N(R^4)_2$.

$R^3$ is $(C_1-C_8)$alkyl, aryl$(C_0-C_3)$alkyl or $CO_2R^4$, wherein each group represented by $R^3$ is optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$, wherein the $(C_1-C_8)$ alkyl and the alkyl portion of aryl$(C_0-C_3)$alkyl in the group represented by $R^3$ are further optionally substituted with oxo;

$R^4$ is independently hydrogen or $(C_1-C_3)$ alkyl; and values and specific values for the remainder of the variables in Formulas IV-XX are as defined for Formulas I, II and III above.

In preferred embodiment, $R^3$ is phenyl, $C_1-C_3$alkyl, $CO_2R^4$ or benzyl and the remainder of the variables in Formulas IV-XX are as defined in the first and second embodiment. Alternatively, $R^3$ is phenyl, $C_1-C_3$alkyl or benzyl.

In preferred embodiment, m is 0 and the remainder of the variables in Formulas IV-XX are as defined in the first and second embodiment. Alternatively, m is 1 and $R^3$ is phenyl, $C_1-C_3$alkyl, $CO_2R^4$ or benzyl. In another alternative, m is 1 and $R^3$ is phenyl, $C_1-C_3$alkyl or benzyl.

In preferred embodiment, A is bond in Formulas X, XI and XII and the remainder of the variables in Formulas X, XI and XII are as defined in the first and the second embodiment or in the preceding paragraph. Alternatively, A is bond and $R^3$ is phenyl, $C_1-C_3$alkyl, $CO_2R^4$ or benzyl. In another alternative, A is bond and $R^3$ is phenyl, $C_1-C_3$alkyl or benzyl.

A third embodiment of the invention is a compound of any one of Formulas XXI-XXXXII, or a pharmaceutically acceptable salt thereof:

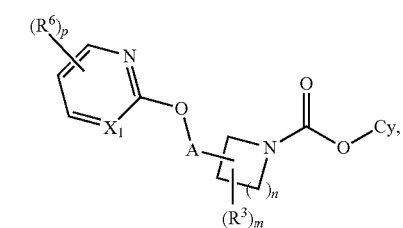
XXI
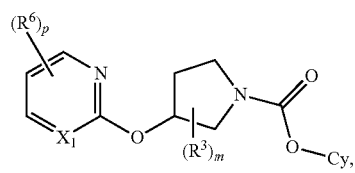
XXII
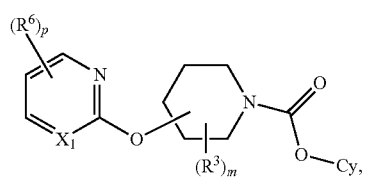
XXIII
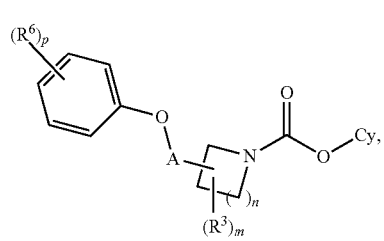
XXIV
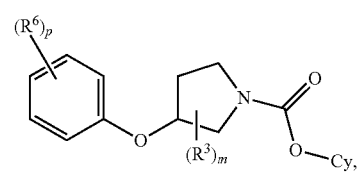
XXV
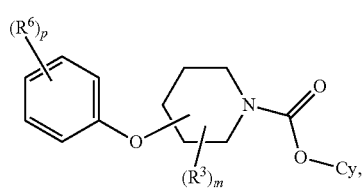
XXVI
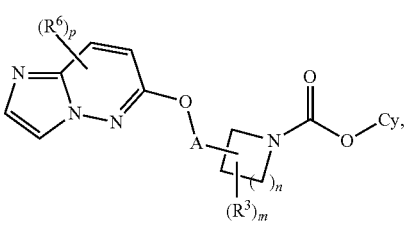
XXVII
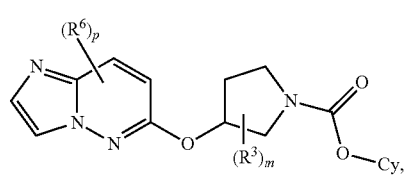
XXVIII
-continued
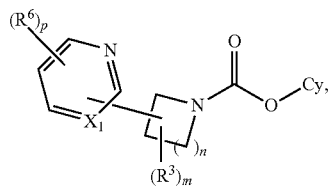
XXIX
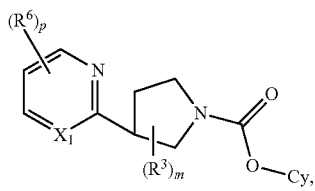
XXX
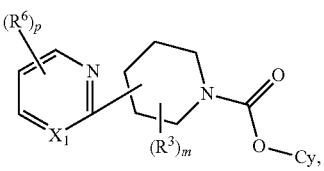
XXXI
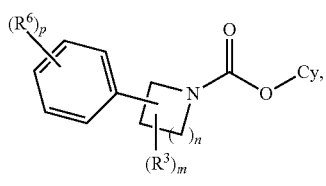
XXXII
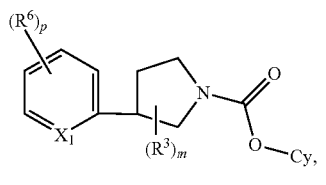
XXXIII
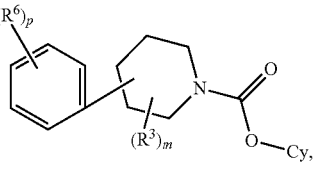
XXXIV
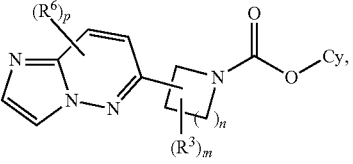
XXXV
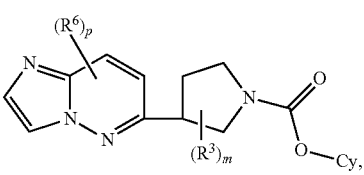
XXXVI -continued

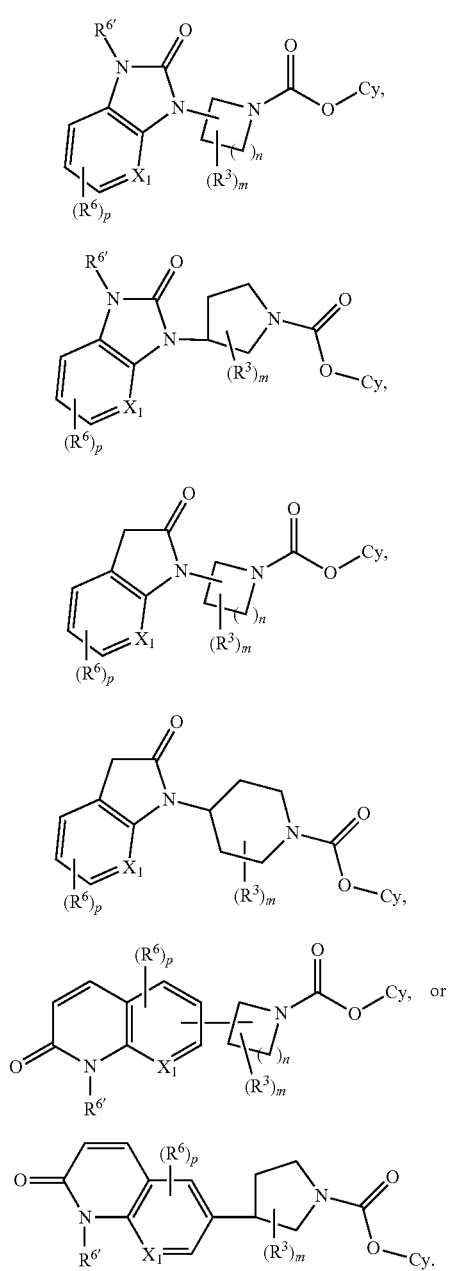

XXXVII

XXXVIII

XXXIX

XXXX

XXXXI

XXXXII wherein:
$R^6$ is halogen, nitro, cyano, $(C_1-C_3)$alkyl, cyclo$(C_3-C_6)$alkyl, halo$(C_1-C_3)$alkyl, hydroxy$(C_1-C_3)$alkyl, $OR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, $(CH_2)_xOR^4$, $(CH_2)_xO(CH_2)_xCO_2R^4$, optionally substituted aryl, optionally substituted heteroaryl, optionally substituted heterocyclyl and optionally substituted cycloalkyl, wherein the aryl, heteroaryl, heterocyclyl and cycloalkyl in the group represented with $R^6$ are further optionally substituted with one to three groups represented by $R^7$. Alternatively, $R^6$ is halogen or halo$(C_1-C_3)$alkyl;
p is 0, 1, 2 or 3;
$X_1$ is N or $CR^5$. Alternatively, $X_1$ is $CR^5$; $R^5$ is $R^5$ is hydrogen or $(C_1-C_6)$alkyl;

$R^{6'}$ is hydrogen or $R^6$ in Formulas XXXVII-XXXVIII and XXXXI-XXXXII;
values and specific values for the remainder of the variables in Formulas XXI-XXXXII are as defined in the first and the second embodiment.

In a fourth embodiment of the invention values and specific values for the variables in Formulas XXI-XXXXII are: $R^6$ is halogen, nitro, cyano, $(C_1-C_3)$alkyl, cyclo$(C_3-C_6)$alkyl, halo$(C_1-C_3)$alkyl, hydroxy$(C_1-C_3)$alkyl, $OR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, $(CH_2)_xOR^4$, $(CH_2)_xO(CH_2)_xCO_2R^4$, optionally substituted aryl, optionally substituted heteroaryl, optionally substituted heterocyclyl and optionally substituted cycloalkyl, wherein the aryl, heteroaryl, heterocyclyl and cycloalkyl in the group represented with $R^6$ are further optionally substituted with one to three groups represented by $R^7$. Alternatively, $R^6$ is halogen or halo$(C_1-C_3)$alkyl;
p is 0, 1, 2 or 3;
$X_1$ is N or $CR^5$. Alternatively, $X_1$ is $CR^5$;
Cy is $(C_7-C_{12})$bicycloalkyl or $(C_6-C_{12})$tricycloalkyl, wherein each $C_7-C_{12}$bicycloalkyl or $(C_6-C_{12})$tricycloalkyl in the group represented by Cy is optionally substituted with 1-3 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$;
$R^3$ is $(C_1-C_8)$alkyl, aryl$(C_0-C_3)$alkyl or $CO_2R^4$, each group represented by $R^3$ is optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$, wherein the $(C_1-C_8)$alkyl and the alkyl portion of aryl$(C_0-C_3)$alkyl in the group represented by $R^3$ are further optionally substituted with oxo;
$R^4$ is independently hydrogen or $(C_1-C_3)$ alkyl;
$R^{6'}$ is hydrogen or $R^6$ in Formulas XXXVII-XXXVIII and XXXXI-XXXXII; and
values and specific values for the remainder of the variables in Formulas XXI-XXXXII are as defined in the first, second, third or fourth embodiment.

A fifth embodiment of the invention is a compound of any one of Formulas XXXXIII to LXV, or a pharmaceutically acceptable salt thereof:

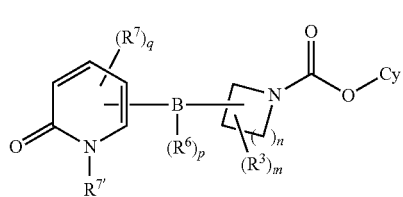

XXXXIII

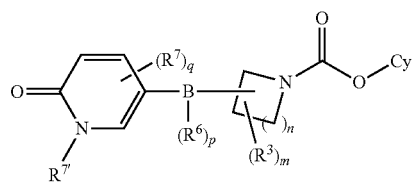

XXXXIV

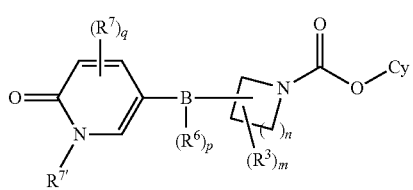
XXXXV
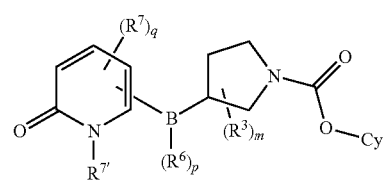
XXXXVI
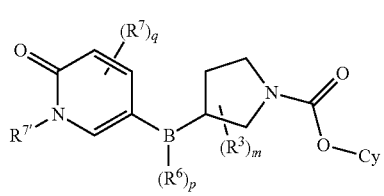
XXXXVII
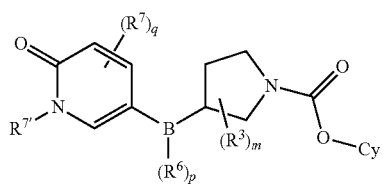
XXXXVIII
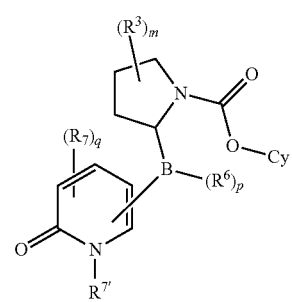
XXXXIX
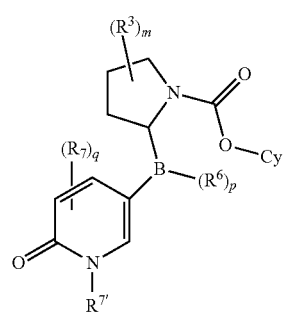
L
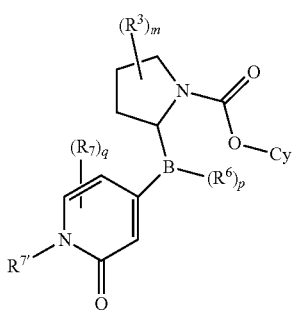
LI
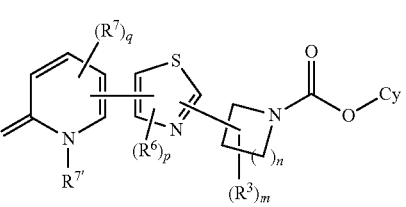
LII
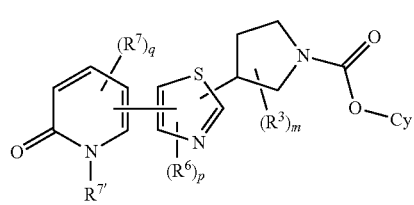
LIII
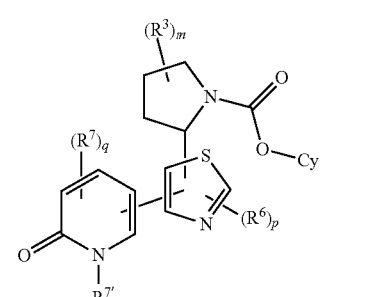
LIV
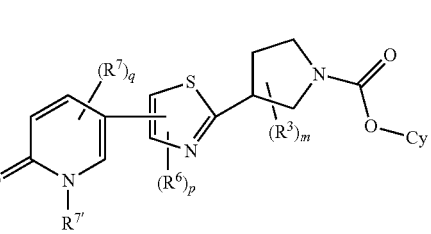
LV
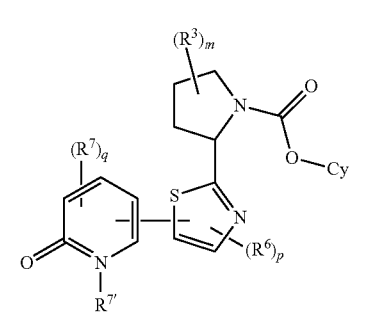
LVI

LVII

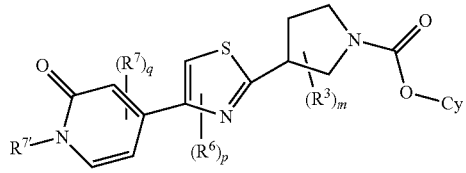

LVIII

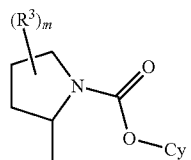

LIX

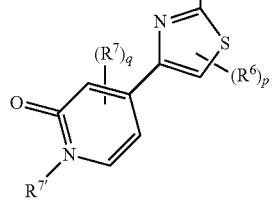

LX

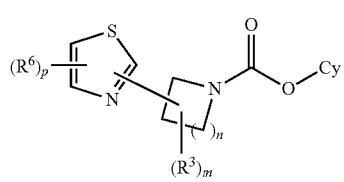

LXI

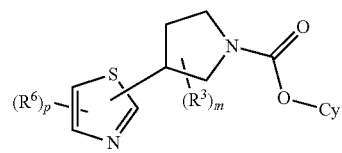

LXII

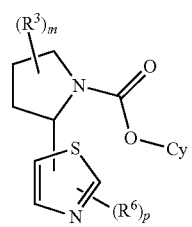

LXIII

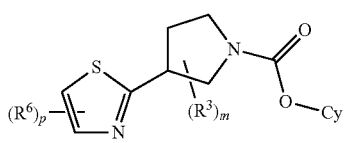

LXIV

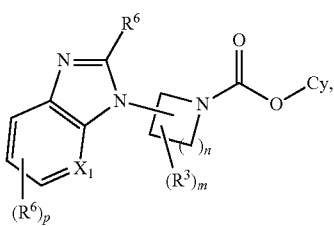

LXV

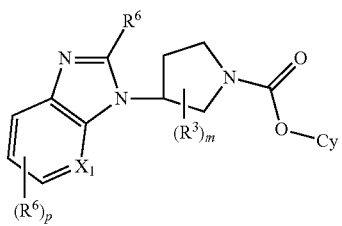

$R^6$ is halogen, nitro, cyano, $(C_1\text{-}C_3)$alkyl, cyclo$(C_3\text{-}C_6)$ alkyl, halo$(C_1\text{-}C_3)$alkyl, hydroxy$(C_1\text{-}C_3)$alkyl, $OR^4$, halo$(C_1\text{-}C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, $(CH_2)_xOR^4$, $(CH_2)_xO(CH_2)_xCO_2R^4$, optionally substituted aryl, optionally substituted heteroaryl, optionally substituted heterocyclyl and optionally substituted cycloalkyl, wherein the aryl, heteroaryl, heterocyclyl and cycloalkyl in the group represented with $R^6$ are further optionally substituted with one to three groups represented by $R^7$. Alternatively, $R^6$ is halogen or halo$(C_1\text{-}C_3)$alkyl;

p is 0, 1, 2 or 3;

$R^7$ is halogen, nitro, cyano, $(C_1\text{-}C_3)$alkyl, halo$(C_1\text{-}C_3)$ alkyl, cyclo$(C_3\text{-}C_6)$alkyl, hydroxyl$(C_1\text{-}C_5)$alkyl, $(C_1\text{-}C_3)$ alkoxy, halo$(C_1\text{-}C_3)$alkoxy, $N(R^4)_2$ and $CON(R^4)_2$;

$R^{7'}$ is H or $R^7$ q is 0, 1 or 2;

values and specific values for the remainder of the variables in Formulas XXXXIII to LXIII are as defined in the first and the second embodiment.

In preferred embodiment of the invention, in Formulas XXI-LXIII, Cy is adamantyl, optionally substituted with 1-3 groups independently selected from halogen, cyano, hydroxy, hydroxy$(C_1\text{-}C_3)$alkyl, $N(R^4)_2$, $CO_2R^4$; $CON(R^4)_2$, $CH_2CON(R^4)_2$, $SO_2N(R^4)_2$, $SO_2R^4$, $NR^4COR^4$ or $OC(=O)N(R^4)_2$ and values and specific values for the remainder of the variables is as defined in the first and the second embodiment. Alternatively, Cy is adamantyl, optionally substituted with $CONH_2$ or hydroxy.

In one embodiment compounds of the invention exclude

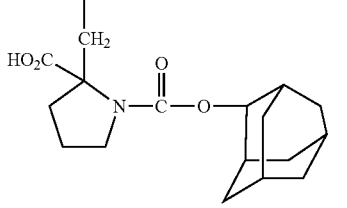 or

-continued

[Chemical structure shown]

wherein t-BuO is t-butyloxy and MeO is methyloxy, or a pharmaceutical or a pharmaceutically acceptable salt thereof.

Specific Examples of the instant inventions are compounds presented in Examples 1-6.

DEFINITIONS

The term "alkyl", used alone or as part of a larger moiety such as "alkoxyalkyl" or "alkylamine" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, i-pentyl, n-hexyl, n-heptyl, n-octyl, n-nonyl, n-decyl and the like.

The term "cycloalkyl" means a monocyclic, bicyclic or tricyclic, saturated hydrocarbon ring having 3-10 carbon atoms. Bicyclic and tricyclic cycloalkyls can be fused or bridged. Examples of cycloalkys include cyclopropyl, cyclobutyl, cyclopentyl, cyclohexyl, cycloheptyl, cyclooctyl, bicyclo[2.2.2]octyl, bicyclo[2.2.1]heptyl, Spiro[4.4]nonane, adamantyl and the like. Unless otherwise described, exemplary substituents for a substituted cycloalkyl group include the substituents described for the cycloalkyl group represented by $R^6$.

A fused ring system has two rings which have two adjacent ring atoms in common. Decalin is an example of a fused bicyclic ring systems.

A bridged ring system has two rings which have three or more adjacent ring atoms in common. Examples of bridged bicyclic ring system include, but are not limited to, bicyclo[1.1.0]butane, bicyclo[1.2.0]pentane, bicyclo[2.2.0]hexane, bicyclo[3.2.0]heptane, bicyclo[3.3.0]octane, bicyclo[4.2.0]octane, bicyclo[2.2.1]heptane, bicyclo[2.2.2]octane, bicyclo[3.2.1]octane, bicyclo[3.2.2]nonane, bicyclo[3.3.1]nonane, bicyclo[3.3.2]decane bicyclo[3.3.3]undecane, azabicyclo[3.3.1]nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane and 2-oxabicyclo[2.2.2]octane.

"Aryl", used alone or as part of a larger moiety as in "arylalkyl", "arylalkoxy", or "aryloxyalkyl", means a 6-10 membered carbocyclic aromatic monocyclic or polycyclic ring system. Examples include phenyl and naphthyl. The term "aryl" also includes phenyl rings fused to a non-aromatic carbocyclic ring or to a heterocyclyl group, wherein the aryl is attached to the remainder of the molecule through the phenyl ring, the non-aromatic carbocyclic ring, or through the heterocyclyl group. Examples include 1,2-dihydroquinoline, 2-oxo-1,2-dihydroquinoline, 2-oxoindoline, oxoindoline, indoline, benzo[d]imidazole and benzo[d]thiazole. The term "aryl" may be used interchangeably with the terms "aromatic group", "aryl ring" "aromatic ring", "aryl group" and "aromatic group". Unless otherwise described, exemplary substituents for a substituted aryl group include the substituents described for the heterocyclyl group represented by $R^6$.

"Hetero" refers to the replacement of at least one carbon atom member in a ring system with at least one heteroatom selected from N, S, and O. A hetero ring may have 1, 2, 3, or 4 carbon atom members replaced by a heteroatom.

"Heteroaryl", used alone or as part of a larger moiety as in "heteroarylalkyl" or "heteroarylalkoxy", means a 5-10 membered monovalent heteroaromatic monocyclic and polycylic ring system radical containing 1 to 4 heteroatoms independently selected from N, O, and S. The term "heteroaryl" also includes a monocyclic heteroaryl ring fused to a non-aromatic carbocyclic ring or to a heterocyclyl group, wherein the heteroaryl is attached to the remainder of the molecule through the monocyclic heteroaryl ring, the non-aromatic carbocyclic ring, or through the heterocyclyl group. Heteroaryl groups include furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, indolizinyl, indolyl, isoindolyl, benzo[b]furyl, benzo[b]thienyl, indazolyl, imidazo[4,5-b]pyridinyl, 2-oxo-1H-imidazo[4,5-b]pyridinyl, benzimidazolyl, benzthiazolyl, purinyl, 4H-quinolizinyl, quinolinyl, isoquinolinyl, quinazolinyl, benzothienyl, benzofuranyl, 2,3-dihydrobenzofuranyl, benzodioxolyl, benzimidazolyl, indazolyl, benzisoxazolyl, benzoxazolyl, benzothiazolyl, cinnolinyl, phthalzinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,3,4-thiadiazolyl, 1,2,4-triazinyl, 1,3,5-triazinyl, tetrazolyl, and pteridinyl. The terms "heteroaryl", "heteroaromatic", "heteroaryl ring", "heteroaryl group" and "heteroaromatic group" are used interchangeably herein. "Heteroarylalkyl" means alkyl substituted with heteroaryl; and "heteroarylalkoxy" means alkoxy substituted with heteroaryl. Unless otherwise described, exemplary substituents for a substituted heterocyclyl group include the substituents described for the heteroaryl group represented by $R^6$.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, oxodihydropyridyl, oxodihydropyridazinyl, oxodihydropyrimidinyl, oxodihydropyrazinyl, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide and isothiazolidine 1,1-dioxide. Unless otherwise described, exemplary substituents for a substituted heterocyclyl group include the substituents described for the heterocyclyl group represented by $R^6$.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

The following abbreviations have the indicated meanings:

| Abbreviation | Meaning |
| --- | --- |
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| EA, EtOAc | Ethyl acetate |
| EDC•HCl | 1-[3-(dimethylamino)propyl]-3-ethylcarbodiimide hydrochloride |
| Equiv | equivalents |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazole-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |

| Abbreviation | Meaning |
|---|---|
| Pd$_2$(dba)$_3$ | tris(dibenzylideneacetone)dipalladium(0) |
| PE | petroleum ether |
| Quant | quantitative yield |
| Satd | saturated |
| SFC | Supercritical Fluid Chromatography |
| SOCl$_2$ | thionyl chloride |
| SPA | scintillation proximity assay |
| SPE | solid phase extraction |
| TBS | t-butyldimethylsilyl |
| TBSCl | t-butyldimethylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |
| TFAA | trifluoroacetic anhydride |
| Tlc | thin layer chromatography |
| TMS | trimethylsilyl |
| TMSCl | chlorotrimethylsilane or trimethylsilyl chloride |
| $t_R$ | retention time |
| TsOH | p-toluenesulfonic acid |

General Description of Synthesis

Compounds of Formula I can be prepared by several processes. In the discussion below R$^1$, R$^2$, R$^3$, R$^4$, R$^5$, R$^6$, A', A, B, Cy, m and n have the meanings indicated above unless otherwise noted. In cases where the synthetic intermediates and final products of Formulas I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and generally not described explicitly. Generally reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In a first process, a compound of Formula II, can be prepared by reaction of a cyclic amine of Formula 2 with an electrophile of Formula 3, wherein Z$^1$ is a leaving group such as halide, aryloxide, 1-imidazolyl and the like, in the presence of a soluble base such as i-Pr$_2$NEt or an insoluble base such as K$_2$CO$_3$ in an inert solvent such as THF, CH$_2$Cl$_2$ or MeCN at 0-100° C. for 1-24 h.

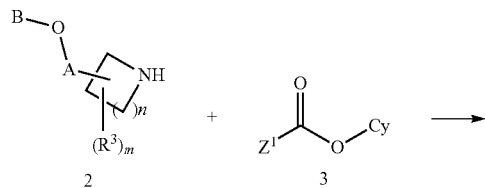

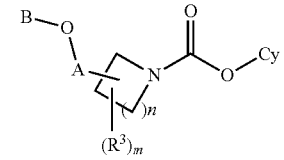

Amines of Formula 2 can be prepared from protected amines of Formula 4, wherein Z$^2$ is an amine protecting group such as Boc, Teoc, Cbz or the like, by reaction with a compound of Formula 5, wherein B is aryl or heteroaryl and Z$^3$ is halide, methanesulfonate or trifluoromethanesulfonate, followed by removal of protecting group Z$^2$.

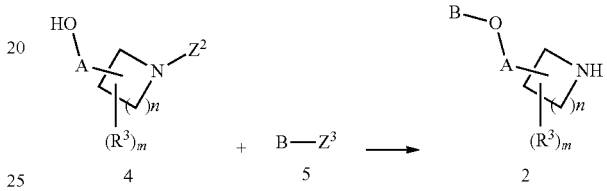

When B is aryl or heteroaryl bearing an electron withdrawing group such as cyano, trifluoromethyl or the like attached ortho or para to Z$^3$, Z$^3$ is preferably fluoro, bromo or chloro and the reaction can be run in the presence of a base such as NaH at a temperature from 0-100° C. in a solvent such as THF, DMF or DME. When B does not bear an electron withdrawing group, Z$^3$ is preferably bromine or iodine and the reaction is run in the presence of a palladium or copper catalyst and suitable additives.

Electrophiles of Formula 3, wherein Z$^1$ is Clare chloroformates and are prepared by reaction of alcohols of formula 6 with phosgene or triphosgene in an inert solvent such as toluene, CH$_2$Cl$_2$ or THF in the presence of a base such as pyridine at −20° C. to 80° C., preferably 0° C. to 25° C. for between 0.5 h and 24 h.

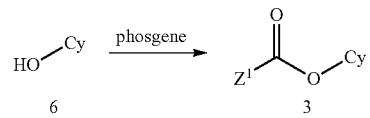

Electrophiles of Formula 3 wherein Z$^1$=aryloxide are carbonates and are prepared by reaction of alcohols of Formula 6 with aryl chloroformates of Formula 7 in an inert solvent such as toluene, CH$_2$Cl$_2$ or THF in the presence of a base such as triethylamine at 0° C. to 80° C., preferably 5° C. to 25° C. for between 1 h and 24 h.

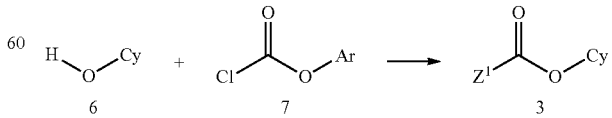

Similarly, treatment of alcohols of Formula 6 with carbonyl diimidazole affords compounds of Formula 3, wherein Z$^1$ is 1-imidazolyl. Additionally, treatment of alcohols of Formula 6 with disuccinimidyl carbonate affords compounds of Formula 3, wherein $Z^1$ is succinimidyl-1-oxy.

In a second process, a compound of Formula II can be prepared by reaction of a compound of Formula 8, wherein $Z^4$ is a leaving group such as such as halide, aryloxide or azole, preferably chloride, with an alcohol of formula 6 in a solvent such as pyridine at 50-150° C.

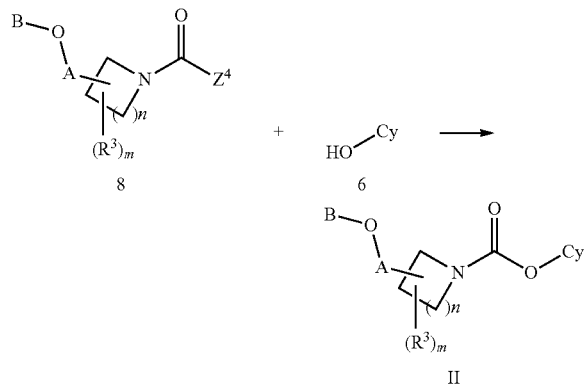

Alternatively, the alkoxide anion of alcohol 6 can be formed using a strong base such as NaH in an inert solvent such as THF and DMF and reacted with 8.

Intermediates of Formula 8, wherein $Z^4$ is chlorine, can be prepared by reaction of amines of Formula 2 with phosgene or triphosgene in the presence of a base such as pyridine at −40 to 40° C., preferably around 0° C., in an inert solvent such as $CH_2Cl_2$, THF or MeCN for between 30 min and 24 h.

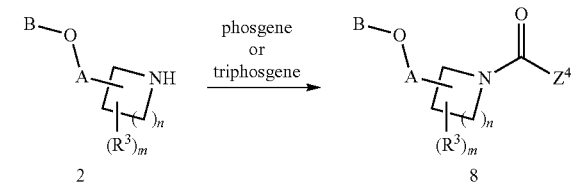

In a third process a compound of Formula II, wherein B is aryl or heteroaryl, can be prepared by reaction of an intermediate of Formula 5 with an amine of Formula 13.

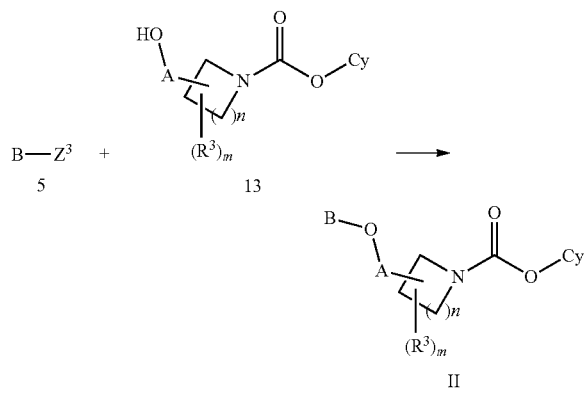

When B is aryl or heteroaryl bearing an electron withdrawing group such as cyano, trifluoromethyl or the like attached ortho or para to $Z^3$, $Z^3$ is preferably fluoro or chloro and the reaction can be run in the presence of a base such as NaH at a temperature from 0-100° C. in a solvent such as THF, DMF or DME. When B does not bear an electron withdrawing group, $Z^3$ is preferably bromine or iodine and the reaction is run in the presence of a palladium or copper catalyst and suitable additives.

In a fourth process, a compound of Formula I can be prepared from another compound of Formula I. For example:

(1) a compound of Formula I, wherein Cy is substituted by $CO_2Me$, can be treated with $LiBH_4$ to afford a compound of Formula I, wherein Cy is substituted by $CH_2OH$.

(2) a compound of Formula I, wherein Cy is substituted with $CO_2Me$, can be treated with MeMgBr to afford a compound of Formula I, wherein Cy is substituted by $C(Me)_2OH$.

(3) a compound of Formula I, wherein Cy is substituted by $CO_2H$, can be coupled with $NH_3$ using, for example, EDC to afford a compound of Formula I, wherein Cy is substituted with $CONH_2$.

(4) a compound of Formula I, wherein Cy is substituted by $CONH_2$, can be treated with trifluoroacetic anhydride and pyridine, to afford a compound of Formula I, wherein Cy is substituted with CN.

(5) A compound of Formula I, wherein B or $R^6$ is pyridyl can be oxidized using, for example, m-CPBA, to give a compound of Formula I, wherein B or $R^6$ is N-oxopyridyl.

(6) A compound of Formula I, wherein B or $R^6$ is N-oxopyridyl can be rearranged using, for example, $(CF_3CO)_2O$, to give a compound of Formula I, wherein B or $R^6$ is 2-oxo-1,2-dihydropyridyl.

(7) A compound of Formula I, wherein B or $R^6$ is 2-oxo-1,2-dihydropyridyl can be alkylated using, for example, KOt-Bu or $Cs_2CO_3$ and MeI, to give a compound of Formula I, wherein B or $R^6$ is 1-methyl-2-oxo-1,2-dihydropyridyl.

In a first alternate process, a compound of Formula III, can be prepared by reaction of a cyclic amine of Formula 2' with an electrophile of Formula 3, wherein $Z^1$ is a leaving group such as halide, aryloxide, 1-imidazolyl and the like, in the presence of a soluble base such as i-$Pr_2NEt$ or an insoluble base such as $K_2CO_3$ in an inert solvent such as THF, $CH_2Cl_2$ or MeCN at 0-100° C. for 1-24 h.

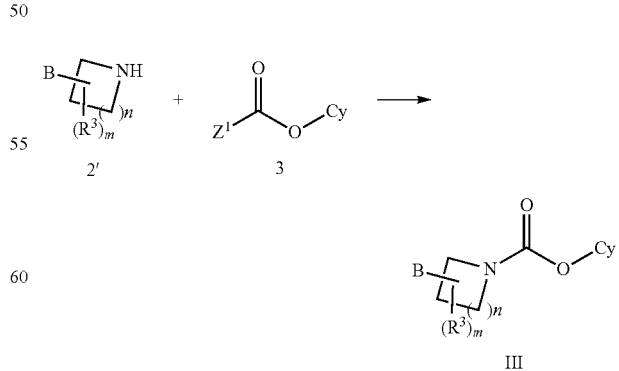

Amines of Formula 2' can be prepared by reduction of lactams of Formula 4', with for example $LiAlH_4$ or $BH_3.THF$.

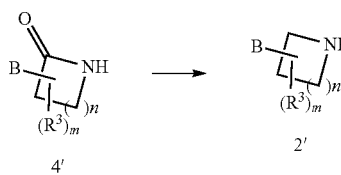

Amines of Formula 2', wherein n=2 or 3, can be prepared by catalytic hydrogenation of unsaturated amines of 5'.

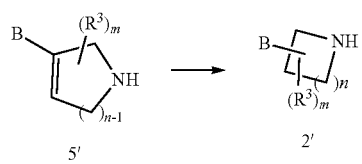

Amines of Formula 5' can be prepared by Suzuki coupling of boronates of Formula 6' with compounds of Formula 7' wherein $Z^5$ is halide, alkylsulfonate or haloalkylsulfonate, preferably bromide, iodide or trifluoromethanesulfonate.

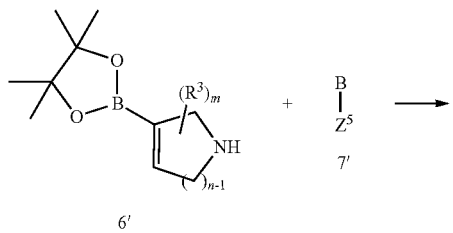

Secondary amines of Formula 2', wherein n=2 and m=0, can be prepared by debenzylation of tertiary amines of Formula 8' using, for example, 1-chloroethyl chloroformate.

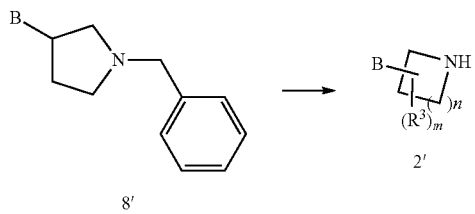

Tertiary amines of Formula 8' can be prepared by dipolar cycloaddition of vinyl compounds of Formula 9' with 10'.

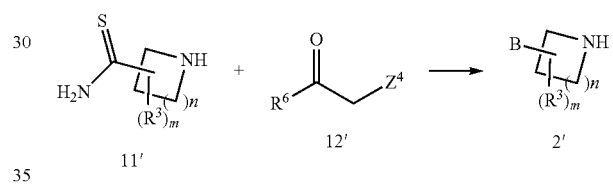

Secondary amines of Formula 2', wherein B is a 2-thiazolyl group substituted by $R^6$ at the 4-position, can be prepared by reaction of thioamides of Formula 11' with halomethylketones of Formula 12' wherein $Z^4$ is a halogen, preferably chloro or bromo.

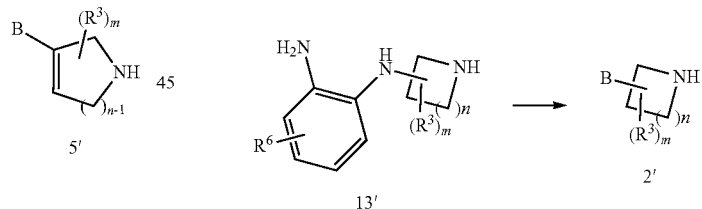

Secondary amines of Formula 2', wherein B is 2-oxo-2,3-dihydro-1H-benzo[d]imidazol-1-yl optionally substituted by $R^6$ are prepared by reaction of phenyldiamines of Formula 13' with phosgene, CDI, triphosgene or similar reagents.

Phenylenediamines of Formula 13' can be prepared by reduction of nitro compounds of Formula 14' which can be prepared by $S_NAr$ reaction of amines of Formula 15' with ortho-halonitrobenzenes of Formula 16', wherein $Z^4$ is fluoro, chloro or bromo.

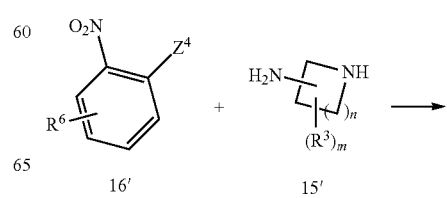

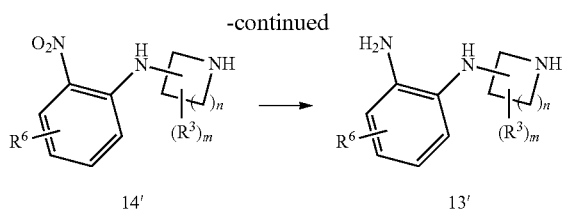

Secondary amines of Formula 2', wherein B is 1H-benzo[d]imidazol-1-yl optionally substituted by $R^6$ can be prepared from phenylenediamines of Formula 13' by acylation to give 17', wherein $R^{6'}$ is an alkyl or substituted alkyl group, followed by acid-catalyzed ring closure, using, for example, acetic acid.

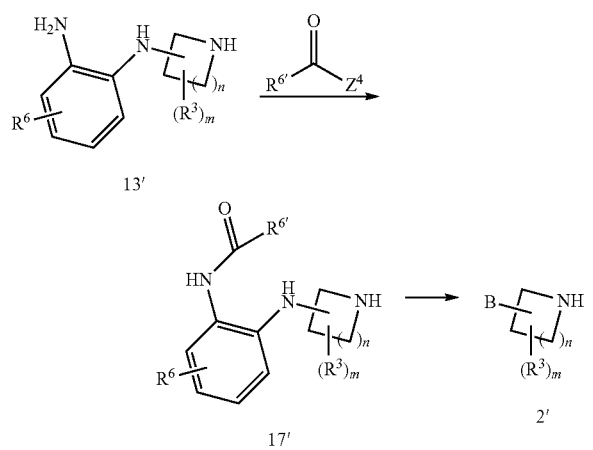

Electrophiles of Formula 3, wherein $Z^1$ is Clare chloroformates and are prepared by reaction of alcohols of formula 18' with phosgene, diphosgene or triphosgene in an inert solvent such as toluene, $CH_2Cl_2$ or THF in the presence of a base such as pyridine at $-20°$ C. to $80°$ C., preferably $0°$ C. to $25°$ C., for between 0.5 h and 24 h.

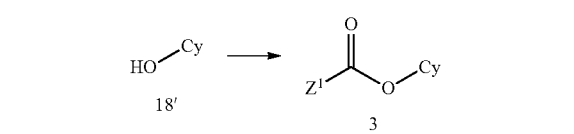

Electrophiles of Formula 3 wherein $Z^1$=aryloxide are carbonates and are prepared by reaction of alcohols of Formula 18' with aryl chloroformates of Formula 19' in an inert solvent such as toluene, $CH_2Cl_2$ or THF in the presence of a base such as triethylamine at $0°$ C. to $80°$ C., preferably $5°$ C. to $25°$ C. for between 1 h and 24 h.

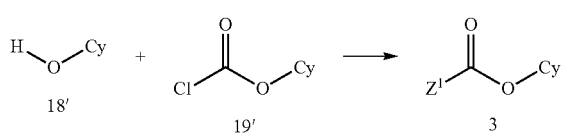

Similarly, treatment of alcohols of Formula 18' with carbonyl diimidazole affords compounds of Formula 3, wherein $Z^1$ is 1-imidazolyl. Additionally, treatment of alcohols of Formula 18' with disuccinimidyl carbonate affords compounds of Formula 3, wherein $Z^1$ is succinimidyl-1-oxy.

In a second alternate process, a compound of Formula III can be prepared by reaction of a compound of Formula 20', wherein $Z^4$ is a leaving group such as such as halide, aryloxide or azole, preferably chloride, with an alcohol of formula 18' in a solvent such as pyridine at $50-150°$ C.

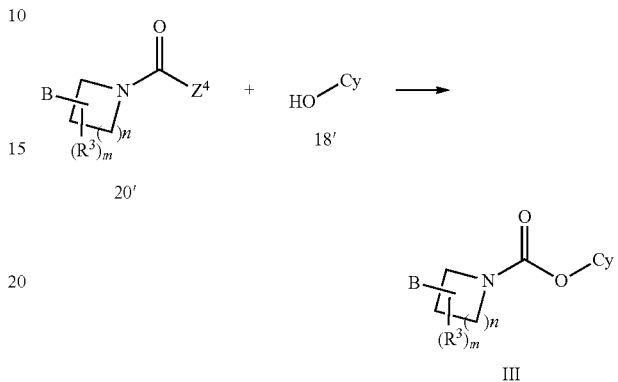

Alternatively, the alkoxide anion of alcohol 18' can be formed using a strong base such as NaH in an inert solvent such as THF and DMF and reacted with 20'.

Intermediates of Formula 20', wherein $Z^4$ is chlorine, can be prepared by reaction of amines of Formula 2' with phosgene or triphosgene in the presence of a base such as pyridine at $-40$ to $40°$ C., preferably around $0°$ C., in an inert solvent such as $CH_2Cl_2$, THF or MeCN for between 30 min and 24 h.

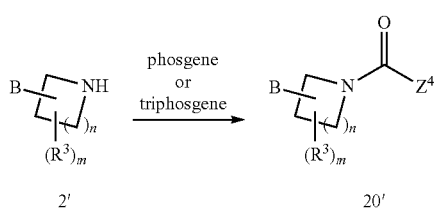

Analytical Methods

Method 1 [LC-MS (3 min)]
Column: Chromolith SpeedRod, RP-18e, 50×4.6 mm; Mobil phase: A: 0.01% TFA/water, B: 0.01% TFA/$CH_3CN$; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

LC-MS Method 2 (16 min)
Column: Chromolith SpeedRod, RP-18e, 50×4.6 mm; Mobil phase: A: 0.01% TFA/water, B: 0.01% TFA/$CH_3CN$; Flow rate: 1 mL/min; Gradient:

| Time (min) | A % | B % |
| --- | --- | --- |
| 0.0 | 90 | 10 |
| 14.0 | 10 | 90 |
| 15.0 | 10 | 90 |
| 15.1 | 90 | 10 |
| 16.0 | 90 | 10 |

LC-MS Method 3 (10-80)

| Column | YMC-PACK ODS-AQ, 50 × 2.0 mm 5 μm | | |
| --- | --- | --- | --- |
| Mobile Phase | A: water (4 L) + TFA (1.5 mL))<br>B: acetonitrile (4 L) + TFA (0.75 mL)) | | |
| | TIME(min) | A % | B % |
| | 0 | 90 | 10 |
| | 2.2 | 20 | 80 |
| | 2.5 | 20 | 80 |
| Flow Rate | 1 mL/min | | |
| Wavelength | UV 220 nm | | |
| Oven Temp | 50° C. | | |
| MS ionization | ESI | | |

LC-MS Method 4

| column | StableBond SB-C18 30 × 4.6 mm, 1.8 μm | | |
| --- | --- | --- | --- |
| mobile phase | A: water + 0.1% F$_3$CCO$_2$H<br>B: methanol | | |
| | TIME (min) | A % | B % |
| | 0.00 | 90 | 10 |
| | 1.80 | 0 | 100 |
| | 2.00 | 0 | 100 |
| | 2.15 | 90 | 10 |
| | 2.35 | 90 | 10 |
| flow rate | 1.75 mL/min | | |
| wavelength | UV 220, 230, or 254 nm | | |

Preparation 1

1-(methoxycarbonyl)-4-adamantyl chloroformate

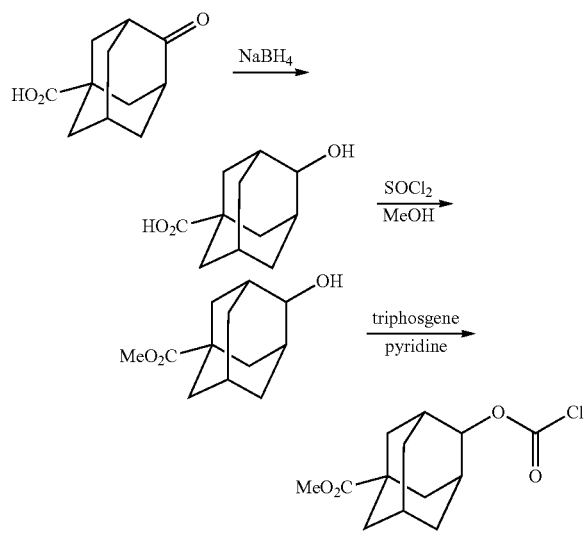

Step 1

To a stirred solution of 4-oxoadamantane-1-carboxylic acid (2.09 g, 10.8 mmol), in MeOH (100 mL), powdered NaBH$_4$ (815 mg, 21.5 mmol) was added cautiously in three portions. The mixture was stirred at rt for 1 h and concentrated under reduced pressure to remove the bulk of the methanol. The residue was diluted with 5% aq HCl (75 mL) and extracted with ether (2×100 mL). The combined ether extracts were washed with brine (25 mL) and dried over MgSO$_4$. Removal of the solvent left crude 4-hydroxy-1-adamantanecarboxylic acid (2.36 g, quant) as a white solid.

Step 2

MeOH (50 mL) was stirred and cooled in an ice bath and SOCl$_2$ (3 mL, 42 mmol) was added dropwise. The mixture was stirred for 15 min and added to a stirred suspension of crude 4-hydroxy-1-adamantanecarboxylic acid (2.36 g, 12.0 mmol) in MeOH (10 mL). The mixture was stirred overnight at rt and concentrated to leave an oil (2.46 g). Chromatography on a 40-g silica gel cartridge eluted with a gradient from 0-80% EtOAc in hexanes afforded methyl 4-hydroxyadamantane-1-carboxylate (1.88 g, 74%).

Step 3

A stirred solution of methyl 4-hydroxyadamantane-1-carboxylate (1.01 g, 4.8 mmol) and pyridine (0.38 mL, 4.8 mmol) in CH$_2$Cl$_2$ (25 mL) was cooled in an ice bath and a solution of triphosgene (0.48 g, 1.6 mmol) in CH$_2$Cl$_2$ (10 mL) was added dropwise over 15 min. The ice bath was allowed to melt and the mixture was stirred for 3 h at rt.* The mixture was evaporated to dryness and the residue was triturated with EtOAc (100 mL). The filtrate was concentrated to afford 1-(methoxycarbonyl)-4-adamantyl chloroformate (1.19 g, 91%) as an oil.

[* In some experiments the solution of 1-(methoxycarbonyl)-4-adamantyl chloroformate was used directly.]

Preparation 2

1-hydroxy-4-adamantyl chloroformate

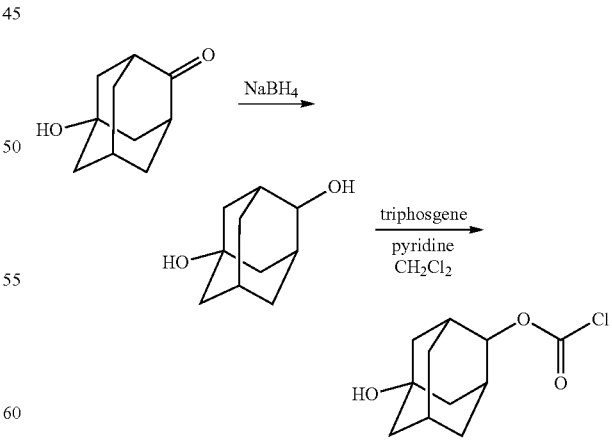

Step 1

A stirred solution of 1-hydroxy-4-adamantanone (10.53 g, 63.4 mmol) in MeOH (100 mL) was cooled in an ice bath and NaBH₄ (5×1-g caplets, 5.0 g, 130 mmol) was added. The ice bath was allowed to melt and the mixture was stirred overnight. 5% aq HCl (25 mL) was added and the mixture was concentrated to leave a white solid. This material was suspended in EtOAc (350 mL) and 5% aq HCl (100 mL) and filtered. The organic layer of the filtrate was collected, washed with brine, dried over Na₂SO₄ and concentrated to afford 1,4-adamantanediol (4.47 g, 41%).

Step 2

A solution of 1,4-adamantanediol (210 mg, 1.25 mmol) in dry pyridine (3 mL) and dry CH₂Cl₂ (6 mL) was cooled in an ice bath and a solution of triphosgene (122 mg, 0.41 mmol) in dry Ch2Cl2 (3 mL) was added dropwise over 5 min. The mixture was stirred in the ice bath for 3 h to afford a 0.1 M solution of 1-hydroxy-4-adamantyl chloroformate.

Preparation 3

2-Adamantyl chloroformate

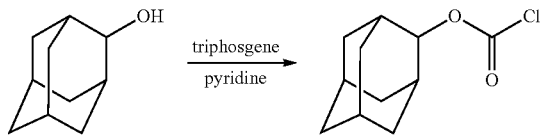 [SMILES: OC1C2CC3CC(C2)CC1C3 ; O=C(Cl)OC1C2CC3CC(C2)CC1C3]

The title compound was prepared from 2-adamantanol as disclosed in U.S. Pat. No. 5,270,302, Example 74, Step (a), the contents of which are hereby incorporated by reference.

Preparation 4

1-methyl-6-(pyrrolidin-3-yl)quinolin-2(1H)-one

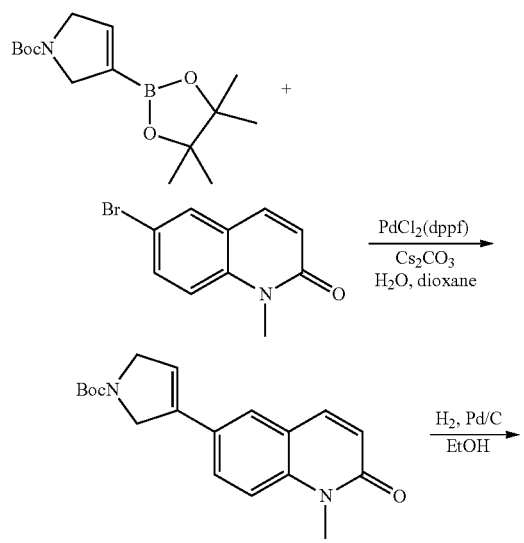

-continued

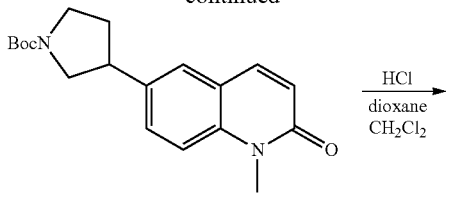

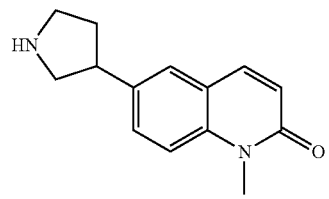

Step 1

A microwave vial equipped with a flea stirbar was charged with tert-butyl 3-(4,4,5,5-tetramethyl-1,3,2-dioxaborolan-2-yl)-2,5-dihydro-1H-pyrrole-1-carboxylate (107 mg, 0.36 mmol), 6-bromo-1-methylquinolin-2(1H)-one (104 mg, 0.44 mmol), Cs₂CO₃ (236 mg, 0.73 mmol), H₂O (0.15 mL) and dry dioxane (1.5 mL). The mixture was sparged with N₂ for 5 min and PdCl₂(dppf) (22 mg, 0.03 mmol) was added. The mixture was sparged with N₂ for 5 min and heated at 110 C in the microwave for 1 h. The mixture was diluted with MeOH (1 mL) and 5% aq HCl (0.1 mL), filtered and purified by prep HPLC to afford an oil (43 mg). This material was applied to a 2-g silica gel SPE cartridge and eluted sequentially with 0, 25, 50, 75 and 100% EtOAc in hexanes (15 mL of each) to afford five fractions. Fractions 3-5 were pooled and concentrated to afford tert-butyl 3-(1-methyl-2-oxo-1,2-dihydroquinolin-6-yl)-2,5-dihydro-1H-pyrrole-1-carboxylate (19 mg, 16%). LC-MS Method 1 $t_R$=1.70 min, m/z=327.

Step 2

To a stirred solution of tert-butyl 3-(1-methyl-2-oxo-1,2-dihydroquinolin-6-yl)-2,5-dihydro-1H-pyrrole-1-carboxylate (19 mg, 0.088 mmol) in EtOH (5 mL) was added 10% Pd on C (cat qty). The mixture was stirred under 1 atm of H₂ for 2 h. The mixture was filtered through Celite and the filtrate was concentrated to leave a brown oil (16.6 mg). Prep HPLC afforded tert-butyl 3-(1-methyl-2-oxo-1,2-dihydroquinolin-6-yl)pyrrolidine-1-carboxylate (1 mg, 5%). LC-MS Method 1 $t_R$=1.65 min, m/z=329.

Step 3

A stirred solution of tert-butyl 3-(1-methyl-2-oxo-1,2-dihydroquinolin-6-yl)pyrrolidine-1-carboxylate (1 mg) in CH₂Cl₂ (2 mL) was treated with 4 M HCl in dioxane (1 mL, 4 mmol). The mixture was stirred at rt for 3 h and concentrated to leave 1-methyl-6-(pyrrolidin-3-yl)quinolin-2(1H)-one as its HCl salt (1 mg). LC-MS Method 1 $t_R$=1.48 min, m/z=229.

Preparation 5

(R)-6-chloro-1-methyl-3-(pyrrolidin-3-yl)-1H-imidazo[4,5-b]pyridin-2(3H)-one

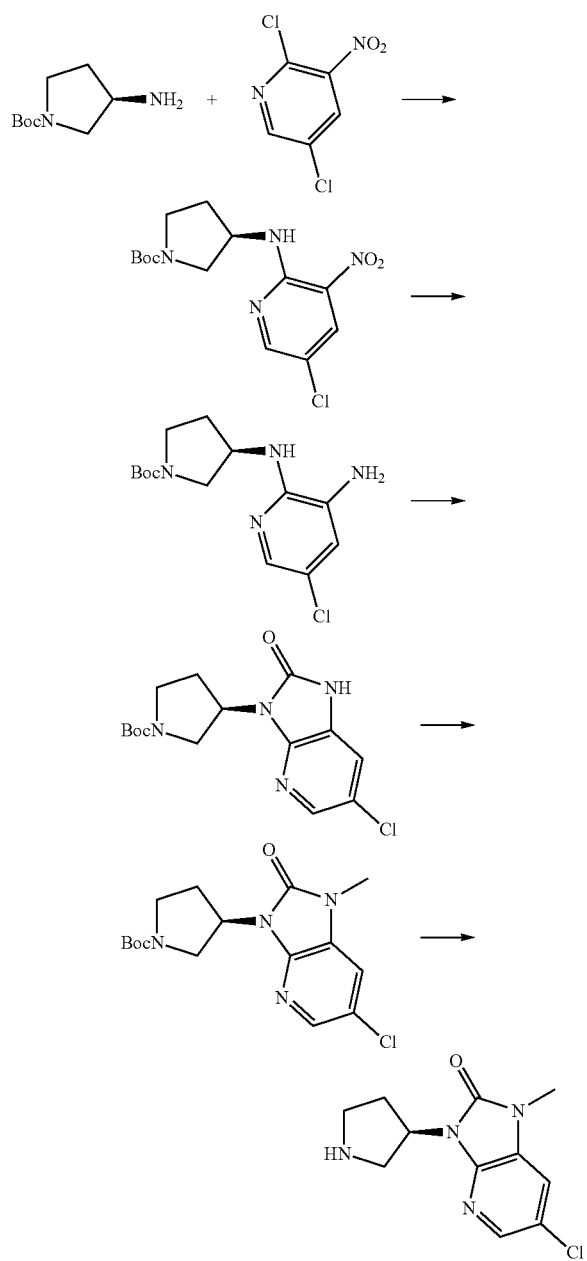

Step 1

A heavy-walled glass tube was charged with (R)-tert-butyl 3-aminopyrrolidine-1-carboxylate (1.35 g, 7.15 mmol), 2,5-dichloro-3-nitropyridine (1.04 g, 5.4 mmol), i-Pr$_2$NEt (2.6 mL, 14.3 mmol) and n-PrOH (10 mL). The tube was sealed and the mixture was heated and stirred at 120° C. in an oil bath for 3 h. The mixture was concentrated and the residue was taken up in EtOAc (200 mL), washed with 1% aq HCl (2×40 mL), satd aq NaHCO$_3$ (40 mL) and brine (40 mL), and dried over Na$_2$SO$_4$. Removal of the solvent afforded a brown oil (1.91 g) which was chromatographed a 40-g silica cartridge eluted with a 0-50% EtOAc in hexanes gradient to afford (R)-tert-butyl 3-(5-chloro-3-nitropyridin-2-ylamino)pyrrolidine-1-carboxylate (1.57 g, 85%) as a yellow oil. LC-MS Method 1 $t_R$=2.05 min, m/z=343, 287.

Step 2

To a stirred solution of (R)-tert-butyl 3-(5-chloro-3-nitropyridin-2-ylamino)pyrrolidine-1-carboxylate (802 mg, 2.34 mmol) in MeOH (25 mL) and water (25 mL) were added iron dust (2.00 g, 35 mmol) and NH$_4$Cl (1.25 g, 2.4 mmol). The mixture was heated at reflux for 6 h and filtered through Celite, washing with EtOAc. The filtrate was concentrated and the residue was dissolved in CH$_2$Cl$_2$ (150 mL) and 1 M aq NaOH (50 mL). The layers were separated and the aqueous layer was extracted with CH$_2$Cl$_2$ (50 mL). The combined CH$_2$Cl$_2$ layer was washed with brine (50 mL), dried over Na$_2$SO$_4$ and concentrated to leave (R)-tert-butyl 3-(3-amino-5-chloropyridin-2-ylamino)pyrrolidine-1-carboxylate (680 mg, 93%) as a black solid. LC-MS Method 1 $t_R$=1.28 min, m/z=313, 257.

Step 3

A stirred solution of (R)-tert-butyl 3-(3-amino-5-chloropyridin-2-ylamino)pyrrolidine-1-carboxylate (680 mg, 2.2 mmol) and i-Pr$_2$NEt (1.2 mL, 6.6 mmol0 in CH$_2$Cl$_2$ (50 mL) was cooled in an ice bath and solid triphosgene (213 mg, 0.72 mmol) was added. The ice bath was allowed to melt and the mixture was stirred overnight at rt. The mixture was concentrated to leave a black solid which was purified by chromatography on a 12-g silica cartridge eluted with a 0-100% EtOAc in hexanes gradient to afford (R)-tert-butyl 3-(6-chloro-2-oxo-1H-imidazo[4,5-b]pyridin-3(2H)-yl)pyrrolidine-1-carboxylate (461 mg, 62%) as a black solid. LC-MS Method 1 $t_R$=1.65 min, m/z=339, 283.

Step 4

To a stirred solution of (R)-tert-butyl 3-(6-chloro-2-oxo-1H-imidazo[4,5-b]pyridin-3(2H)-yl)pyrrolidine-1-carboxylate (110 mg, 0.33 mmol) in dry THF (5 mL) was added 60% NaH in oil (20 mg, 0.5 mmol). The mixture was stirred at rt for 5 min and MeI (0.02 mL, 0.33 mmol) was added. The mixture was stirred overnight, diluted with EtOAc (100 mL), washed with brine (2×10 mL) and dried over Na$_2$SO$_4$. Removal of the solvent left an oil (118 mg) which was applied to a 2-g silica SPE cartridge. The cartridge was eluted sequentially with 0, 25, 50, 75 and 100% EtOAc in hexanes (15 mL of each) to afford 5 fractions. Fractions 2 & 3 were pooled and concentrated to give (R)-tert-butyl 3-(6-chloro-1-methyl-2-oxo-1H-imidazo[4,5-b]pyridin-3(2H)-yl)pyrrolidine-1-carboxylate (109 mg, 95%) as a red oil. LC-MS Method 1 $t_R$=1.82 min, m/z=353, 279.

Step 5

(R)-tert-butyl 3-(6-chloro-1-methyl-2-oxo-1H-imidazo[4,5-b]pyridin-3(2H)-yl)pyrrolidine-1-carboxylate (109 mg) was dissolved in CH$_2$Cl$_2$ (3 mL) and 4 M HCl in dioxane (1 mL, 4 mmol) was added. The mixture was stirred at rt for 3 h and concentrated to give (R)-6-chloro-1-methyl-3-(pyrrolidin-3-yl)-1H-imidazo[4,5-b]pyridin-2(3H)-one as its HCl salt (78 mg, 87%). Method 1 $t_R$=0.77 min, m/z=253.

(R)-1-methyl-3-(pyrrolidin-3-yl)-1H-benzo[d]imidazol-2(3H)-one was prepared by following an analogous procedure using 2-fluoronitrobenzene in Step 1.

(R)-1-(pyrrolidin-3-yl)-1H-benzo[d]imidazol-2(3H)-one was prepared by following an analogous procedure using 2-fluoronitrobenzene in Step 1 and omitting Step 4.

(S)-1-(pyrrolidin-3-yl)-1H-benzo[d]imidazol-2(3H)-one was prepared by following an analogous procedure using (S)-tert-butyl 3-aminopyrrolidine-1-carboxylate and 2-fluoronitrobenzene in Step 1 and omitting Step 4.

(S)-5-fluoro-1-(pyrrolidin-3-yl)-1H-benzo[d]imidazol-2(3H)-one was prepared by following an analogous procedure using (S)-tert-butyl 3-aminopyrrolidine-1-carboxylate and 2,5-difluoronitrobenzene in Step 1 and omitting Step 4.

(S)-2-oxo-1-(pyrrolidin-3-yl)-2,3-dihydro-1H-benzo[d]imidazole-5-carbonitrile was prepared by following an analogous procedure using (S)-tert-butyl 3-aminopyrrolidine-1-carboxylate and 4-fluoro-3-nitrobenzonitrile in Step 1 and omitting Step 4.

(R)-2-oxo-3-(pyrrolidin-3-yl)-2,3-dihydro-1H-benzo[d]imidazole-5-carbonitrile was prepared by following an analogous procedure using 3-fluoro-4-nitrobenzonitrile in Step 1 and omitting Step 4.

(S)-7-chloro-1-(pyrrolidin-3-yl)-1H-benzo[d]imidazol-2(3H)-one was prepared by following an analogous procedure using (S)-tert-butyl 3-aminopyrrolidine-1-carboxylate and 2,6-dichloronitrobenzene in Step 1 and omitting Step 4.

(R)-7-chloro-1-(pyrrolidin-3-yl)-1H-benzo[d]imidazol-2(3H)-one was prepared by following an analogous procedure using 2,6-dichloronitrobenzene in Step 1 and omitting Step 4.

(R)-6-chloro-3-(pyrrolidin-3-yl)-1H-imidazo[4,5-b]pyridin-2(3H)-one was prepared as described above omitting Step 4.

(S)—N-(4-fluoro-2-nitrophenyl)pyrrolidin-3-amine was prepared following analogous procedures using 2,5-difluoronitrobenzene in Step 1 and omitting Steps 2, 3 and 4.

Preparation 6

1-methyl-2-(pyrrolidin-3-yl)-1H-benzo[d]imidazole

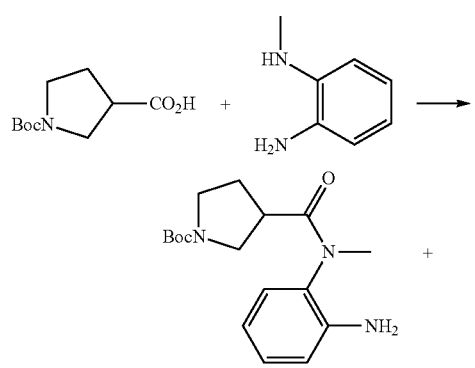

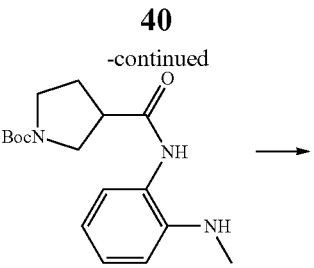

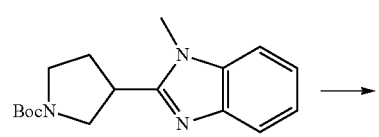

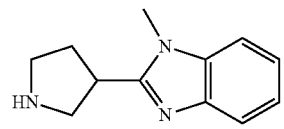

Step 1

To a stirred solution of 1-(tert-butoxycarbonyl)pyrrolidine-3-carboxylic acid (1.00 g, 4.65 mmol), N-methylphenylenediamine (570 mg, 4.65 mmol), i-Pr$_2$NEt (2.5 mL, 14.0 mmol) and CH$_2$Cl$_2$ (25 mL) was added solid HATU (1.95 g, 5.1 mmol). The mixture was stirred overnight and concentrated to leave a brown oil. This material was taken up in EtOAc (175 mL), washed with satd aq NaHCO$_3$ (50 mL) and brine (50 mL), and dried over Na$_2$SO$_4$. Removal of the solvent left a crude mixture of amide products (2.82 g) as a brown oil which was used directly in the next step. LC-MS Method 1 $t_R$=1.37 min, m/z=321.

Step 2

The crude product from Step 1 (2.82 g) was heated at 70° C. in glacial HOAc (80 mL) for 18 h. The mixture was concentrated. The residue was taken up in EtOAc (200 mL), washed with brine (30 mL), satd aq NaHCO$_3$ (2×30 mL) and brine (30 mL), and dried over Na$_2$SO$_4$. Removal of the solvent left a brown solid which was purified by chromatography on a 12-g silica gel cartridge eluted with a 0-100% EtOAc in hexanes gradient to give tert-butyl 3-(1-methyl-1H-benzo[d]imidazol-2-yl)pyrrolidine-1-carboxylate (93 mg). LC-MS Method 1 $t_R$=1.12 min, m/z=302.

Step 3 tert-Butyl 3-(1-methyl-1H-benzo[d]imidazol-2-yl)pyrrolidine-1-carboxylate (93 mg) was dissolved in CH$_2$Cl$_2$ (3 mL) and 4 M HCl in dioxane (1 mL) was added. The mixture was stirred at rt for 3 h and concentrated to leave 1-methyl-2-

(pyrrolidin-3-yl)-1H-benzo[d]imidazole (103 mg) as a red solid. LC-MS Method 1 $t_R$=0.40 min, m/z=202.

Preparation 7

1-hydroxy-4-adamantyl chloroformate

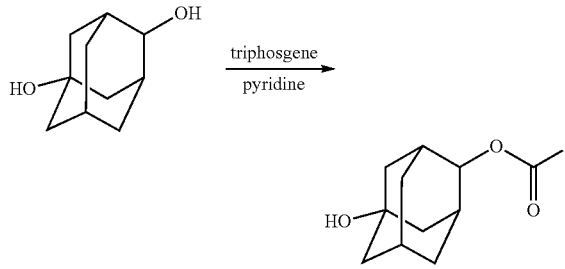

A stirred solution of 1,4-dihydroxyadamantane (1.69 g, 10.0 mmol) in dry pyridine (20 mL) and dry $CH_2Cl_2$ (60 mL) was cooled in an ice bath and a solution of triphosgene (0.98 g, 3.3 mmol) in dry $CH_2Cl_2$ (20 mL) was added dropwise over 15 min. The mixture was stirred in the ice bath for 3 h to give a 0.1 M solution of the title chloroformate which was used directly.

Preparation 8

2-methyl-1-(3-phenylpyrrolidin-3-yl)propan-2-ol

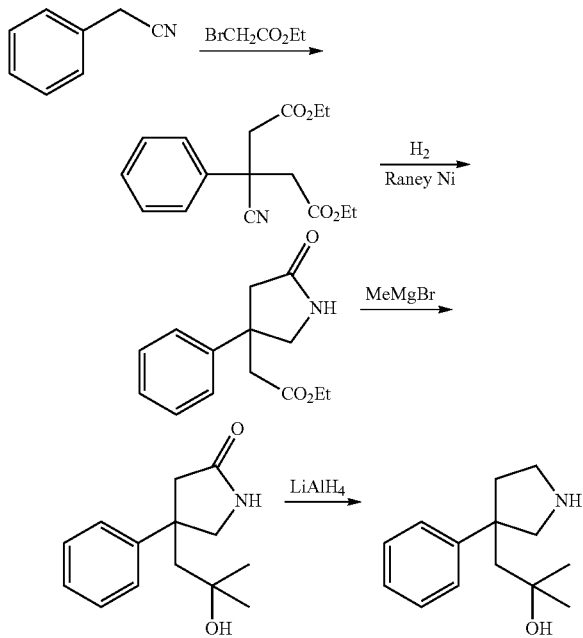

Step 1

To a solution of benzyl cyanide (11.7 g, 100 mmol) in anhydrous THF (100 mL) was added slowly the solution of LiHMDS in THF (1 M, 200 mL, 200 mmol) at −78° C. in a dry-ice/acetone bath. After addition, the mixture was warmed to rt, stirred for 1 h, cooled to −78° C., and added ethyl bromoacetate (32.9 g, 198 mmol) dropwise. After addition, the reaction mixture was stirred at rt overnight. When TLC showed that the benzyl cyanaide was consumed, the reaction mixture was quenched with satd aq $NH_4Cl$ (150 mL), and extracted with EtOAc (3×150 mL). The combined organic layers were washed with satd aq $NaHCO_3$ (150 mL) and brine (150 mL), dried over $Na_2SO_4$, and concentrated to give the crude final product, which was purified by chromatography on a silica gel column eluted with PE/EtOAc=50:1-10:1 to give diethyl 3-cyano-3-phenylpentanedioate (10.6 g, yield 37%) as brown oil. $^1$H NMR ($CDCl_3$ 400 MHz): δ 7.45 (d, 2H), 7.37 (t, 2H), 7.28 (t, 1H), 4.06 (q, 4H), 3.2 (m, 4H), 1.12 (t, 6H).

Step 2

A mixture of diethyl 3-cyano-3-phenylpentanedioate (8 g, 27.7 mmol) and Raney-Ni (4 g) in EtOH (240 mL) was stirred under $H_2$ atmosphere (50 psi) at rt for 2 days. TLC and LC-MS showed that the reaction was completed, the reaction mixture was filtered through Celite, and the filtrate was concentrated under reduced pressure to dryness. The residue was purified by chromatography on a silica gel column eluting with PE/EtOAc=10:1 1:8 to give ethyl 2-(5-oxo-3-phenylpyrrolidin-3-yl)acetate (4.8 g, yield 71%) as white solid. $^1$H NMR ($CDCl_3$ 400 MHz): δ 7.33 (t, 2H), 7.24 (t, 1H), 7.18 (d, 2H), 5.79 (s, 1H), 3.97-3.88 (m, 3H), 3.72 (d, 1H), 2.86-2.70 (m, 4H), 1.03 (t, 3H).

Step 3

To a solution of ethyl 2-(5-oxo-3-phenylpyrrolidin-3-yl) acetate (2.63 g, 10.6 mmol) in anhydrous THF (30 mL) was added dropwise the solution of MeMgBr in ether (3 M, 35.5 mL, 106 mmol) at −78° C. in a dry-ice/acetone bath. After addition, the reaction mixture was warmed to rt and stirred for 3 h, TLC showed that the starting material was consumed. The reaction mixture was diluted with satd aq $NH_4Cl$ (60 mL), and extracted with EtOAc (60 mL×3). The combined organic layers were washed with brine (50 mL), dried over $Na_2SO_4$, and concentrated to dryness to give crude 4-(2-hydroxy-2-methylpropyl)-4-phenylpyrrolidin-2-one (2.17 g, yield 87.5%), which was used directly for next step without purification. $^1$H NMR ($CDCl_3$ 400 MHz): δ 7.39-7.25 (m, 5H), 5.61 (s, br, 1H), 3.80-3.71 (m, 2H), 2.83 (s, 2H), 2.25-2.15 (m, 2H), 1.05 (s, 3H), 0.98 (s, 3H).

Step 5

To a solution of 4-(2-hydroxy-2-methylpropyl)-4-phenylpyrrolidin-2-one (crude, 2.17 g, 9.3 mmol) in anhydrous THF (40 mL) was added $LiAlH_4$ (1.42 g, 37.3 mmol) at −10° C. in a dry-ice/acetone bath. The reaction mixture was refluxed overnight. LC-MS showed that about 90% of desired product was produced. The reaction mixture was diluted with anhydrous THF (200 mL) and filtered through Celite. The filter cake was washed several times with anhydrous THF. The filtrate was concentrated to dryness to give crude 2-methyl-1-(3-phenylpyrrolidin-3-yl)propan-2-ol (1.34 g, 67%), which was used directly for next step without purification. $^1$H NMR ($CDCl_3$ 400 MHz): δ 7.28-7.22 (m, 4H), 7.16-7.12 (m, 1H), 3.82 (s, br, 1H), 3.24-3.16 (m, 2H), 3.11 (m, 1H), 2.95 (m, 1H), 2.26-2.13 (m, 2H), 1.98 (s, 2H), 1.09 (s, 3H), 1.05 (s, 3H).

Preparation 9

(R)-4-(pyridin-4-yl)-2-(pyrrolidin-2-yl)thiazole

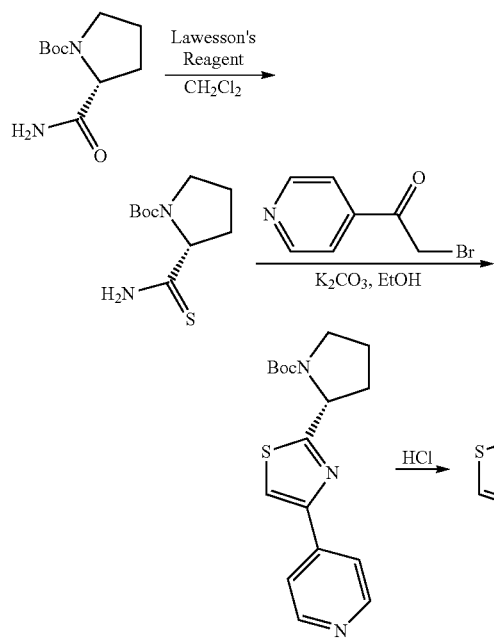

Step 1

To a stirred solution Boc-D-prolinamide (2.63 g, 12.3 mmol) in CH$_2$Cl$_2$ (25 mL) at rt was added Lawesson's reagent (2.73 g, 6.75 mmol). The mixture was stirred overnight and concentrated. The oily residue was purified by chromatography on a 40-g silica gel cartridge, eluted with a 0-20% MeOH in CH$_2$Cl$_2$ gradient, to afford (R)-tert-butyl 2-carbamothioylpyrrolidine-1-carboxylate (2.65 g, 94%) as a tan solid. LC-MS Method 1 $t_R$=1.23 min, m/z=231, 173, 131.

Step 2

A stirred mixture of (R)-tert-butyl 2-carbamothioylpyrrolidine-1-carboxylate (373 mg, 1.6 mmol), 4-(bromoacetyl)pyridine.HBr (455 mg, 1.6 mmol), K$_2$CO$_3$ (224 mg, 1.6 mmol) and EtOH (20 mL) was heated at reflux for 4 h. The mixture was cooled and concentrated. The residues was taken up in EtOAc (90 mL), washed with 0.5 M aq NaOH (20 mL) and brine (20 mL), and dried over Na$_2$SO$_4$. Removal of the solvent left an amber oil (410 mg). A 379-mg portion of the crude product was purified by chromatography on a 12-g silica gel cartridge, eluted with a 0-100% EtOAc in hexanes gradient to afford (R)-tert-butyl 2-(4-(pyridin-4-yl)thiazol-2-yl)pyrrolidine-1-carboxylate (200 mg, 37%) as a tan solid. LC-MS Method 1 $t_R$=1.20 min, m/z=332.

Step 3

A 31-mg aliquot of crude product from Step 2 was dissolved in CH$_2$Cl$_2$ (3 mL) and 4 M HCl in dioxane (1 mL) was added. The mixture was stirred at rt for 2 h and concentrated to leave (R)-4-(pyridin-4-yl)-2-(pyrrolidin-2-yl)thiazole as its HCl salt (35 mg). LC-MS Method 1 $t_R$=0.40 min, m/z=232.

4-(pyridin-4-yl)-2-(pyrrolidin-3-yl)thiazole was prepared from tert-butyl 3-carbamothioylpyrrolidine-1-carboxylate following procedures analogous to those described in Steps 2 and 3.

Preparation 10

(R)-1-methyl-4-(2-(pyrrolidin-2-yl)thiazol-4-yl)pyridin-2(1H)-one

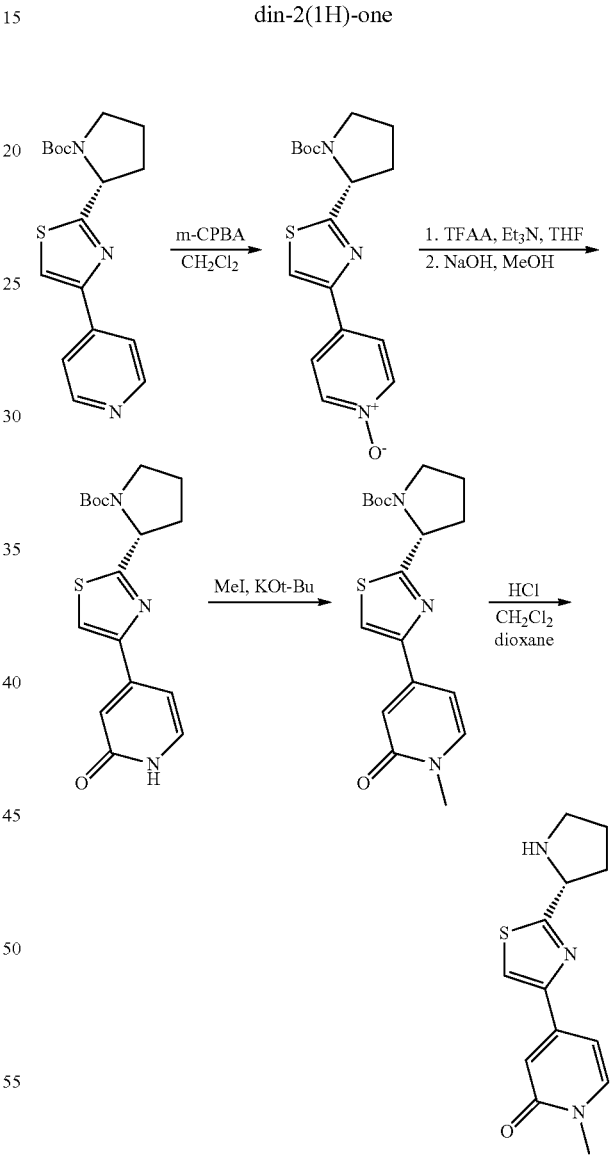

Step 1

To a stirred, ice-cold solution of (R)-tert-butyl 2-(4-(pyridin-4-yl)thiazol-2-yl)pyrrolidine-1-carboxylate (1.34 g, 4.0 mmol) in CH$_2$Cl$_2$ (40 mL) was added solid m-CPBA (≤77%, 1.00 g, ≤4.4 mmol). The ice bath was allowed to melt and the mixture was stirred overnight at rt. The mixture was diluted with CH$_2$Cl$_2$ (160 mL), washed with satd aq NaHCO$_3$ (20 mL) and brine (20 mL), and dried over Na$_2$SO$_4$. Removal of the solvent left a mixture of (R)-4-(2-(1-(tert-butoxycarbonyl)pyrrolidin-2-yl)thiazol-4-yl)pyridine 1-oxide and m-CPBA (1.70 g) which was used in the next step without purification. LC-MS Method 1 t$_R$=1.37 min, m/z=348.

Step 2

A stirred solution of crude (R)-4-(2-(1-(tert-butoxycarbonyl)pyrrolidin-2-yl)thiazol-4-yl)pyridine 1-oxide (890 mg, 2.6 mmol) from Step 1 and Et$_3$N (2.15 mL, 15.4 mmol) in dry THF (10 mL) was cooled in an ice bath and trifluoroacetic anhydride (1.05 mL, 7.7 mmol) was added. The mixture was allowed to warm to rt and stirred for 4 h. MeOH (10 mL) and 2 M aq NaOH (10 mL) were added. The mixture was stirred over the weekend and concentrated to remove THF and MeOH. The aqueous residue was acidified with 5% aq HCl (20 mL) and extracted with EtOAc (150 mL). The organic layer was washed with brine (25 mL), dried over Na$_2$SO$_4$ and concentrated to leave a sticky brown solid (1.67 g). Chromatography on a 12-g silica gel cartridge eluted with EtOAc, followed by a 0-25% MeOH in EtOAc gradient to afford (R)-tert-butyl 2-(4-(2-oxo-1,2-dihydropyridin-4-yl)thiazol-2-yl)pyrrolidine-1-carboxylate (318 mg, 36%) as an oil. LC-MS Method 1 t$_R$=1.35 min, m/z=348, 292.

Step 3

To a stirred, ice-cold solution of (R)-tert-butyl 2-(4-(2-oxo-1,2-dihydropyridin-4-yl)thiazol-2-yl)pyrrolidine-1-carboxylate (318 mg, 0.92 mmol) in dry THF (10 mL) was added solid KOt-Bu (98 mg, 0.87 mmol). The mixture was stirred in the ice bath for 10 min and MeI (0.055 mL, 0.87 mmol) was added. The mixture was stirred at rt for 20 h and concentrated. The residue was taken up in EtOAc (100 mL), washed with satd aq NaHCO$_3$ (2×10 mL) and brine (10 mL), and dried over Na$_2$SO$_4$. Removal of the solvent left a brown syrup (275 mg) which was purified by chromatogarphy on a 12-g silica gel cartridge eluted with EtOAc, followed by a 0-20% MeOH in EtOAc gradient to afford recovered starting material (61 mg, 19%) and (R)-tert-butyl 2-(4-(1-methyl-2-oxo-1,2-dihydropyridin-4-yl)thiazol-2-yl)pyrrolidine-1-carboxylate (131 mg, 40%). LC-MS Method 1 t$_R$=1.47 min, m/z=362.

Step 4

(R)-tert-butyl 2-(4-(1-methyl-2-oxo-1,2-dihydropyridin-4-yl)thiazol-2-yl)pyrrolidine-1-carboxylate (131 mg,) was dissolved in CH$_2$Cl$_2$ (5 mL) and 4 M HCl in dioxane (5 mL) was added. The mixture was stirred at rt for 3 h and concentrated to afford (R)-1-methyl-4-(2-(pyrrolidin-2-yl)thiazol-4-yl)pyridin-2(1H)-one HCl salt (127 mg) as an off-white solid. LC-MS Method 1 t$_R$=0.40 min, m/z=262.

(R)-4-(2-(pyrrolidin-2-yl)thiazol-4-yl)pyridin-2(1H)-one was prepared following an analogous procedure omitting Step 3.

1-methyl-4-(2-(pyrrolidin-3-yl)thiazol-4-yl)pyridin-2 (1H)-one was prepared following an analogous procedure starting with 4-(pyridin-4-yl)-2-(pyrrolidin-3-yl)thiazole.

Preparation 11

(R)-7-chloro-2-methyl-1-(pyrrolidin-3-yl)-1H-benzo [d]imidazole

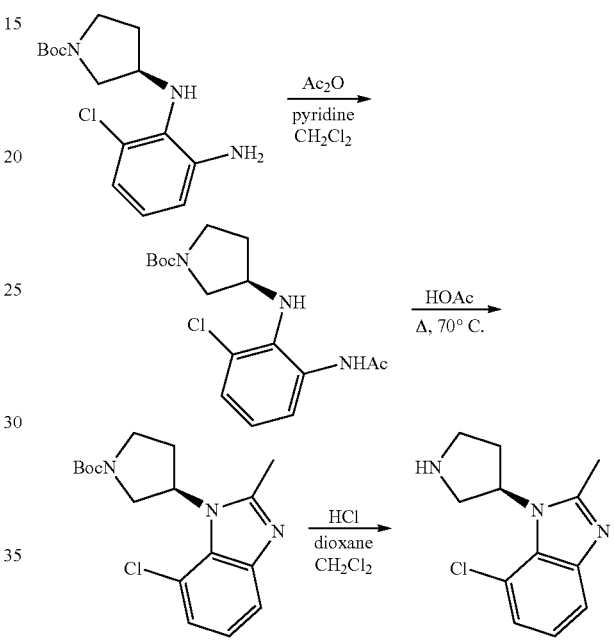

Step 1

To a stirred solution of (R)-tert-butyl 3-((2-amino-6-chlorophenyl)amino)pyrrolidine-1-carboxylate (135 mg, 0.43 mmol), prepared from (R)-tert-butyl 3-aminopyrrolidine-1-carboxylate and 2,6-dichloronitrobenzene as described in Preparation 6 Steps 1 and 2, and pyridine (0.105 mL, 1.4 mmol) in CH$_2$Cl$_2$ (3 mL) was added acetic anhydride (0.045 mL, 0.48 mmol). The mixture was stirred at rt overnight, diluted with EtOAc (100 mL), washed with water (10 mL) and brine (10 mL), and dried over Na$_2$SO$_4$. Removal of the solvent left crude (R)-tert-butyl 3-((2-acetamido-6-chlorophenyl)amino)pyrrolidine-1-carboxylate (148 mg, 96%) as a brown oil, which was used without purification in the next step. LC-MS Method 1 t$_R$=1.67 min, m/z=354, 298.

Step 2

Crude (R)-tert-butyl 3-((2-acetamido-6-chlorophenyl) amino)pyrrolidine-1-carboxylate (148 mg) was dissolved in glacial HOAc (20 mL) and heated at 70° C. for 1 day. The mixture was concentrated. The residue was taken up in EtOAc (100 mL), washed with satd aq NaHCO$_3$ (10 mL) and brine (10 mL), and dried over Na$_2$SO$_4$. Removal of the solvent left a brown oil (133 mg) which was purified by chromatography on a 12-g silica gel cartridge eluted with a 0-100% EtOAc in hexanes gradient to afford (R)-tert-butyl 3-(7-chloro-2-methyl-1H-benzo[d]imidazol-1-yl)pyrrolidine-1-carboxylate (59 mg, 18%) as a brown oil. LC-MS Method 1 $t_R$=1.42 min, m/z=336.

Step 3

(R)-tert-butyl 3-(7-chloro-2-methyl-1H-benzo[d]imidazol-1-yl)pyrrolidine-1-carboxylate was converted to the title compound as described in Preparation 6 Step 5.

(S)-7-chloro-2-methyl-1-(pyrrolidin-3-yl)-1H-benzo[d]imidazole was prepared following a procedure analogous to that described above using tert-butyl 3-((2-amino-6-chlorophenyl)amino)pyrrolidine-1-carboxylate in Step 1.

(S)-2-methyl-1-(pyrrolidin-3-yl)-1H-benzo[d]imidazole-5-carbonitrile was prepared following a procedure analogous to that described above using (S)-tert-butyl 3-((2-amino-4-cyanophenyl)amino)pyrrolidine-1-carboxylate in Step 1.

Preparation 12

5-methyl-2-(pyrrolidin-3-yl)pyridine

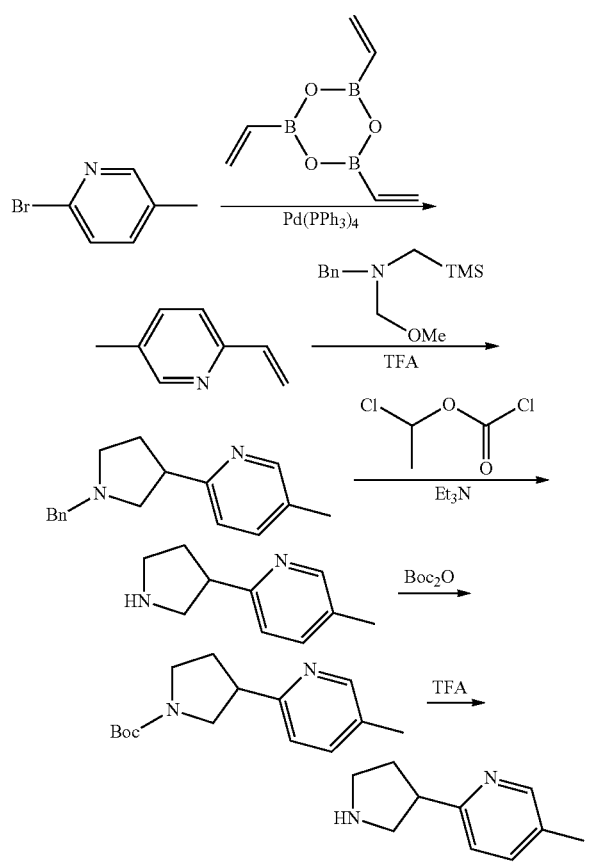

Step 1

To a stirred mixture of 2-bromo-5-methyl-pyridine (1.7 g, 10 mmol), 2,4,6-trivinyl-cyclotriboroxanein (1.20 g, 5 mmol) and $Na_2CO_3$ (3.73 g, 35.2 mmol) in toluene (15 mL)/EtOH (10 mL)/$H_2O$ (5 mL) was added $Pd(PPh_3)_4$ (300 mg, 0.25 mmol) under $N_2$. The mixture was stirred at 100° C. overnight. The resulting mixture was quenched with water (20 mL) and extracted with EtOAc (30 mL×3). The combined organic layers were washed with water (50 mL) and brine (50 mL), dried over $Na_2SO_4$ and concentrated. The residue was purified by chromatography column (PE:EA=50:1) to afford 5-methyl-2-vinyl-pyridine (900 mg, 75.6%) as a yellow oil.

Step 2

To a stirred solution of 5-methyl-2-vinylpyridine (600 mg, 1.87 mmol) in dry $CH_2Cl_2$ (6 mL) was added N-benzyl-1-methoxy-N-((trimethylsilyl)methyl)methanamine (1.42 g, 6.0 mmol) and TFA (570 mg, 5.0 mmol) at 0° C. The mixture was stirred at rt for 2 TLC showed the disappearance of starting material. The mixture was quenched with satd aq $NaHCO_3$ (15 mL) and extracted with EtOAc (30 mL×3). The combined organic layers were washed with water (40 mL) and brine (50 mL), dried over $Na_2SO_4$ and concentrated. The residue was purified by chromatography column on silica cartridge eluted with PE/EA=5:1 to afford 2-(1-benzyl-pyrolidin-3-yl)-5-methyl-pyridine (450 mg, 35%) as a yellow oil Step 3

To a stirred solution of 2-(1-benzylpyrrolidin-3-yl)-5-methylpyridine (200 mg, 0.79 mmol) in dry $CH_2Cl_2$ (3 mL) were added $Et_3N$ (80 mg, 0.79 mmol) and 1-chloroethyl carbonochloridate (225 mg, 1.6 mmol) at 0° C. The mixture was stirred at 0° C. for 2 h. The reaction mixture was concentrated under vacuum and dissolved in $CH_2Cl_2$ (5 mL). The organic solution was washed with water (20 mL×3), and the combined aqueous layers were concentrated to give crude 5-methyl-2-(pyrrolidin-3-yl)pyridine (150 mg, 82%) as a solid, which was used for next step without purification.

Step 4

To a stirred solution of crude 5-methyl-2-(pyrrolidin-3-yl)pyridine (200 mg, 1.24 mmol) in dry $CH_2Cl_2$ (4 mL) was added $(Boc)_2O$ (432 mg, 2.0 mmol) and $Et_3N$ (300 mg, 3 mmol) at 0° C. The mixture was stirred at rt for 1 h. TLC showed disappearance of starting material. The mixture was quenched with water (20 mL) and extracted with EtOAc (30 mL×3). The combined organic layer was washed with water (10 mL) and brine (10 mL), dried over $Na_2SO_4$ and concentrated. The residue was purified by preparative TLC (PE/EA=1:1) to afford tert-butyl 3-(5-methylpyridin-2-yl)pyrrolidine-1-carboxylate (85 mg, 26%) as a yellow oil.

Step 5

To a stirred solution of tert-butyl 3-(5-methylpyridin-2-yl)pyrrolidine-1-carboxylate (260 mg, 1.0 mmol) in dry $CH_2Cl_2$ (3 mL) was added TFA (2 mL, 20% in $CH_2Cl_2$) dropwise at 0° C. The reaction mixture was stirred at rt for 3 h. TLC showed the disappearance of starting material. The reaction mixture was concentrated under vacuum to afford crude 5-methyl-2-(pyrrolidin-3-yl)pyridine (170 mg, 96%), which was used for the next step without purification.

The following compounds were prepared following procedures analogous to those described above:

2-methyl-5-(pyrrolidin-3-yl)pyridine using 5-bromo-2-chloropyrimidine in Step 1.

3-methyl-6-(pyrrolidin-3-yl)pyridazine using 3-chloro-6-methylpyridazine in Step 1.

4-methyl-2-(pyrrolidin-3-yl)pyrimidine using 2-chloro-4-methylpyrimidine in Step 1.

5-methyl-2-(pyrrolidin-3-yl)pyrimidine using 2-chloro-5-methylpyrimidine in Step 1.

5-fluoro-2-(pyrrolidin-3-yl)pyrimidine using 2-chloro-5-fluoropyrimidine in Step 1.

4,6-dimethyl-2-(pyrrolidin-3-yl)pyrimidine using 2-chloro-4,4-dimethylpyrimidine in Step 1.

2-(pyrrolidin-3-yl)-4-(trifluoromethyl)pyrimidine using 2-chloro-4-(trifluoromethyl)pyrimidine in Step 1.

Preparation 13

1,5-dimethyl-3-(pyrrolidin-3-yl)-1H-pyrazole

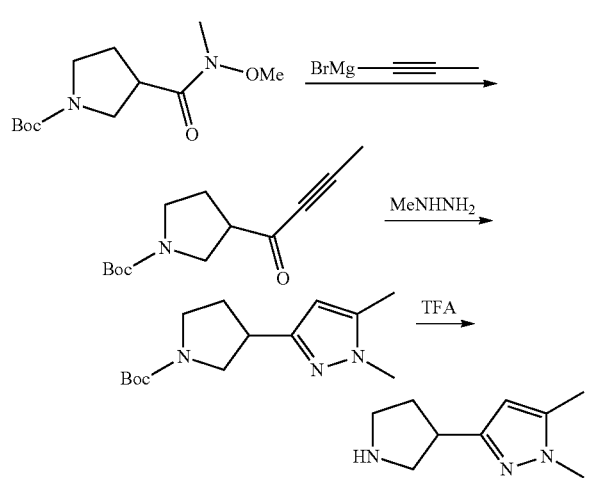

Step 1

To a stirred mixture of tert-butyl 3-(methoxy(methyl)carbamoyl)pyrrolidine-1-carboxylate (2 g, 7.75 mmol) in dry THF (10 mL) was added 1-propynylmagnesinm bromide (30 mL, 15 mmol) under $N_2$ at −78° C. The reaction mixture was stirred at −78° C. for 0.5 h, allowed to warm to rt slowly and stirred for another 10 h. The mixture was quenched with 2 N aq HCl (20 mL) at 0° C. and extracted with EtOAc (50 mL×3). The combined organic layers were washed with water (20 mL) and brine (20 mL), dried over $Na_2SO_4$ and concentrated. The residue was purified by preparative TLC (PE/EA=1:1) to afford tert-butyl 3-(but-2-ynoyl)pyrrolidine-1-carboxylate (1.6 g, 86%) as a white oil.

Step 2

To a stirred solution of 3-(1-oxo-but-2-ynyl)-pyrrolidine-1-carboxylic acid tert-butyl ester (0.8 g, 3.4 mmol) in MeOH (20 mL) was added methyl-hydrazine (5 g, 44 mmol). The mixture was stirred at room temperature for 10 hours. The reaction mixture was quenched with water (50 mL) and extracted with $CH_2Cl_2$ (50 mL×3). The combined organic layers were washed with water (30 mL) and brine (30 mL), dried over $Na_2SO_4$ and concentrated. The residue was purified by preparative TLC (PE/EA=1:1) to afford 3-(1,5-dimethyl-1H-pyrazol-3-yl)-pyrrolidine-1-carboxylic acid tert-butyl ester (800 mg, 88%) as white solid.

Step 3

To a stirred solution of 3-(1,5-dimethyl-1H-pyrazol-3-yl)-pyrrolidine-1-carboxylic acid tert-butyl ester (50 mg, 0.19 mmol) in dry $CH_2Cl_2$ (1 mL) was added TFA (2 mL, 20% in $CH_2Cl_2$) at 0° C. The reaction mixture was stirred at room temperature for 3 h. TLC showed the disappearance of starting material. The reaction mixture was concentrated in vacuum to afford crude 1,5-dimethyl-3-pyrrolidin-3-yl-1H-pyrazole (33 mg, 91%), which was used for the next step without purified.

Preparation 14

4-methyl-2-(pyrrolidin-3-yl)thiazole

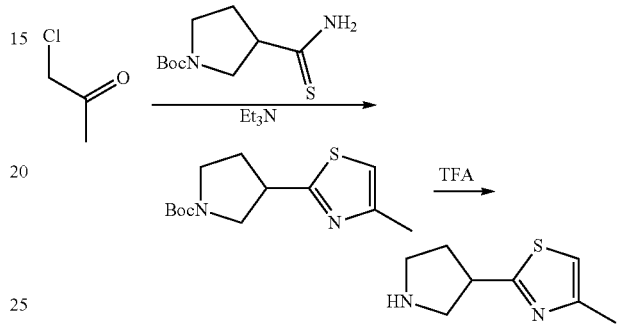

To a stirred solution of tert-butyl 3-carbamothioylpyrrolidine-1-carboxylate (100 mg, 0.44 mmol) in dry dioxane (1 mL) was added 1-chloropropan-2-one (80 mg, 0.87 mmol) and triethylamine (132 mg, 1.31 mmol). The mixture was stirred at room temperature for over night and refluxed for overnight. The reaction mixture was added EtOAc (10 mL), washed with water (5 mL×3) and brine (5 mL), dried over $Na_2SO_4$, filtered, concentrated and purified by preparative TLC (PE:EA=1:1) to give tert-butyl 3-(4-methylthiazol-2-yl)pyrrolidine-1-carboxylate (90 mg, 75%) as a yellow oil.

Step 2

To a solution of tert-butyl 3-(4-methylthiazol-2-yl)pyrrolidine-1-carboxylate (90 mg, 0.34 mmol) in $TFA/CH_2Cl_2$ (20%, 2 mL) was stirred at rt for 1 h and concentrated to give 4-methyl-2-(pyrrolidin-3-yl)thiazole (55 mg, 98%) as a yellow oil.

Preparation 14

5-bromo-2-(pyrrolidin-3-yl)pyrimidine

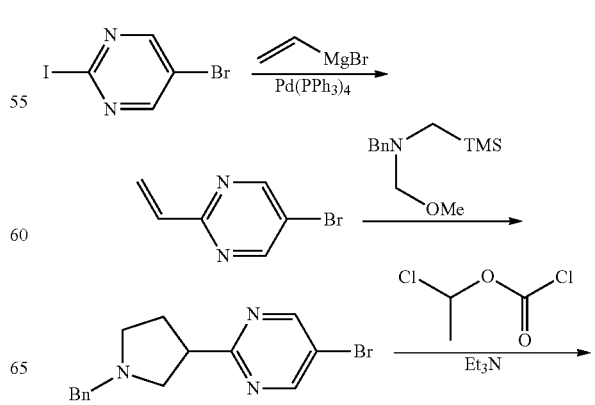

51

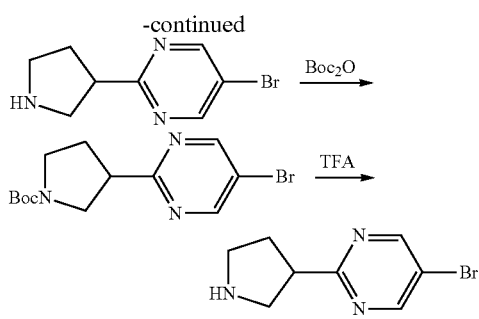

Step 1

To a solution of 5-bromo-2-iodopyrimidine (14.2 g, 50 mmol) and Pd(PPh₃)₄ (865 mg, 0.75 mmol) in THF (200 mL) at room temperature under nitrogen was added dropwise vinylmagnesium bromide (100 mL, 100 mmol, 1 M in THF). The reaction mixture was heated to reflux for 2 hours. The formed mixture was quenched with water (200 mL) and extracted with EtOAc (200 mL×3). The combined organic layers were dried over sodium sulfate, filtered and concentrated to afford an oil which was purified by preparative column chromatography to afford 5-bromo-2-vinylpyrimidine (8 g, yield: 86%).

Steps 2-5

Procedures analogous to those described in Preparation 12 Steps 2-5 were employed.

Preparation 15

5-methoxy-2-(pyrrolidin-3-yl)pyrimidine

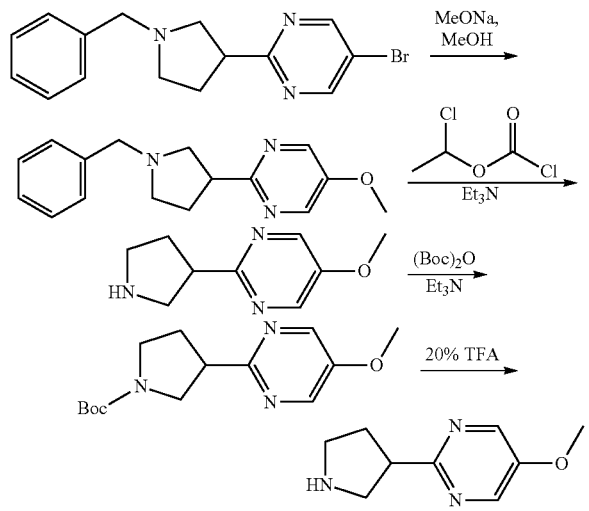

Step 1

Sodium (362 mg, 15.75 mmol) was added portionwise to methanol (15 mL) at 22° C. until a homogeneous solution was obtained. The solution was then treated with 2-(1-benzyl-pyrrolidin-3-yl)-5-bromo-pyrimidine (1 g, 3.15 mmol) and heated in a sealed tube at 110° C. for 24 h. The mixture was cooled, concentrated in vacuo. The residue was purified by column chromatography to afford 2-(1-benzylpyrrolidin-3-yl)-5-methoxypyrimidine (230 mg 27.2%) as a yellow oil.

Step 2

To a solution of 2-(1-benzyl-pyrrolidin-3-yl)-5-methoxy-pyrimidine (100 mg, 0.37 mmol) and Et₃N (37.6 mg, 0.37 mmol) in CH₂Cl₂ (2 mL) was added 1-chloroethyl carbonochloridate (63.8 mg, 0.45 mmol) dropwise at 0° C. The mixture was stirred at rt for 2 h. The reaction mixture was concentrated to afford crude 5-methoxy-2-(pyrrolidin-3-yl)pyrimidine (100 mg), which was used for next step without purification.

Step 3

To a stirred solution of 5-methoxy-2-(pyrrolidin-3-yl)pyrimidine (210 mg, 1.17 mmol) in dry CH₂Cl₂ (4 mL) was added Et₃N (354.5 mg, 3.51 mmol) and (Boc)₂O (529 mg, 2.34 mmol) dropwise at 0° C. The mixture was stirred at rt for 2 h. TLC showed the disappearance of starting material. The reaction mixture was washed with water (10 mL×3), and the combined organic layer was concentrated to give crude product, which was purified by prep TLC to give tert-butyl 3-(5-methoxypyrimidin-2-yl)pyrrolidine-1-carboxylate (150 mg, 46%) as a solid.

Step 4

To a solution of tert-butyl 3-(5-methoxypyrimidin-2-yl)pyrrolidine-1-carboxylate (13 mg, 0.047 mmol) in dry CH₂Cl₂ (0.5 mL) was added TFA (20% in CH₂Cl₂, 2 mL) at 0° C. The formed solution was stirred at rt for 2 h. The reaction mixture was concentrated in vacuo to give the crude product (8 mg), which was used for next step without purification.

Preparation 16

Methyl 2-(pyrrolidin-3-yl)pyrimidine-5-carboxylate

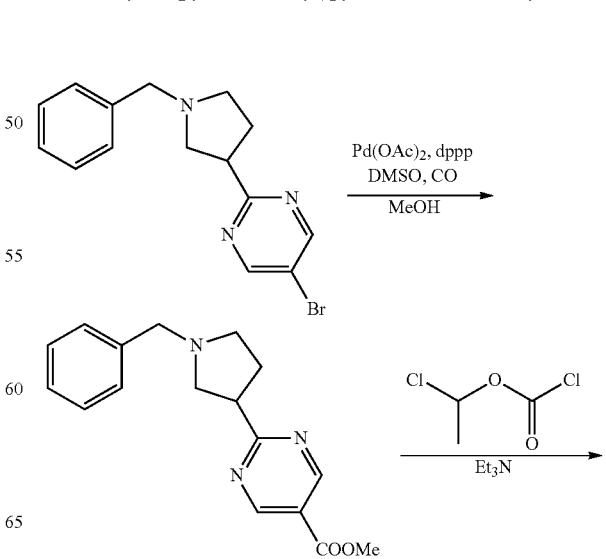

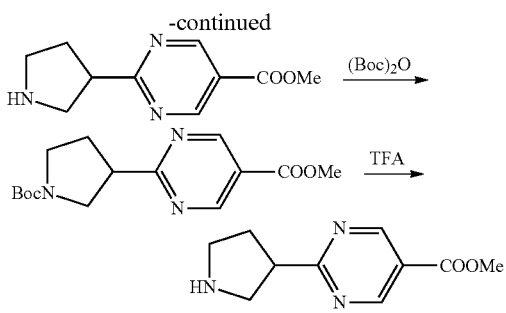

Step 1

A mixture of 2-(1-benzylpyrrolidin-3-yl)-5-bromopyrimidine (514 mg, 1.62 mmol), dppp (132 mg, 0.32 mmol), Et$_3$N (360 mg, 3.56 mmol) and Pd (OAc)$_2$ (72 mg, 0.32 mmol) in MeOH (50 mL) and DMSO (15 mL) was heated to 80 degree for 24 hours under CO (50 psi). The reaction mixture was filtered and the filtrate was concentrated, treated with water (20 mL) and extracted with EtOAc (20 mL×3). The combined organic layers were concentrated to give an oil which was purified by column chromatography to afford crude methyl 2-(1-benzylpyrrolidin-3-yl)pyrimidine-5-carboxylate (480 mg, 100%).

Steps 2-4

Procedures analogous to those described in Preparation 12 Steps 3-5 were employed.

Preparation 17

(S)-3-Hydroxy-pyrrolidine-1-carboxylic acid 5-hydroxy-adamantan-2-yl ester (ca. 1:1 mixture of cis- and trans-isomer)

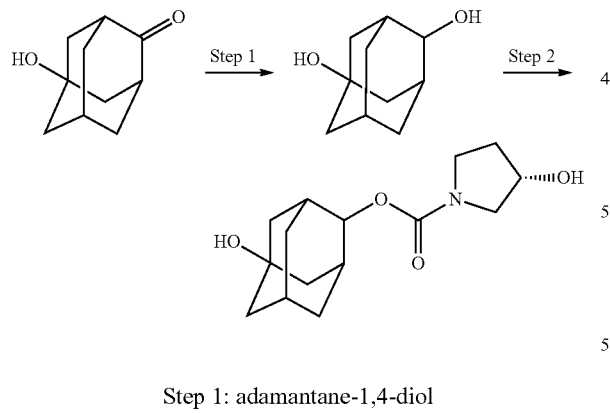

Step 1: adamantane-1,4-diol

Sodium borohydride (3.00 g) is added in three equal portions to a solution of 5-hydroxy-adamantan-2-one (5.00 g) in methanol (100 mL) chilled in an ice bath. The mixture is stirred in the cooling bath for 1 h and at room temperature overnight. 1 M hydrochloric acid is added and the resulting mixture is stirred for 0.5 h. The mixture is concentrated, water is then added to the residue, and the resulting mixture is extracted with ethyl acetate. The combined extract is washed with brine, dried (MgSO$_4$), and concentrated to give the title compound as a mixture of diastereomers (ca. 1:1). Yield: 3.20 g (63% of theory); Mass spectrum (ESI$^+$): m/z=186 [M+NH$_4$]$^+$.

Step 2: (S)-3-hydroxy-pyrrolidine-1-carboxylic acid 5-hydroxy-adamantan-2-yl ester Triphosgene (0.58 g) dissolved in dichloromethane (10 mL) is added dropwise to a solution of adamantane-1,4-diol (1.00 g) and pyridine (10 mL) in dichloromethane (30 mL) cooled to −10° C. The solution is stirred at ca. 0° C. for 2.5 h and then (S)-3-hydroxy-pyrrolidine (0.50 mL) is added. The resulting solution is stirred overnight while warming to room temperature. The solution is then diluted with dichloromethane (50 mL) and chilled in an ice bath. 4 M hydrochloric acid (25 mL) is added and the resulting mixture is stirred for 5 min. The organic phase is separated and washed with 4 M hydrochloric acid and water. The organic phase is dried (MgSO$_4$) and concentrated to give the title compound as a mixture of diastereomers (ca. 1:1). Yield: 0.98 g (59% of theory); Mass spectrum (ESI$^+$): m/z=282 [M+H]$^+$.

EXAMPLE 1

(R)-(trans-(1-carbamoyl-4-adamantyl)) 3-(3,5-difluoropyridin-2-yloxy)pyrrolidine-1-carboxylate

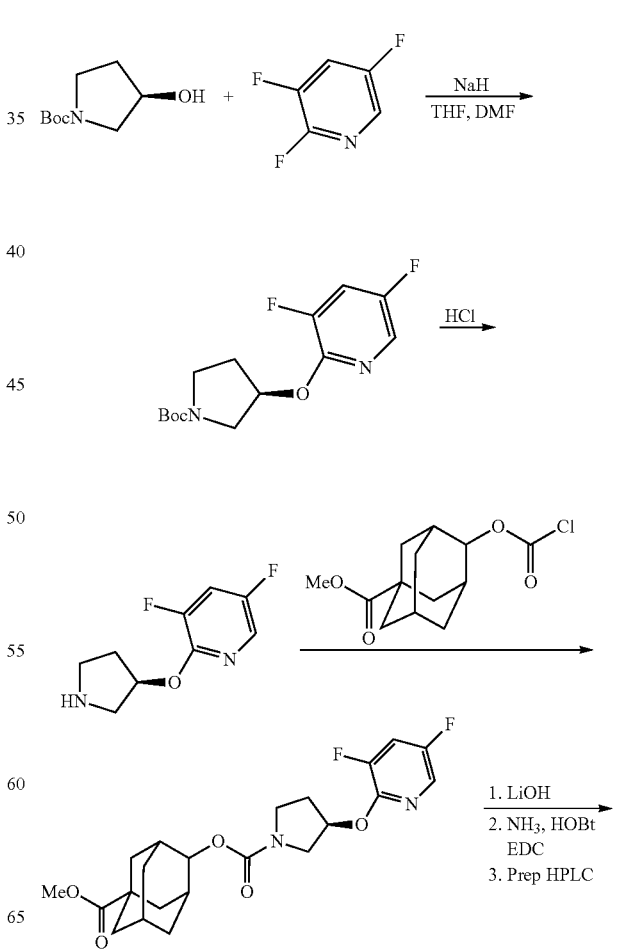

-continued

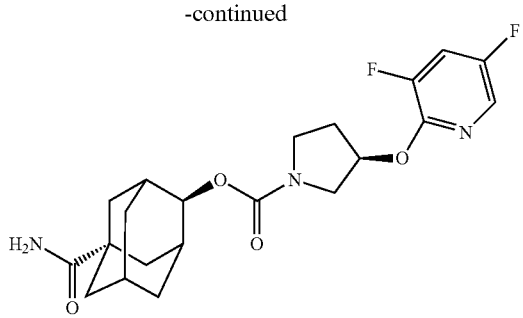

Step 1

To a stirred solution of (R)-tert-butyl 3-hydroxypyrrolidine-1-carboxylate (1.10 g, 5.89 mmol) and 2,3,5-trifluoropyridine (0.86 g, 6.48 mmol) in dry THF (20 mL) and dry DMF (4 mL), at rt was added 60% NaH in oil (0.35 g, 8.84 mmol). The mixture was stirred in a 40° C. oil bath overnight, cooled to rt, diluted with ether (175 mL), washed with water (25 mL) and brine (25 mL), and dried over $Na_2SO_4$. Removal of the solvent left a dark oil (1.94 g) which was purified by chromatography on a 40-g silica cartridge eluted with a 0-100% EtOAc in hexanes gradient to afford (R)-tert-butyl 3-(3,5-difluoropyridin-2-yloxy)pyrrolidine-1-carboxylate (0.83 g, 47%). LC-MS Method 1 $t_R$=1.85 min, m/z=301.

Step 2

(R)-tert-butyl 3-(3,5-difluoropyridin-2-yloxy)pyrrolidine-1-carboxylate (0.83 g, 2.75 mmol) was dissolved in 4M HCl in dioxane (5 mL, 200 mmol) and stirred overnight at rt. The mixture was concentrated to leave (R)-3,5-difluoro-2-(pyrrolidin-3-yloxy)pyridine as its HCl salt (722 mg, quant). LC-MS Method 1 $t_R$=0.58 min, m/z=201.

Step 3

To an ice cold solution of (R)-3,5-difluoro-2-(pyrrolidin-3-yloxy)pyridine HCl salt (540 mg, 2.28 mmol) and i-$Pr_2$NEt (1.7 mL, 9.5 mmol) in $CH_2Cl_2$ (20 mL) was added an ice cold 0.1 M solution of 1-(methoxycarbonyl)-4-adamantyl chloroformate in $CH_2Cl_2$ (22 mL, 2.2 mmol), prepared as described in Preparation 1. The mixture was allowed to warm to rt and stirred over the weekend. The mixture was concentrated to leave a yellow solid which was dissolved in EtOAc (110 mL), washed with 5% aq HCl (10 mL) and brine (10 mL), and dried over $Na_2SO_4$. Removal of the solvent left crude (R)-(1-(methoxycarbonyl)-4-adamantyl) 3-(3,5-difluoropyridin-2-yloxy)pyrrolidine-1-carboxylate (875 mg, 88%) as a mixture of E and Z isomers which was used without further purification.

Step 4

To a stirred solution of crude (R)-(1-(methoxycarbonyl)-4-adamantyl) 3-(3,5-difluoropyridin-2-yloxy)pyrrolidine-1-carboxylate (875 mg, 2.0 mmol) in MeOH (6 mL), THF (3 mL) and water (3 mL) was added solid $LiOH.H_2O$ (200 mg, 4.8 mmol). The mixture was stirred overnight at rt and additional $LiOH.H_2O$ (100 mg, 2.4 mmol) was added. The mixture was stirred overnight and concentrated under reduced pressure. The residue was partitioned between EtOAc (100 mL) and 5% aq HCl (20 mL). The organic layer was dried over $Na_2SO_4$ and concentrated to leave (R)-4-(3-(3,5-difluoropyridin-2-yloxy)pyrrolidine-1-carbonyloxy)adamantane-1-carboxylic acid (780 mg, 92%) as a mixture of E and Z isomers. LC-MS Method 1 $t_R$=1.62 min, m/z=423; $t_R$=1.72 min, m/z=423.

Step 5

A solution of (R)-4-(3-(3,5-difluoropyridin-2-yloxy)pyrrolidine-1-carbonyloxy)adamantane-1-carboxylic acid (780 mg, 1.85 mmol), $HOBt.H_2O$ (707 mg, 4.6 mmol) and i-$Pr_2$NEt (1.2 mL, 9.3 mmol) in $CH_2Cl_2$ (80 mL) was cooled in an ice bath and 0.5 M $NH_3$ in dioxane (18.5 mL, 9.25 mmol) was added followed by solid EDC.HCl (885 mg, 4.6 mmol). The ice bath was allowed to melt and the mixture was stirred overnight at rt. The mixture was concentrated and the residue was taken up in EtOAc (100 mL), washed with 5% aq HCl (10 mL), satd aq $NaHCO_3$ (10 mL) and brine (10 mL), and dried over $Na_2SO_4$. Removal of the solvent left (R)-(1-carbamoyl-4-adamantyl) 3-(3,5-difluoropyridin-2-yloxy)pyrrolidine-1-carboxylate as a mixture of E and Z isomers (713 mg). The longer retention time isomer was isolated by prep HPLC (201 mg). This material was dissolved in $CH_2Cl_2$ (100 mL), washed with 1:1 satd aq $NaHCO_3$/brine (15 mL) and dried over $Na_2SO_4$. Removal of the solvent left a white solid (190 mg) which was further purified by chromatography on a 12-g silica cartridge eluted with a 0-10% MeOH in $CH_2Cl_2$ gradient to afford (R)-(trans-(1-carbamoyl-4-adamantyl)) 3-(3,5-difluoropyridin-2-yloxy)pyrrolidine-1-carboxylate (144 mg, 18%) as a white solid. LC-MS Method 2 $t_R$=7.1 min, m/z=422; $^1$H NMR ($CD_3OD$) 1.50-1.65 (3H), 1.85-2.20 (9H), 2.25 (3H), 3.5-3.9 (4H), 4.78 (s, 1H), 5.61 (br s, 1H), 7.56 (m, 1H), 7.88 (m, 1H).

EXAMPLE 2

(S)-(trans-(1-carbamoyl-4-adamantyl)) 3-(3,5-difluoropyridin-2-yloxy)pyrrolidine-1-carboxylate

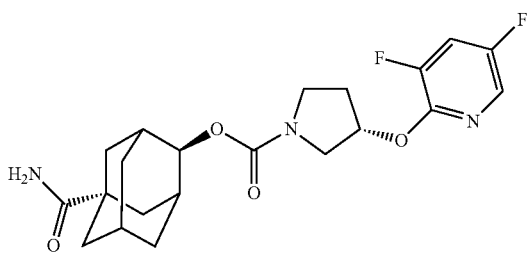 [SMILES: NC(=O)[C@]12CC3CC(C1)[C@@H](OC(=O)N1CC[C@H](Oc4ncc(F)cc4F)C1)C(C3)C2]

The title compound was prepared following procedures analogous to those described in example using (S)-tert-butyl 3-hydroxypyrrolidine-1-carboxylate in Step 1. LC-MS Method 2 $t_R$=7.02 min, m/z=422; $^1$H NMR ($CDCl_3$) 1.35-

1.50 (3H), 1.85-2.30 (12H), 3.60-3.85 (4H), 4.85 (s, 1H), 5.30 (br s, 1H), 5.59 (br s, 2H), 7.22 (m, 1H), 7.83 (m, 1H)

EXAMPLE 3

(R)-(trans-(1-carbamoyl-4-adamantyl)) 3-(imidazo[1,2-b]pyridazin-6-yloxy)pyrrolidine-1-carboxylate

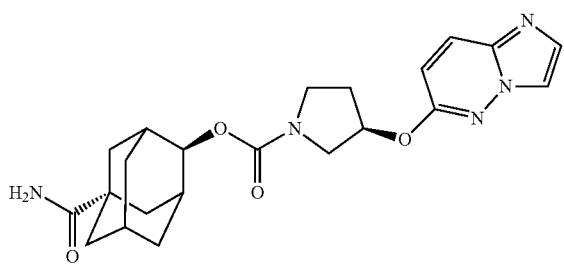 [SMILES: NC(=O)[C@]12CC3CC(C1)[C@@H](OC(=O)N1CC[C@@H](Oc4ccc5nccn5n4)C1)C(C3)C2]

The title compound was prepared following procedures analogous to those described in example using 6-chloroimidazo[1,2-b]pyridazine in Step 1. LC-MS Method 2 $t_R$=3.78 min, m/z=426; $^1$H NMR (CD$_3$OD) [selected resonances] 7.44 (d, 1H), 8.07 (s, 1H), 8.23 (d, 1H), 8.31 (s, 1H)

EXAMPLE 4

(R)-(trans-(1-hydroxy-4-adamantyl)) 3-(5-(trifluoromethyl)pyridin-2-yloxy)pyrrolidine-1-carboxylate

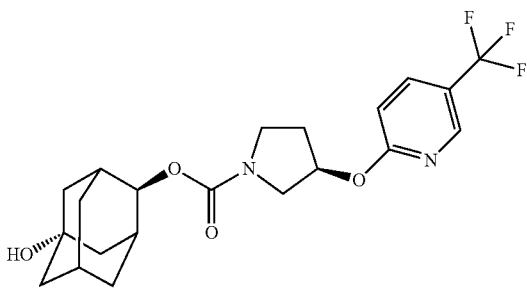 [SMILES: O=C(O[C@H]1C2CC3CC1C[C@](O)(C3)C2)N1CC[C@@H](Oc2ccc(C(F)(F)F)cn2)C1]

The title compound was prepared following procedures analogous to those described in Example 1 Steps 1 to 3 using 2-chloro-5-(trifluoromethyl)pyridine in Step 1 and a solution of 1-hydroxy-4-adamantyl chloroformate, prepared as described in Preparation 2, in Step 3. LC-MS Method 1 $t_R$=1.8 min, m/z=427; $^1$H NMR (CD$_3$OD) 1.40-1.55 (3H), 1.70-2.35 (12H), 3.50-3.80 (4H), 4.78 (s, 1H), 5.66 (br s, 1H), 6.97 (d, 1H), 7.96 (d, 1H), 8.47 (s, 1H)

EXAMPLE 5

(R)-(trans-(1-carbamoyl-4-adamantyl)) 3-(5-(trifluoromethyl)pyridin-2-yloxy)pyrrolidine-1-carboxylate

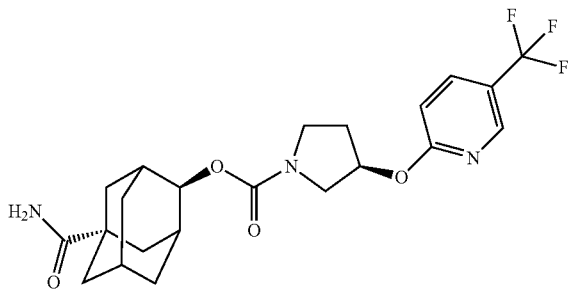 [SMILES: NC(=O)[C@]12CC3CC(C1)[C@@H](OC(=O)N1CC[C@@H](Oc4ccc(C(F)(F)F)cn4)C1)C(C3)C2]

The title compound was prepared following procedures analogous to those described in Example 1 using 2-chloro-5-(trifluoromethyl)pyridine in Step 1. LC-MS Method 2 $t_R$=8.08 min, m/z=454; $^1$H NMR (CDCl$_3$) 1.50-1.60 (3H), 1.5-2.30 (12H), 3.55-3.80 (4H), 4.86 (s, 1H), 5.28 (br s, 1H), 5.50-5.70 (2H), 6.82 (m, 1H), 7.78 (m, 1H), 8.43 (s, 1H)

EXAMPLE 6

(S)-(trans-(1-carbamoyl-4-adamantyl)) 3-(5-(trifluoromethyl)pyridin-2-yloxy)pyrrolidine-1-carboxylate

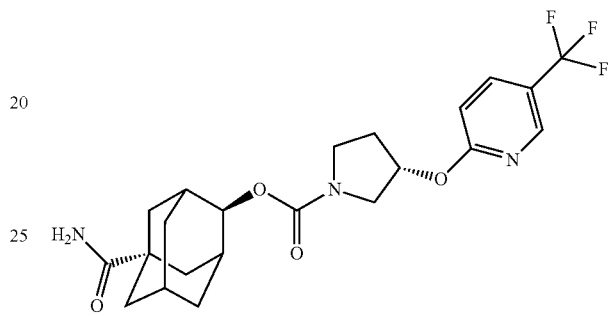

The title compound was prepared following procedures analogous to those described in Example 1 using (S)-tert-butyl 3-hydroxypyrrolidine-1-carboxylate and 2-chloro-5-(trifluoromethyl)pyridine in Step 1. LC-MS Method 2 $t_R$=8.07 min, m/z=454; $^1$H NMR (CDCl$_3$) 1.50-1.60 (3H), 1.5-2.30 (12H), 3.55-3.80 (4H), 4.86 (s, 1H), 5.28 (br s, 1H), 5.50-5.70 (2H), 6.82 (m, 1H), 7.78 (m, 1H), 8.43 (s, 1H)

EXAMPLE 7

2-adamantyl 2-phenylpyrrolidine-1-carboxylate

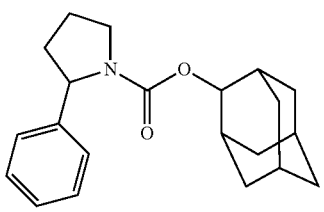 [SMILES: O=C(OC1C2CC3CC(C2)CC1C3)N1CCCC1c1ccccc1]

A vial equipped with a flea stir bar was charged with 2-phenylpyrrolidine (17 mg, 0.12 mmol), i-Pr$_2$NEt (0.031 mL, 0.17 mmol). A solution of 2-adamantyl chloroformate (25 mg, 0.12 mmol) in CH$_2$Cl$_2$ (1.5 mL) was added. The mixture was stirred over the weekend and applied to a 10-mL ChemElut cartridge prewetted with 5% aq HCl (5 mL). The cartridge was eluted with ether (20 mL). The eluate was concentrated and the residue was purified by prep HPLC to afford the title compound (24 mg, 63%). LC-MS Method 2 $t_R$=11.81 min, m/z=326, $^1$H NMR (CDCl$_3$) 0.92 (m, 1H), 1.03 (m, 1H), 1.30-2.20 (14H), 2.32 (m, 1H), 2.50 (br s, 1H), 3.64 (m, 2H), 4.70-5.10 (2H), 7.18 (m, 3H), 7.28 (m, 2H).

EXAMPLE 8

2-adamantyl 3-phenylpyrrolidine-1-carboxylate

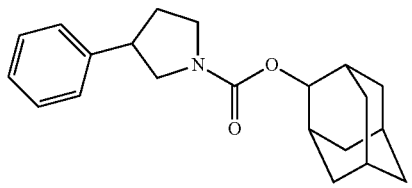 [SMILES: O=C(OC1C2CC3CC(C2)CC1C3)N1CCC(c2ccccc2)C1]

The procedure of Example 7 was followed using 3-phenylpyrrolidine. $^1$H NMR (CDCl$_3$) 1.57 (2H), 1.70-2.10 (14H), 2.28 (m, 1H), 3.30-4.00 (4H), 4.86 (s, 1H), 7.23 (m, 3H), 7.35 (m, 2H).

EXAMPLE 9

2-adamantyl 2-benzylpyrrolidine-1-carboxylate

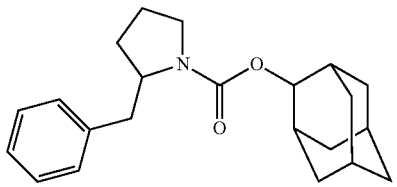 [SMILES: O=C(OC1C2CC3CC(C2)CC1C3)N1CCCC1Cc1ccccc1]

The procedure of Example 7 was followed using 2-benzylpyrrolidine. $^1$H NMR (CDCl$_3$) 1.50-2.20 (18H), 2.61 (dd, 1H), 3.17 (dd, 1H), 3.39 (m, 2H), 4.08 (m, 1H), 4.90 (1H), 7.18 (m, 3H), 7.28 (m, 2H).

EXAMPLE 10

2-adamantyl 3-benzylpyrrolidine-1-carboxylate

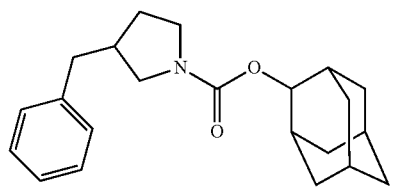 [SMILES: O=C(OC1C2CC3CC(C2)CC1C3)N1CCC(Cc2ccccc2)C1]

The procedure of Example 7 was followed using 3-benzylpyrrolidine. LC-MS Method 1 t$_R$=2.48 min, m/z=340, $^1$H NMR (CDCl$_3$) 1.45-2.05 (16H), 2.44 (m, 1H), 2.68 (m, 2H), 3.07 (m, 1H), 3.33 (m, 1H), 3.54 (m, 2H), 4.82 (s, 1H), 7.18 (m, 3H), 7.28 (m, 2H).

EXAMPLE 11

1-(2-adamantyl) 4-methyl 4-phenylpiperidine-1,4-dicarboxylate

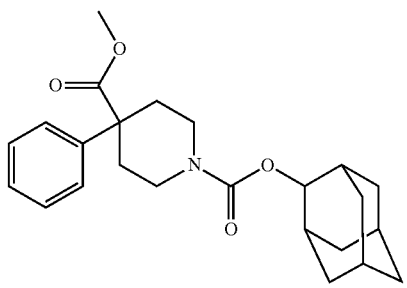 [SMILES: COC(=O)C1(c2ccccc2)CCN(C(=O)OC2C3CC4CC(C3)CC2C4)CC1]

To a stirred, ice-cold solution of methyl 4-phenylpiperidine-4-carboxylate hydrochloride (983 mg, 3.8 mmol) and i-Pr$_2$NEt (1.88 mL, 10.5 mmol) in CH$_2$Cl$_2$ (25 mL) was added 2-adamantyl chloroformate (750 mg, 3.5 mmol). The ice bath was allowed to melt and the mixture was stirred overnight at rt. The mixture was diluted with ether (150 mL), washed with 5% aq HCl (2×30 mL) and satd aq NaHCO$_3$ (30 mL) and dried over MgSO$_4$. Removal of the solvent left the crude product (1.37 g, 99%) as a white solid. A 40-mg portion was purified by prep HPLC to afford the title compound (32 mg). LC-MS Method 1 t$_R$=2.4 min, m/z=398, $^1$H NMR (CDCl$_3$) 1.58 (m, 2H), 1.70-2.10 (14H), 2.56 (d, 2H), 3.10 (br d, 2H), 3.68 (s, 3H), 4.08 (d, 2H), 4.83 (s, 1H), 7.27 (m, 1H), 7.36 (m, 4H).

EXAMPLE 12

2-(1-(2-adamantyloxycarbonyl)-4-o-tolylpiperidin-4-yl)acetic acid

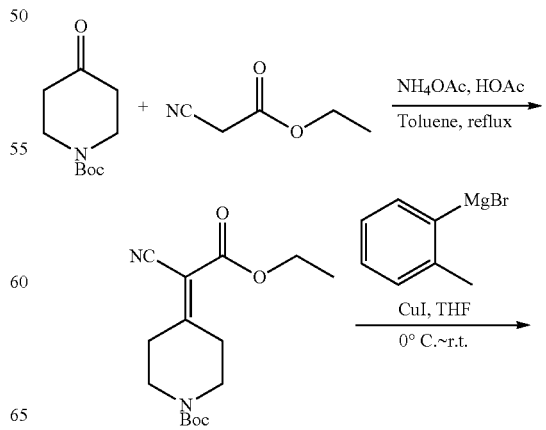

61
-continued

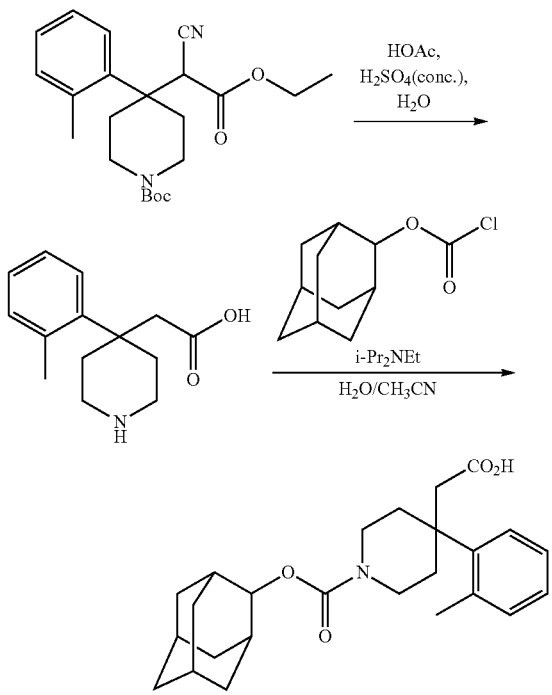

Step 1

Ethyl cyanoacetate (3.475 mL, 1.3 equiv), ammonium acetate (1.16 g, 0.6 equiv), acetic acid (1.725 mL, 1.2 equiv) were added to a solution of N-Boc-4-piperidone (5 g, 25.11 mmol) in toluene (55 mL). The mixture was heated at 110° C. for 2 h, 85° C. overnight, then at 135° C. for 4 h. The mixture was washed with 5% aq NaOH (15 mL), water (15 mL) and brine (10 mL), and dried over $Na_2SO_4$. After filtration and concentration, the residue was purified by chromatography on a 120-g silica gel cartridge, eluted with a 5 to 40% EtOAc in hexanes gradient, to afford tert-butyl 4-(1-cyano-2-ethoxy-2-oxoethylidene)piperidine-1-carboxylate (4.71 g, 64%) as an off-white solid.

Step 2

A mixture of tert-butyl 4-(1-cyano-2-ethoxy-2-oxoethylidene)piperidine-1-carboxylate (196 mg, 0.667 mmol), copper iodide (39 mg, 0.3 equiv) and dry THF (4 mL) was degassed and recharged with $N_2$ gas (3×), and cooled to 0° C. A solution of o-tolylmagnesium bromide (2.0 M in ether, 600 μL, 1.8 equiv) was added dropwise. The mixture was stirred 1 h at 0° C. under protection of $N_2$ gas before being warmed to rt slowly and stirred 2 h at rt. LC-MS found the reaction was complete. The mixture was cooled to 0° C. again, quenched with 2% aq HCl to pH=~5, extracted with EtOAc (3×35 mL). The combined organic layers were washed with satd $NH_4Cl$ (10 mL) and brine (10 mL), and dried over $Na_2SO_4$. After filtration and concentration, the residue was purified by chromatography on a 12-g silica gel cartridge, eluted with a 0 to 30% EtOAc in hexanes gradient, to afford tert-butyl 4-(1-cyano-2-ethoxy-2-oxoethyl)-4-o-tolylpiperidine-1-carboxylate (226 mg, 88%) as a clear oil.

62

Step 3 tert-butyl 4-(1-cyano-2-ethoxy-2-oxoethyl)-4-o-tolylpiperidine-1-carboxylate (226 mg, 0.585 mmol) was mixed with acetic acid (2 mL), conc sulfuric acid (1 mL) and water (1 mL). The mixture was heated to 140° C. for 6 h. After cooling down to rt, the mixture was basified with 5% aq NaOH solution to pH=~9.

Step 4

A fraction of the above aqueous solution (contains ~15 mg of 2-(4-o-tolylpiperidin-4-yl)acetic acid, 0.064 mmol) was mixed with 2-adamantyl chloroformate (15 mg, 1.1 equiv). i-$Pr_2$NEt (100 μL, excess) was added. Acetonitrile was added to make the mixture homogeneous. After stirring for 1 h at rt, the mixture was acidified and purified by prep HPLC to afford 2-(1-(2-adamantyloxycarbonyl)-4-o-tolylpiperidin-4-yl) acetic acid (4.4 mg). LC-MS Method 1 $t_R$=2.13 min, m/z=412, $^1$H NMR ($CDCl_3$) [selected resonances] 7.14 (m, 4H), 4.82 (s, 1H), 3.72 (br s, 2H), 2.78 (s, 2H), 2.52 (s, 3H), 2.46 (dt, 2H), 2.0 (m, 5H), 1.06 (d, 3H).

EXAMPLE 13

1-(2-adamantyl) 3-ethyl 3-benzylpiperidine-1,3-dicarboxylate

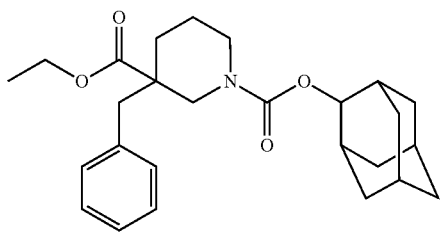 [SMILES: CCOC(=O)C1(Cc2ccccc2)CCCN(C(=O)OC2C3CC4CC(C3)CC2C4)C1]

The procedure of Example 7 was followed using ethyl 3-benzylpiperidine-3-carboxylate. LC-MS Method 2 $t_R$=12.77 min, m/z=426, $^1$H NMR ($CDCl_3$) 1.12 (t, 3H), 1.40-2.10 (18H), 2.78 (m, 1H), 2.89 (m, 1H), 3.17 (d, 1H), 3.68 (m, 2H), 3.95-4.20 (3H), 4.83 (s, 1H), 7.11 (m, 2H), 7.23 (m, 3H).

EXAMPLE 14

1-(2-adamantyl) 3-ethoxycarbonyl-3-(2-methoxybenzyl)piperidine-1-carboxylate

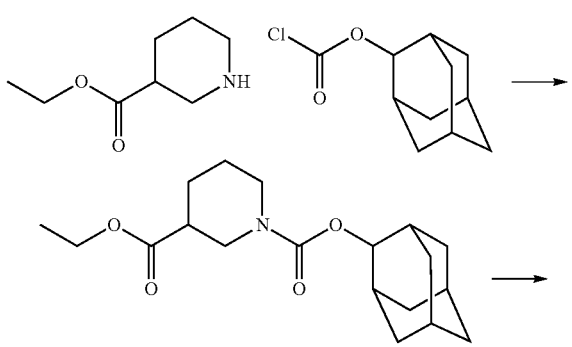

-continued

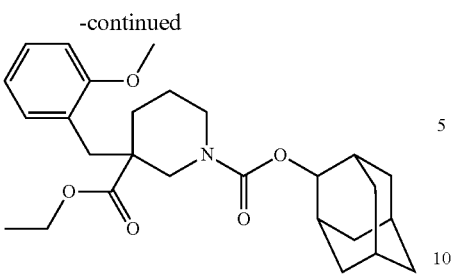

Step 1

1-(2-adamantyl) 3-ethoxycarbonylpiperidine-1-carboxylate was prepared following a procedure analogous to that described in Example 7 using ethyl piperidine-3-carboxylate.

Step 2

To a stirred solution of diisopropylamine (6.3 g, 62.7 mmol) in dry THF (120 mL) at −20° C. under $N_2$ was added 2.5 M n-BuLi (25.1 mL, 62.7 mmol). The resulting solution was added dropwise to a stirred solution of 1-(2-adamantyl) 3-ethoxycarbonylpiperidine-1-carboxylate (14.0 g, 41.8 mmol) in dry THF (170 mL) at −70° C. The mixture was stirred for 1 h at −70° C. and 2-methoxybenzyl bromide (10.9 g, 54.3 mmol) was added. The mixture was stirred for 4 h at rt, quenched with brine and extracted with $CH_2Cl_2$. The organic layer was dried over $Na_2SO_4$, concentrated and purified by column chromatography to afford the title compound (14.3 g, 75%). LC-MS Method 3 $t_R$=2.04 min, m/z=456.

EXAMPLE 15

2-adamantyl 4-((2-methoxy-2-oxoethoxy)methyl)-4-phenylpiperidine-1-carboxylate

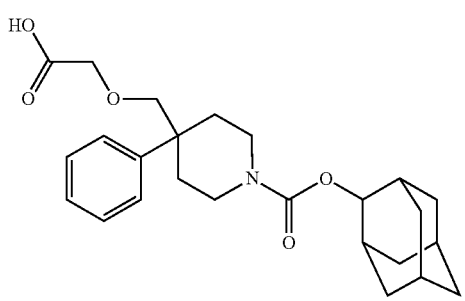 [SMILES: O=C(O)COCC1(c2ccccc2)CCN(C(=O)OC2C3CC4CC(C3)CC2C4)CC1]

To a stirred solution of 2-adamantyl 4-(hydroxymethyl)-4-phenylpiperidine-1-carboxylate (230 mg, 0.62 mmol) in dry DMF (5 mL) was added 60% NaH in oil (60 mg, 2.5 mmol). The mixture was stirred at rt for 0.5 h and methyl bromoacetate (0.24 mL, 2.5 mmol) was added. The mixture was stirred at 50° C. in an oil bath for 4 h. The mixture was diluted with ether (90 mL), washed with water (3×20 mL), dried over MgSO4 and concentrated to leave an oil (358 mg). This material was purified by column chromatography on silica gel, eluted with an EtOAc in hexanes gradient, followed by prep HPLC to afford the title compound (20 mg, 7%) as an oil. LC-MS Method 2 $t_R$=11.79 min, m/z=442.

EXAMPLE 16

2-((1-(2-adamantyloxycarbonyl)-4-phenylpiperidin-4-yl)methoxy)acetic acid

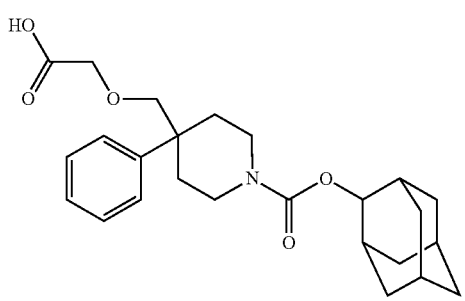 [SMILES: O=C(O)COCC1(c2ccccc2)CCN(C(=O)OC2C3CC4CC(C3)CC2C4)CC1]

To a stirred solution of 2-adamantyl 4-((2-methoxy-2-oxoethoxy)methyl)-4-phenylpiperidine-1-carboxylate (17.5 mg, 0.04 mmol) in THF (0.5 mL) and MeOH (1 mL) were added LiOH.$H_2O$ (8.3 mg, 0.2 mmol) and water (0.5 mL). The mixture was stirred at rt for 18 h and submitted directly to prep HPLC. The product from prep HPLC (8.3 mg) was stirred gently with MP-carbonate resin (75 mg), MeOH (2 mL) and $CH_2Cl_2$ (2 mL) for 22 h. The mixture was filtered and the resin beads collected were resuspended in 20:1 $CH_2Cl_2$/TFA (5 mL) overnight. The mixture was filtered and the filtrate was concentrated to leave crude material (2.5 mg). This material was purified by prep HPLC to afford the title compound (0.75 mg). LC-MS Method 1 $t_R$=2.12 min, m/z=428.

EXAMPLE 17

2-adamantyl 3-(1-methyl-2-oxo-1,2-dihydroquinolin-6-yl)pyrrolidine-1-carboxylate

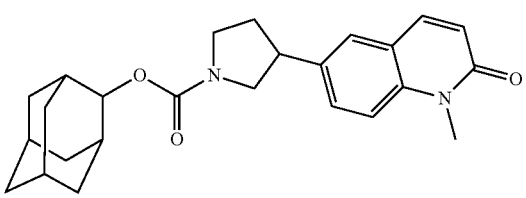 [SMILES: Cn1c(=O)ccc2cc(C3CCN(C(=O)OC4C5CC6CC(C5)CC4C6)C3)ccc21]

The procedure of Example 7 was followed using 1-methyl-6-(pyrrolidin-3-yl)quinolin-2(1H)-one. LC-MS Method 1 $t_R$=2.04 min, m/z=407, $^1$H NMR (CDCl$_3$) 1.58 (2H), 1.70-

2.40 (14H), 3.48 (m, 3H), 3.71 (m, 1H), 3.76 (s, 3H), 3.96 (m, 1H), 6.82 (d, 1H), 7.35-7.55 (3H), 7.72 (d, 2H).

EXAMPLE 18

4-(1-(2-adamantyloxycarbonyl)piperidin-3-yl)benzoic acid

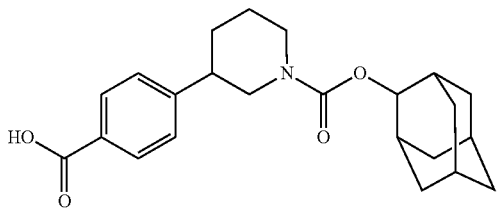 [SMILES: O=C(O)c1ccc(C2CCCN(C(=O)OC3C4CC5CC(C4)CC3C5)C2)cc1]

The procedure of Example 7 was followed using 4-(piperidin-3-yl)benzoic acid. LC-MS Method 1 $t_R$=2.1 min, m/z=384, $^1$H NMR (CDCl$_3$) [selected resonances] 4.88 (s, 1H), 7.36 (d, 2H), 8.08 (d, 2H).

EXAMPLE 19 trans-1-carbamoyl-4-adamantyl 2-(pyridin-2-yl)pyrrolidine-1-carboxylate

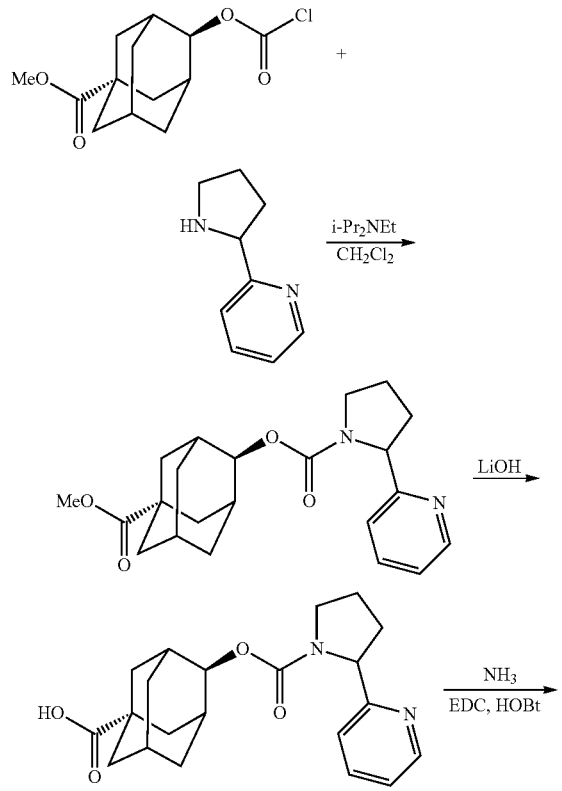

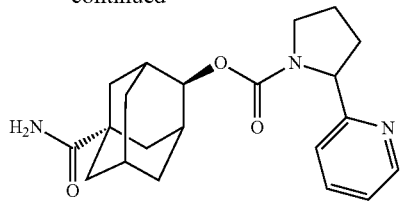

Step 1

To a stirred, ice-cold solution of 2-(pyrrolidin-2-yl)pyridine (70 mg, 0.48 mmol) and i-Pr2NEt (0.5 mL, 2.8 mmol) in CH$_2$Cl$_2$ (1 mL) was added ice cold 0.1 M 1-methoxycarbonyl-4-adamantyl chloroformate in CH$_2$Cl$_2$ (5 mL, 0.5 mmol). The mixture was allowed to warm to rt and stirred overnight. The mixture was diluted with EtOAc (100 mL), washed with water (2×10 mL) and brine (10 mL), and dried over Na$_2$SO$_4$. Removal of the solvent gave crude 1-(methoxycarbonyl)-4-adamantyl 2-(pyridin-2-yl)pyrrolidine-1-carboxylate as an oil which was used without purification.

Step 2

Crude 1-(methoxycarbonyl)-4-adamantyl 2-(pyridin-2-yl) pyrrolidine-1-carboxylate from Step 1 was dissolved in 1:1:2 H$_2$O/THF/MeOH (8 mL), LiOH.H$_2$O (200 mg, 4.8 mmol) and the resulting mixture was stirred overnight at rt. The mixture was concentrated, acidified and purified by prep HPLC. The longer $t_R$ isomer, trans-4-(2-(pyridin-2-yl)pyrrolidine-1-carbonyloxy)adamantane-1-carboxylic acid was isolated (50 mg, 28%) as a solid. LC-MS Method 1 $t_R$=1.15 min, m/z=371.

Step 3

To a stirred, ice-cold solution of trans-4-(2-(pyridin-2-yl) pyrrolidine-1-carbonyloxy)adamantane-1-carboxylic acid (50 mg, 0.13 mmol), HOBt.H$_2$O (104 mg, 0.68 mmol) and i-Pr$_2$NEt (0.25 mL, 1.4 mmol) in CH$_2$Cl$_2$ (25 mL) was added 0.5M NH$_3$ in dioxane (2.5 mL, 1.25 mmol) followed by EDC.HCl (130 mg, 0.68 mmol). The mixture was allowed to warm slowly to rt and stirred overnight. The mixture was concentrated and the residue was purified by prep HPLC to afford trans-1-carbamoyl-4-adamantyl 2-(pyridin-2-yl)pyrrolidine-1-carboxylate TFA salt (23 mg, 46%) as an oil. LC-MS Method 2 $t_R$=3.33 min, m/z=370.

EXAMPLE 20

1-carbamoyl-2-adamantyl 2-(5-(4-chlorophenyl)-1,3,4-oxadiazol-2-yl)pyrrolidine-1-carboxylate

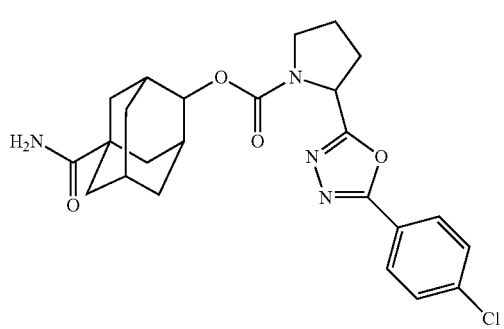 [SMILES: NC(=O)C12CC3CC(C1)C(OC(=O)N1CCCC1c1nnc(-c4ccc(Cl)cc4)o1)C(C3)C2]

The title compound was prepared following a procedure analogous to that described in Example 19 using 2-(4-chlorophenyl)-5-(pyrrolidin-2-yl)-1,3,4-oxadiazole in Step 1. The cis and trans isomers were not separated. LC-MS Method 2 $t_R$=6.62 min, m/z=471 and $t_R$=6.90 min, m/z=471.

EXAMPLE 21

1-hydroxy-4-adamantyl 3-(pyridin-4-yl)pyrrolidine-1-carboxylate

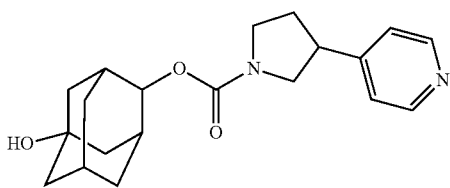 [SMILES: O=C(OC1C2CC3CC1CC(O)(C3)C2)N1CCC(c2ccncc2)C1]

A procedure analogous to that described in Example 19 Step 1 was followed using 1-hydroxy-4-adamantyl chloroformate solution and 3-(4-pyridyl)pyrrolidine. The title compound was isolated as a mixture of isomers. LC-MS Method 1 $t_R$=0.90 min, m/z=343, $^1$H NMR (CD$_3$OD) [selected resonances] 4.69 (s, 0.5H), 4.78 (s, 0.5H), 8.03 (d, 2H), 8.78 (d, 2H)

EXAMPLE 22

4-(1-((1-hydroxy-4-adamantyloxy)carbonyl)pyrrolidin-3-yl)pyridine 1-oxide

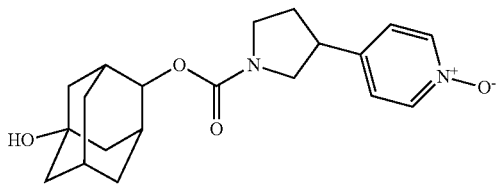 [SMILES: O=C(OC1C2CC3CC1CC(O)(C3)C2)N1CCC(c2cc[n+]([O-])cc2)C1]

A stirred solution of 1-hydroxy-4-adamantyl 3-(pyridin-4-yl)pyrrolidine-1-carboxylate (476 mg, 1.39 mmol) in CH$_2$Cl$_2$ (50 mL) was cooled in an ice bath and solid m-CPBA (~70%, 342 mg, ~1.4 mmol) was added. The ice bath was allowed to melt and the mixture was stirred at rt for 2 days. The mixture was diluted with MeOH (50 mL) and Amberlyst A26 OH⁻ (5 g) was added. The mixture was stirred for 1 h, filtered and the filtrate was concentrated to leave a viscous oil (539 mg). A 35-mg portion was purified by prep HPLC to afford the title compound (10.5 mg) as an oil. LC-MS Method 1 $t_R$=1.02 min, m/z=359, $^1$H NMR (CDCl$_3$) [selected resonances] 4.67 (s, 0.5H), 4.78 (s, 0.5H), 7.58 (d, 2H), 8.38 (d, 2H).

EXAMPLE 23 trans-1-carbamoyl-4-adamantyl 3-(3-methyl-1,2,4-oxadiazol-5-yl)pyrrolidine-1-carboxylate

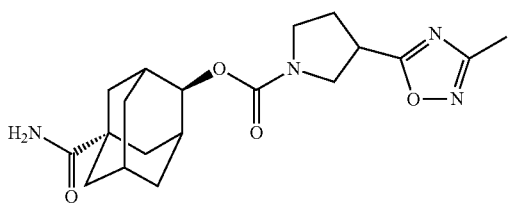 [SMILES: Cc1noc(C2CCN(C(=O)O[C@H]3C4CC5CC3C[C@](C(N)=O)(C5)C4)C2)n1]

The title compound was prepared following a procedure analogous to that described in Example 19 using 3-methyl-5-(pyrrolidin-3-yl)-1,2,4-oxadiazole in Step 1. The longer $t_R$ isomer was isolated. LC-MS Method 1 $t_R$=1.23 min, m/z=375, $^1$H NMR (CD$_3$OD) 1.57 (d, 2H), 1.85-2.15 (11H), 2.25 (m, 1H), 2.33 (s, 3H), 2.41 (m, 1H), 2.45-4.95 (5H), 4.79 (s, 1H).

EXAMPLE 24

1-hydroxy-4-adamantyl 3-(5-chloropyrimidin-2-yl)pyrrolidine-1-carboxylate

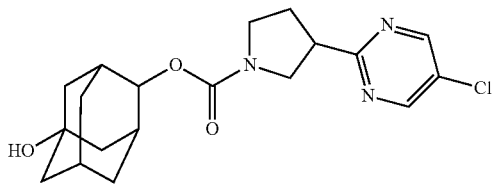 [SMILES: O=C(OC1C2CC3CC1CC(O)(C3)C2)N1CCC(c2ncc(Cl)cn2)C1]

The title compound was prepared following a procedure analogous to that described in Example 19 Step 1 using 1-hydroxy-4-adamantyl chloroformate solution and 5-chloro-2-(pyrrolidin-3-yl)pyrimidine. Two isomers were separated by prep HPLC.

Isomer 1: trans-1-hydroxy-4-adamantyl 3-(5-chloropyrimidin-2-yl)pyrrolidine-1-carboxylate. LC-MS Method 1 $t_R$=1.5 min, m/z=378, $^1$H NMR (CDCl$_3$) 1.42 (2H), 1.70-2.40 (14H), 3.55 (m, 1H), 3.72 (m, 3H), 3.90 (m, 1H), 4.86 (s, 1H), 8.66 (s, 2H).

Isomer 2: cis-1-hydroxy-4-adamantyl 3-(5-chloropyrimidin-2-yl)pyrrolidine-1-carboxylate. LC-MS Method 1 $t_R$=1.38 min, m/z=378, $^1$H NMR (CDCl$_3$) 1.53 (2H), 1.60-2.40 (14H), 3.52 (m, 1H), 3.68 (m, 3H), 4.91 (m, 1H), 4.74 (s, 1H), 8.63 (s, 2H).

EXAMPLE 25

1-hydroxy-4-adamantyl 3-(5-methyl-1,3,4-oxadiazol-2-yl)piperidine-1-carboxylate

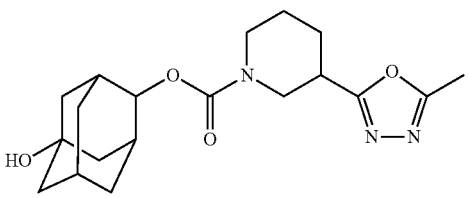 [SMILES: Cc1nnc(C2CCCN(C(=O)OC3C4CC5CC3CC(O)(C5)C4)C2)o1]

The title compound was prepared following a procedure analogous to that described in Example 19 Step 1 using 1-hydroxy-4-adamantyl chloroformate solution and 2-methyl-5-(piperidin-3-yl)-1,3,4-oxadiazole. LC-MS Method 1 $t_R$=1.35 min, m/z=362.

EXAMPLE 26

(1-carbamoyl-4-adamantyl) 3-(5-chloropyrimidin-2-yl)pyrrolidine-1-carboxylate

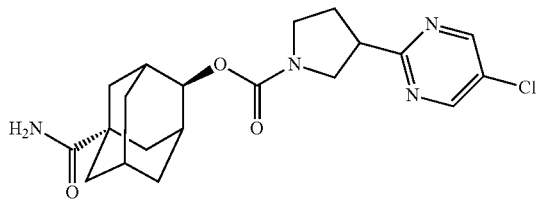 [SMILES: NC(=O)[C@]12CC3CC(C1)[C@@H](OC(=O)N1CCC(c4ncc(Cl)cn4)C1)C(C3)C2]

The title compound was prepared following a procedure analogous to that described in Example 19 using 5-chloro-2-(pyrrolidin-3-yl)pyrimidine in Step 1. Two isomers were isolated by preparative HPLC.

Isomer 1: trans-(1-carbamoyl-4-adamantyl) 3-(5-chloropyrimidin-2-yl)pyrrolidine-1-carboxylate. LC-MS Method 1 $t_R$=1.45 min, m/z=405, $^1$H NMR (CDCl$_3$) 1.54 (2H), 1.85-2.40 (13H), 3.52 (m, 1H), 3.70 (m, 3H), 3.91 (m, 1H), 4.83 (s, 1H), 5.93 (br s, 1H), 6.54 (br s, 1H), 8.64 (s, 2H).

Isomer 2: cis-(1-carbamoyl-4-adamantyl) 3-(5-chloropyrimidin-2-yl)pyrrolidine-1-carboxylate. $^1$H NMR (CDCl$_3$) 1.65-1.90 (m, 6H), 1.97-2.40 (m, 9H), 3.43-3.56 (m, 1H), 3.60-3.75 (m, 3H), 3.83-3.93 (m, 1H), 4.78 (s, 1H), 5.92 (br s, 1H), 6.64 (br s, 1H), 8.63 (s, 2H)

Isomer 1 was further separated into its enantiomers by SFC on a chiral OJ column eluted with 75:25 supercritical CO$_2$/MeOH containing 0.05% Et$_2$NH.

Isomer 1a: shorter $t_R$ isomer. LC-MS Method 3 $t_R$=1.052 min, m/z=405; $^1$H NMR (CDCl$_3$) 1.50 (m, 2H), 1.88 (m, 2H), 1.90 (m, 4H), 2.02 (m, 3H), 2.15 (m, 2H), 2.20-2.40 (m, 2H), 3.51 (m, 1H), 3.70 (m, 3H), 3.88 (m, 1H), 4.82 (s, 1H), 5.69 (s, 2H), 8.63 (m, 2H).

Isomer 1b: longer $t_R$ isomer. LC-MS Method 3 $t_R$=1.044 min, m/z=405; $^1$H NMR (CDCl$_3$) 1.50 (m, 2H), 1.88 (m, 2H), 1.90 (m, 4H), 2.02 (m, 3H), 2.15 (m, 2H), 2.22-2.43 (m, 2H), 3.51 (m, 1H), 3.72 (m, 3H), 3.91 (m, 1H), 4.85 (s, 1H), 5.45-5.70 (d, 2H), 8.63 (m, 2H)

EXAMPLE 27

2-adamantyl 4-(2-oxoindolin-1-yl)piperidine-1-carboxylate

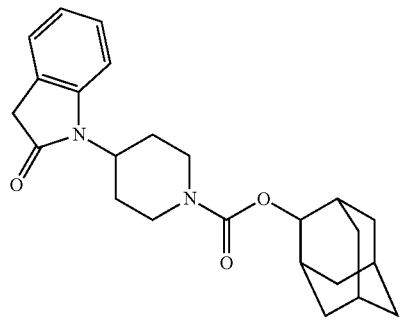 [SMILES: O=C(OC1C2CC3CC(C2)CC1C3)N1CCC(N2C(=O)Cc3ccccc32)CC1]

The procedure of Example 7 was followed using 1-(piperidin-4-yl)indolin-2-one. LC-MS Method 1 $t_R$=2.17 min, m/z=417, 395, $^1$H NMR (CDCl$_3$) 1.58 (2H), 1.70-2.15 (14H), 2.35 (m, 2H), 2.90 (2H), 3.54 (s, 2H), 4.41 (m, 3H), 4.87 (s, 1H), 7.01 (m, 2H), 7.23 (m, 2H)

EXAMPLE 28

(R)-(trans-1-hydroxy-4-adamantyl) 3-(6-chloro-2-oxo-1H-imidazo[4,5-b]pyridin-3(2H)-yl)pyrrolidine-1-carboxylate

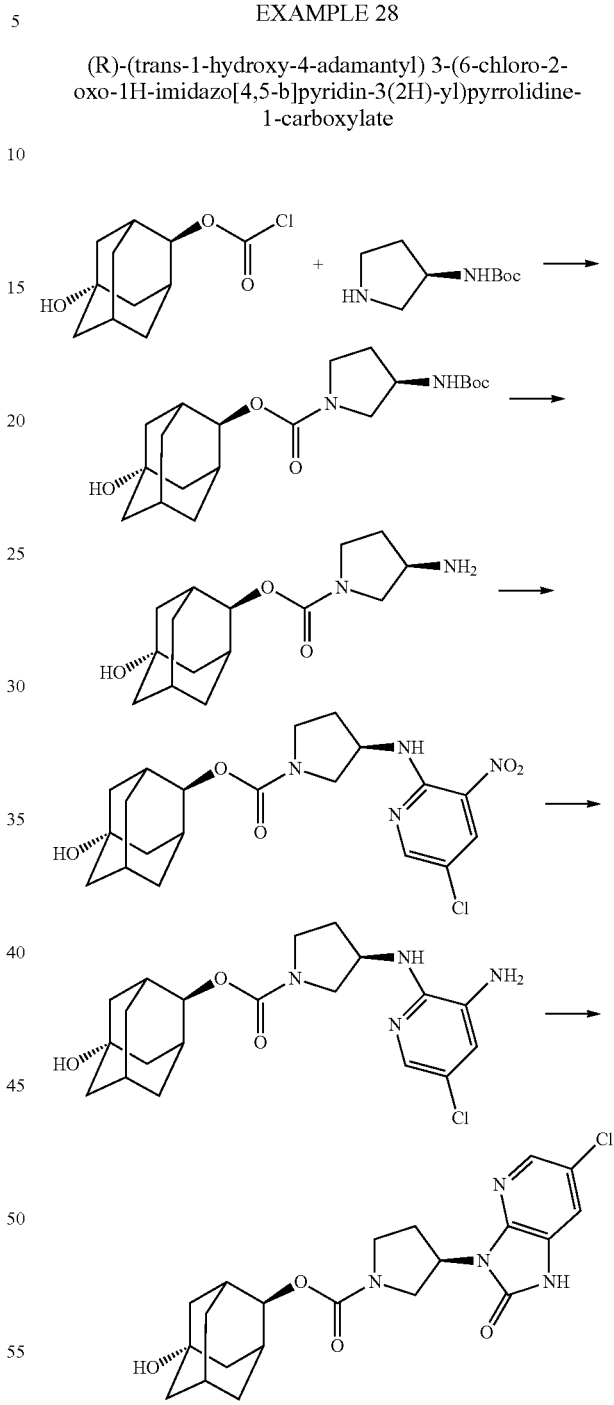

Step 1

A stirred solution of 1,4-dihydroxyadamantane (858 mg, 5.10 mmol) in CH$_2$Cl$_2$ (30 mL) and dry pyridine (10 mL) was cooled in an ice-salt bath and a solution of triphosgene (500 mg, 1.68 mmol) in CH$_2$Cl$_2$ (10 mL) was added dropwise over 5 min. The mixture was stirred in the ice bath for 2.5 h. (R)-tert-butyl pyrrolidin-3-ylcarbamate (949 mg, 5.1 mmol)

was added to the mixture. The cooling bath was allowed to expire and the mixture was stirred overnight at rt. The mixture was concentrated. The residue was taken up in EtOAc (100 mL) and washed with water (15 mL) and brine (15 mL), and dried over $Na_2SO_4$. Removal of the solvent left a white foam (1.57 g) which was purified by chromatography on a 40-g silica gel cartridge eluted with a 20 to 100% EtOAc in hexanes gradient to afford two isomeric products.

Isomer 1: (R)-(cis-1-hydroxy-4-adamantyl) 3-(tert-butoxycarbonylamino)pyrrolidine-1-carboxylate (512 mg, 26%). LC-MS Method 1 $t_R$=1.39 min, m/z=381; $^1$H NMR ($CDCl_3$) [selected resonances] 1.43 (s, 9H), 3.23 (m, 1H), 3.48 (m, 2H), 3.67 (m, 1H), 4.22 (1H), 4.63 (1H), 4.73 (s, 1H).

Isomer 2: (R)-(trans-1-hydroxy-4-adamantyl) 3-(tert-butoxycarbonylamino)pyrrolidine-1-carboxylate (475 mg, 24%). LC-MS Method 1 $t_R$=1.45 min, m/z=381; $^1$H NMR ($CDCl_3$) [selected resonances] 1.44 (s, 9H), 3.25 (dd, 1H), 3.48 (m, 2H), 3.66 (m, 1H), 4.22 (1H), 4.62 (1H), 4.82 (s, 1H).

Step 2

To a stirred solution of (R)-(trans-1-hydroxy-4-adamantyl) 3-(tert-butoxycarbonylamino)pyrrolidine-1-carboxylate (239 mg, 0.63 mmol) in $CH_2Cl_2$ (15 mL) was added TFA (5 mL). The mixture was stirred at rt for 2 h and concentrated. The residue was dissolved in $CH_2Cl_2$ (100 mL), washed with 1:1 brine/satd aq $NaHCO_3$ and dried over $Na_2SO_4$. Removal of the solvent left (R)-(trans-1-hydroxy-4-adamantyl) 3aminopyrrolidine-1-carboxylate (156 mg, 88%). LC-MS Method 1 $t_R$=0.67 min, m/z=281.

Step 3

A mixture of (R)-(trans-1-hydroxy-4-adamantyl) 3-aminopyrrolidine-1-carboxylate (33 mg, 0.12 mmol), i-$Pr_2NEt$ (0.046 mL, 0.26 mmol), 2,5-dichloro-3-nitropyridine (25 mg, 0.13 mmol) and n-PrOH (1 mL) was heated at 120° C. for 2 h in the microwave. The reaction mixture was purified by prep HPLC to afford (R)-(trans-1-hydroxy-4-adamantyl) 3-(5-chloro-3-nitropyridin-2-ylamino)pyrrolidine-1-carboxylate (40.1 mg, 78%) as a yellow oil. LC-MS Method 1 $t_R$=1.77 min, m/z=439, 437; $^1$H NMR ($CDCl_3$) 1.44 (m, 2H), 1.70-2.25 (13H), 2.38 (m, 1H), 3.38 (m, 1H), 3.63 (m, 2H), 3.90 (m, 1H), 4.79 (m, 1H), 4.86 (s, 1H), 8.19 (br s, 1H), 8.39 (s, 1H), 8.42 (s, 1H), Step 4

To a stirred solution of (R)-(trans-1-hydroxy-4-adamantyl) 3-(5-chloro-3-nitropyridin-2-ylamino)pyrrolidine-1-carboxylate (40 mg, 0.09 mmol) in dry DMF (1 mL) was added $SnCl_2$ (69 mg, 0.36 mmol). The mixture was heated at 80° C. for 3 h, cooled diluted with $CH_2Cl_2$ (100 mL) and washed with 1:1 satd aq $NaHCO_3$/brine (20 mL). The organic layer was dried over $Na_2SO_4$ and concentrated to leave the desired product (2.2 mg). The aqueous layer was concentrated and the solid residue was triturated with 5% MeOH in $CH_2Cl_2$. The filtrate was combined with the product from the organic layer and concentrated to afford (R)-(trans-1-hydroxy-4-adamantyl) 3-(3-amino-5-chloropyridin-2-ylamino)pyrrolidine-1-carboxylate (5.6 mg, 15%). LC-MS Method 1 $t_R$=1.16 min, m/z=407.

Step 5

An ice-cold, stirred solution of (R)-(trans-1-hydroxy-4-adamantyl) 3-(3-amino-5-chloropyridin-2-ylamino)pyrrolidine-1-carboxylate (5.6 mg, 0.014 mmol) and i-$Pr_2NEt$ (0.01 mL, 0.056 mmol) in $CH_2Cl_2$ (1 mL) was treated with triphosgene (1.5 mg, 0.005 mmol). The mixture was allowed to warm to rt, stirred overnight and concentrated. The residue was purified by prep HPLC to give the title compound (1.9 mg, 32%) as an oil. LC-MS Method 1 $t_R$=1.43 min, m/z=433, $^1$H NMR ($CDCl_3$) [selected resonances] 4.79 (s, 1H), 7.36 (s, 1H), 7.95 (s, 1H).

EXAMPLE 29

(R) (trans-1-carbamoyl-4-adamantyl) 3-(6-chloro-1-methyl-2-oxo-1H-imidazo[4,5-b]pyridin-3(2H)-yl) pyrrolidine-1-carboxylate

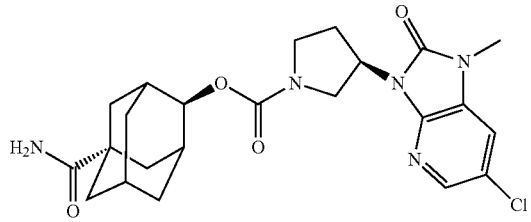 [SMILES: Cn1c(=O)n([C@@H]2CCN(C(=O)O[C@H]3C4CC5CC3C[C@](C(N)=O)(C5)C4)C2)c2ncc(Cl)cc21]

The title compound was prepared following a procedure analogous to that described in Example 19 using (R)-6-chloro-1-methyl-3-(pyrrolidin-3-yl)-1H-imidazo[4,5-b]pyridin-2(3H)-one in Step 1. The longer $t_R$ isomer was isolated. LC-MS Method 2 $t_R$=6.52 min, m/z=474, $^1$H NMR ($CD_3OD$) 1.50 (2H), 1.70-2.20 (11H), 2.25 (1H), 2.69 (m, 1H), 3.38 (s, 3H), 3.40-4.10 (4H), 4.78 (s, 1H), 5.15 (m, 1H), 7.50 (s, 1H), 8.92 (s, 1H).

EXAMPLE 30

2-adamantyl 4-(hydroxymethyl)-4-phenylpiperidine-1-carboxylate

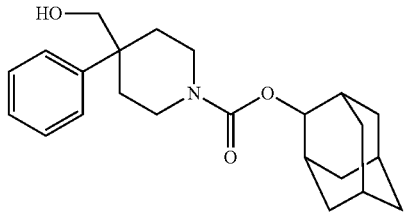 [SMILES: O=C(OC1C2CC3CC(C2)CC1C3)N1CCC(CO)(c2ccccc2)CC1]

To a stirred solution of 1-(2-adamantyl) 4-methyl 4-phenylpiperidine-1,4-dicarboxylate (1.33 g, 3.35 mmol) and MeOH (0.068 mL, 1.67 mmol) in dry THF (20 mL) at rt was added solid $LiBH_4$ (0.30 g, 13.4 mmol). The mixture was stirred at rt for 4 days. The mixture was diluted with 5% aq HCl (50 mL) and extracted with ether (175 mL). The organic layer was washed with satd aq $NaHCO_3$ (50 mL), dried over $MgSO_4$ and concentrated to afford crude title compound (1.21 g) as a white foam. A 40-mg portion was purified by prep HPLC to afford the title compound (23 mg) as a white solid. LC-MS Method 1 $t_R$=2.12 min, m/z=370, $^1$H NMR (CDCl₃) 1.58 (4H), 1.70-2.10 (12H), 2.23 (d, 2H), 3.13 (2H), 3.57 (s, 2H), 3.86 (m, 2H), 4.82 (s, 1H), 7.28 (1H), 7.38 (4H).

EXAMPLE 31

(trans-1-carbamoyl-4-adamantyl) 3-(1-methyl-1H-benzo[d]imidazol-2-yl)pyrrolidine-1-carboxylate

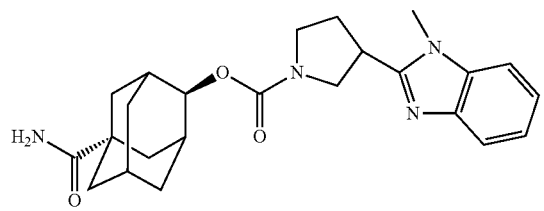 [SMILES: Cn1c(C2CCN(C(=O)O[C@H]3C4CC5CC3C[C@](C(N)=O)(C5)C4)C2)nc2ccccc21]

The title compound was prepared following a procedure analogous to that described in Example 19 using 1-methyl-2-(pyrrolidin-3-yl)-1H-benzo[d]imidazole in Step 1. The longer $t_R$ isomer was isolated from Step 3. LC-MS Method 2 $t_R$=3.82 min, m/z=423.

EXAMPLE 32

(1-carbamoyl-4-adamantyl) 2-(1-methyl-1H-benzo[d]imidazol-2-yl)pyrrolidine-1-carboxylate

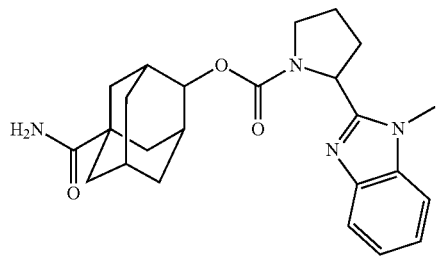 [SMILES: Cn1c(C2CCCN2C(=O)OC2C3CC4CC2CC(C(N)=O)(C4)C3)nc2ccccc21]

The title compound was prepared following a procedure analogous to that described in Example 19 using 1-methyl-2-(pyrrolidin-2-yl)-1H-benzo[d]imidazole in Step 1. A mixture of E and Z isomers was isolated from Step 3. LC-MS Method 2 $t_R$=2.97 min, m/z=423.

EXAMPLE 33

(trans-1-carbamoyl-4-adamantyl) 2-(benzo[d]thiazol-2-yl)pyrrolidine-1-carboxylate

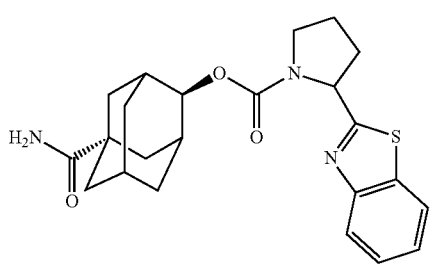 [SMILES: NC(=O)[C@]12CC3CC(C1)[C@@H](OC(=O)N1CCCC1c1nc4ccccc4s1)C(C3)C2]

The title compound was prepared following a procedure analogous to that described in Example 19 using 2-(pyrrolidin-2-yl)benzo[d]thiazole in Step 1. The longer $t_R$ isomers was isolated from Step 3. LC-MS Method 2 $t_R$=6.82 min, m/z=426.

EXAMPLE 33

2-adamantyl 3-(2-methylpyrimidin-5-yl)pyrrolidine-1-carboxylate

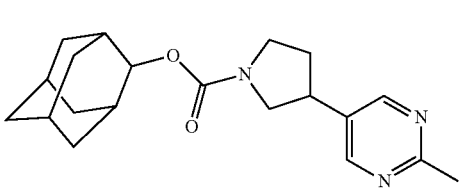 [SMILES: Cc1ncc(C2CCN(C(=O)OC3C4CC5CC(C4)CC3C5)C2)cn1]

The procedure of Example 7 was followed using 2-methyl-5-(pyrrolidin-3-yl)pyrimidine. LC-MS Method 2 $t_R$=7.92 min, m/z=342.

EXAMPLE 34

2-adamantyl 3-(5-chloropyrimidin-2-yl)pyrrolidine-1-carboxylate

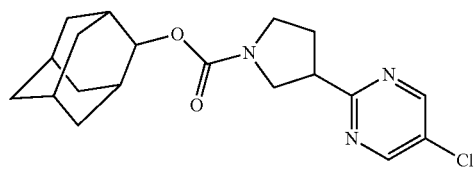 [SMILES: O=C(OC1C2CC3CC(C2)CC1C3)N1CCC(c2ncc(Cl)cn2)C1]

The procedure of Example 7 was followed using 5-chloro-2-(pyrrolidin-3-yl)pyrimidine. LC-MS Method 1 $t_R$=2.25 min, m/z=362; ¹H NMR (CDCl₃) 1.50-1.62 (m, 2H), 1.70-2.08 (m, 10H), 2.25-2.40 (m, 2H), 3.47-3.58 (m, 1H), 3.68-3.77 (m, 3H), 3.88-3.98 (m, 1H), 4.86 (s, 1H), 8.63 (s, 2H).

EXAMPLE 35

1-carbamoyl-4-adamantyl 3-(5-methylpyridin-2-yl)pyrrolidine-1-carboxylate

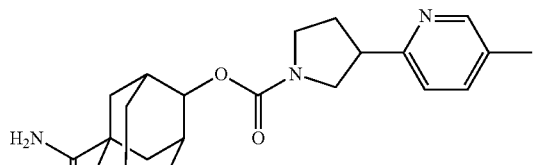

The title compound was prepared was prepared following the procedure of Example 19 using 5-methyl-2-(pyrrolidin-3-yl)pyridine in Step 1. Two isomers were isolated Isomer 1: trans-1-carbamoyl-4-adamantyl 3-(5-methylpyridin-2-yl)pyrrolidine-1-carboxylate. LC-MS Method 3 $t_R$=0.783 min, m/z=384.1; ¹H NMR (CDCl₃) 1.45 (m, 1H), 1.58 (s, 2H), 1.82 (m, 2H), 1.88 (m, 5H), 1.97 (m, 2H), 2.13 (m, 3H), 2.26 (s, 3H), 3.45 (m, 3H), 3.62 (m, 1H), 3.83 (m, 1H), 4.79 (s, 1H), 5.23 (s, 1H), 5.52 (s, 1H), 7.02 (t, 1H), 7.38 (m, 1H), 8.33 (s, 1H).

Isomer 2: cis-1-carbamoyl-4-adamantyl 3-(5-methylpyridin-2-yl)pyrrolidine-1-carboxylate. LC-MS Method 3 $t_R$=0.755 min, m/z=384.1; $^1$H NMR (CDCl$_3$) 1.62 (m, 2H), 1.69 (m, 1H), 1.72 (m, 4H), 1.78 (m, 2H), 1.94 (s, 1H), 2.07 (m, 1H), 2.17 (m, 4H), 2.24 (s, 3H), 3.45 (m, 3H), 3.61 (m, 1H), 3.82 (m, 1H), 4.76 (s, 1H), 5.18 (m, 1H), 5.51 (s, 1H), 7.01 (m, 1H), 7.36 (m, 1H), 8.31 (s, 1H).

EXAMPLE 36

1-carbamoyl-4-adamantyl 3-(2-methylpyrimidin-5-yl)pyrrolidine-1-carboxylate

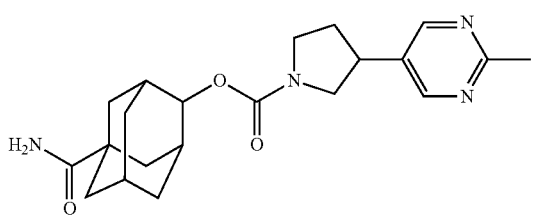 [SMILES: Cc1ncc(C2CCN(C(=O)OC3C4CC5CC3CC(C(N)=O)(C5)C4)C2)cn1]

The title compound was prepared was prepared following the procedure of Example 19 using 2-methyl-5-(pyrrolidin-3-yl)pyridine in Step 1. Two isomers were isolated.

Isomer 1: trans-1-carbamoyl-4-adamantyl 3-(5-methylpyridin-2-yl)pyrrolidine-1-carboxylate. LC-MS Method 3 $t_R$=0.885 min, m/z=385.1; $^1$H NMR (CDCl$_3$) 1.47 (m, 2H), 1.82 (m, 2H), 1.92 (m, 5H), 1.96 (m, 3H), 2.13 (s, 2H), 2.31 (m, 1H), 2.67 (s, 3H), 3.31 (m, 2H), 3.48 (m, 1H), 3.64 (m, 1H), 3.87 (m, 1H), 4.81 (m, 1H), 5.18 (s, 1H), 5.50 (s, 1H), 8.48 (d, 2H).

Isomer 2: cis-1-carbamoyl-4-adamantyl 3-(5-methylpyridin-2-yl)pyrrolidine-1-carboxylate. LC-MS Method 3 $t_R$=0.854 min, m/z=407; $^1$H NMR (CDCl$_3$) 1.63 (m, 2H), 1.75 (m, 4H), 1.81 (m, 2H), 1.95 (m, 2H), 2.03 (m, 1H), 2.13 (m, 3H), 2.40 (m, 1H), 2.66 (s, 3H), 3.31 (m, 2H), 3.47 (m, 1H), 3.63 (m, 1H), 3.86 (m, 1H), 4.77 (m, 1H), 5.11 (s, 1H), 5.50 (s, 1H), 8.47 (d, 2H).

EXAMPLE 37 trans-1-carbamoyl-4-adamantyl 3-(6-methylpyridazin-3-yl)pyrrolidine-1-carboxylate

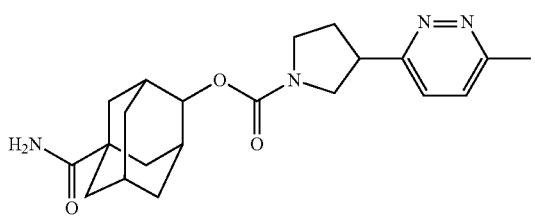 [SMILES: Cc1ccc(C2CCN(C(=O)OC3C4CC5CC3CC(C(N)=O)(C5)C4)C2)nn1]

The title compound was prepared was prepared following the procedure of Example 19 using 3-methyl-6-(pyrrolidin-3-yl)pyridazine in Step 1. Two isomers were isolated.

Isomer 1: trans-1-carbamoyl-4-adamantyl 3-(5-methylpyridin-2-yl)pyrrolidine-1-carboxylate. LC-MS Method 3 $t_R$=0.808 min, m/z=385.1; $^1$H NMR (CD$_3$OD) 1.27 (m, 1H), 1.52 (m, 2H), 1.83 (m, 2H), 1.92 (m, 5H), 2.04 (m, 3H), 2.17 (m, 1H), 2.38 (m, 1H), 2.59 (s, 3H), 3.13 (m, 1H), 3.43 (m, 1H), 3.58 (m, 1H), 3.69 (m, 2H), 3.88 (m, 1H), 7.51 (m, 2H).

Isomer 2: cis-1-carbamoyl-4-adamantyl 3-(5-methylpyridin-2-yl)pyrrolidine-1-carboxylate. LC-MS Method 3 $t_R$=0.769 min, m/z=407; $^1$H NMR (CD$_3$OD) 1.23 (m, 3H), 1.66 (m, 2H), 1.68 (m, 1H), 1.70 (m, 3H), 1.91 (m, 1H), 2.08 (m, 3H), 2.19 (m, 1H), 2.33 (m, 1H), 2.59 (s, 3H), 3.14 (m, 1H), 3.46 (m, 1H), 3.53 (m, 1H), 3.70 (m, 2H), 3.83 (m, 1H), 7.51 (m, 2H).

EXAMPLE 38

1-carbamoyl-4-adamantyl 3-(4-methylpyrimidin-2-yl)pyrrolidine-1-carboxylate

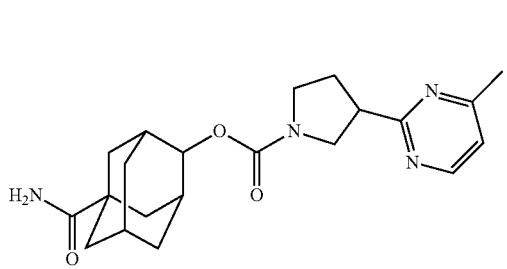 [SMILES: Cc1ccnc(C2CCN(C(=O)OC3C4CC5CC3CC(C(N)=O)(C5)C4)C2)n1]

The title compound was prepared was prepared following the procedure of Example 19 using 4-methyl-2-(pyrrolidin-3-yl)pyrimidine in Step 1. Two isomers were isolated.

Isomer 1: trans-1-carbamoyl-4-adamantyl 3-(5-methylpyridin-2-yl)pyrrolidine-1-carboxylate. LC-MS Method 3 $t_R$=1.067 min, m/z=385.3; $^1$H NMR (CDCl$_3$) 1.92 (m, 2H), 1.98 (m, 5H), 2.07 (m, 3H), 2.17 (m, 2H), 2.25 (m, 1H), 2.42 (m, 2H), 2.56 (m, 3H), 3.52 (m, 1H), 3.71 (m, 2H), 3.78 (m, 1H), 3.92 (m, 1H), 4.87 (s, 1H), 7.05 (m, 1H), 8.55 (m, 1H).

Isomer 2: cis-1-carbamoyl-4-adamantyl 3-(5-methylpyridin-2-yl)pyrrolidine-1-carboxylate. LC-MS Method 3 $t_R$=1.022 min, m/z=385.3; $^1$H NMR (CDCl$_3$) 1.74 (m, 2H), 1.87 (m, 4H), 1.89 (m, 2H), 2.03 (m, 1H), 2.16 (m, 4H), 2.35 (m, 2H), 2.52 (m, 3H), 3.52 (m, 1H), 3.73 (m, 3H), 3.92 (m, 1H), 4.85 (s, 1H), 5.28 (s, 1H), 5.62 (s, 1H), 7.04 (m, 1H), 8.54 (m, 1H).

EXAMPLE 39

1-carbamoyl-4-adamantyl 3-(5-methylpyrimidin-2-yl)pyrrolidine-1-carboxylate

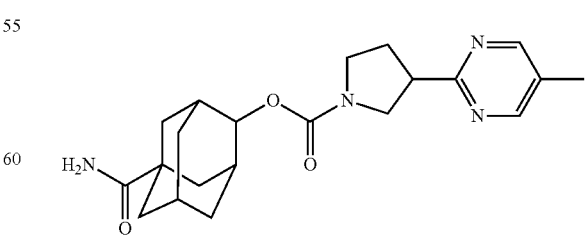

The title compound was prepared was prepared following the procedure of Example 19 using 5-methyl-2-(pyrrolidin-3-yl)pyrimidine in Step 1. Two isomers were isolated.

Isomer 1: trans-1-carbamoyl-4-adamantyl 3-(5-methylpyridin-2-yl)pyrrolidine-1-carboxylate. LC-MS Method 3 $t_R$=0.882 min, m/z=385.2; $^1$H NMR (CDCl$_3$) 1.52 (m, 2H), 1.62 (m, 2H), 1.88 (m, 2H), 2.01 (m, 7H), 2.13 (m, 2H), 2.31 (s, 3H), 2.35 (m, 1H), 3.51 (m, 1H), 3.72 (m, 3H), 3.91 (m, 1H), 4.85 (s, 1H), 5.22 (m, 1H), 5.58 (m, 1H), 8.51 (m, 2H).

Isomer 2: cis-1-carbamoyl-4-adamantyl 3-(5-methylpyridin-2-yl)pyrrolidine-1-carboxylate. LC-MS Method 3 $t_R$=0.838 min, m/z=407.2; $^1$H NMR (CDCl$_3$) 1.62 (m, 4H), 1.72 (m, 2H), 1.78 (m, 3H), 1.83 (m, 2H), 2.01 (m, 1H), 2.17 (m, 3H), 2.29 (s, 3H), 2.35 (m, 1H), 3.52 (m, 1H), 3.73 (m, 3H), 3.91 (m, 1H), 4.82 (s, 1H), 5.22 (s, 1H), 5.57 (s, 1H), 8.50 (s, 2H).

EXAMPLE 40

1-carbamoyl-4-adamantyl 3-(1,5-dimethyl-1H-pyrazol-3-yl)pyrrolidine-1-carboxylate

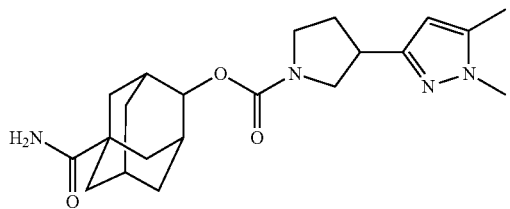 [SMILES: Cc1cc(C2CCN(C(=O)OC3C4CC5CC3CC(C(N)=O)(C5)C4)C2)nn1C]

The title compound was prepared was prepared following the procedure of Example 19 using 1,5-dimethyl-3-(pyrrolidin-3-yl)-1H-pyrazole in Step 1. Two isomers were isolated.

Isomer 1: trans-1-carbamoyl-4-adamantyl 3-(5-methylpyridin-2-yl)pyrrolidine-1-carboxylate. LC-MS Method 3 $t_R$=0.946 min, m/z=387.1; $^1$H NMR (CDCl$_3$) 1.48 (m, 2H), 1.82 (m, 2H), 1.89 (m, 5H), 1.95 (m, 4H), 2.09 (m, 2H), 2.16 (s, 3H), 3.30-3.40 (m, 3H), 3.52 (m, 1H), 3.66 (s, 3H), 3.78 (m, 1H), 4.78 (s, 1H), 5.13 (m, 1H), 5.50 (m, 1H), 5.78 (m, 1H).

Isomer 2: cis-1-carbamoyl-4-adamantyl 3-(5-methylpyridin-2-yl)pyrrolidine-1-carboxylate. LC-MS Method 3 $t_R$=0.906 min, m/z=387.1; $^1$H NMR (CDCl$_3$) 1.62 (m, 1H), 1.64 (m, 1H), 1.72 (m, 4H), 1.78 (m, 2H), 1.94 (m, 2H), 1.96-2.10 (m, 3H), 2.12 (m, 2H), 2.15 (m, 3H), 3.35 (m, 3H), 3.51 (m, 1H), 3.69 (s, 3H), 3.74 (m, 1H), 4.73 (s, 1H), 5.18 (m, 1H), 5.50 (m, 1H), 5.79 (m, 1H).

EXAMPLE 41

1-carbamoyl-4-adamantyl 3-(5-fluoropyrimidin-2-yl)pyrrolidine-1-carboxylate

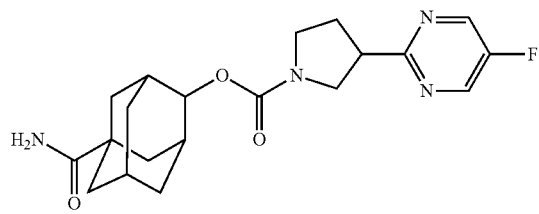 [SMILES: NC(=O)C12CC3CC(C1)C(OC(=O)N1CCC(c4ncc(F)cn4)C1)C(C3)C2]

The title compound was prepared was prepared following the procedure of Example 19 using 5-fluoro-2-(pyrrolidin-3-yl)pyrimidine in Step 1. Two isomers were isolated.

Isomer 1: trans-1-carbamoyl-4-adamantyl 3-(5-methylpyridin-2-yl)pyrrolidine-1-carboxylate. LC-MS Method 3 $t_R$=0.973 min, m/z=389; $^1$H NMR (CDCl$_3$) 1.48 (m, 2H), 1.82 (m, 2H), 1.91 (m, 4H), 1.97 (m, 3H), 2.11 (m, 2H), 2.20-2.35 (m, 2H), 3.48 (m, 1H), 3.61-3.72 (m, 3H), 3.85 (m, 1H), 4.78 (s, 1H), 5.22 (m, 1H), 5.51 (m, 1H), 8.49 (d, 2H).

Isomer 2: cis-1-carbamoyl-4-adamantyl 3-(5-methylpyridin-2-yl)pyrrolidine-1-carboxylate. LC-MS Method 3 $t_R$=0.91 min, m/z=411.1; $^1$H NMR (CDCl$_3$) 1.62 (m, 2H), 1.72 (m, 4H), 1.81 (m, 2H), 1.92 (m, 1H), 2.11 (m, 4H), 2.36 (m, 2H), 3.48 (m, 1H), 3.68 (m, 3H), 3.82 (m, 1H), 4.73 (s, 1H), 5.12 (m, 1H), 5.50 (m, 1H), 8.48 (s, 2H).

EXAMPLE 42

1-carbamoyl-4-adamantyl 3-(4-methylthiazol-2-yl)pyrrolidine-1-carboxylate

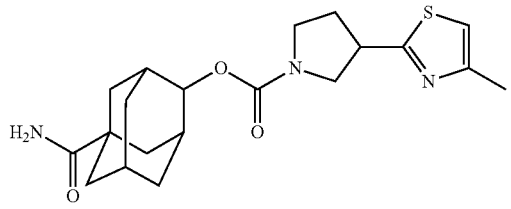 [SMILES: Cc1csc(C2CCN(C(=O)OC3C4CC5CC3CC(C(N)=O)(C5)C4)C2)n1]

The title compound was prepared was prepared following the procedure of Example 19 using 4-methyl-2-(pyrrolidin-3-yl)thiazole in Step 1. Two isomers were isolated.

Isomer 1: trans1-carbamoyl-4-adamantyl 3-(4-methylthiazol-2-yl)pyrrolidine-1-carboxylate. LC-MS Method 3 $t_R$=1.127 min, m/z=390.3; $^1$H NMR (CDCl$_3$) 1.45 (m, 2H), 1.83 (m, 2H), 1.88 (m, 4H), 1.95 (m, 3H), 2.10 (m, 2H), 2.17 (m, 1H), 2.33 (m, 1H), 2.37 (s, 3H), 3.45 (m, 1H), 3.58 (m, 2H), 3.73 (m, 1H), 3.87 (m, 1H), 4.80 (s, 1H), 5.48 (s, 1H), 5.59 (s, 1H), 6.72 (s, 1H).

Isomer 2: cis-1-carbamoyl-4-adamantyl 3-(4-methylthiazol-2-yl)pyrrolidine-1-carboxylate. LC-MS Method 3 $t_R$=0.928 min, m/z=390; $^1$H NMR (CDCl$_3$) 1.65 (m, 1H), 1.73 (m, 4H), 1.79 (m, 2H), 1.96 (m, 1H), 2.04 (m, 2H), 2.13 (m, 3H), 2.19 (m, 1H), 2.33 (m, 4H), 3.43 (m, 1H), 3.60 (m, 2H), 3.68 (m, 1H), 3.87 (m, 1H), 4.77 (s, 1H), 5.19 (m, 1H), 5.51 (m, 1H), 6.72 (s, 1H)

EXAMPLE 43

1-carbamoyl-4-adamantyl 3-(4,6-dimethylpyrimidin-2-yl)pyrrolidine-1-carboxylate

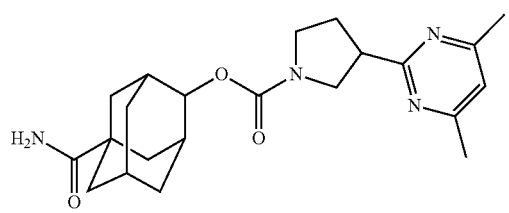 [SMILES: Cc1cc(C)nc(C2CCN(C(=O)OC3C4CC5CC3CC(C(N)=O)(C5)C4)C2)n1]

The title compound was prepared was prepared following the procedure of Example 19 using 4,6-dimethyl-2-(pyrrolidin-3-yl)pyrimidine in Step 1. Two isomers were isolated.

Isomer 1: trans-1-carbamoyl-4-adamantyl 3-(4,6-dimethylpyrimidin-2-yl)pyrrolidine-1-carboxylate. LC-MS Method 3 $t_R$=0.821 min, m/z=399; $^1$H NMR (CDCl$_3$) 1.48 (m, 3H), 1.82 (m, 2H), 1.88 (m, 4H), 1.98 (m, 2H), 2.08 (m, 2H), 2.33 (m, 2H), 2.38 (m, 6H), 3.31 (m, 1H), 3.45 (m, 2H), 3.57 (m, 1H), 3.68 (m, 1H), 3.82 (m, 1H), 4.78 (s, 1H), 5.22 (m, 1H), 5.52 (m, 1H), 6.86 (m, 1H).

Isomer 2: cis-1-carbamoyl-4-adamantyl 3-(4,6-dimethylpyrimidin-2-yl)pyrrolidine-1-carboxylate. LC-MS Method 3 $t_R$=0.799 min, m/z=399.2; $^1$H NMR (CDCl$_3$) 1.36 (m, 1H), 1.63 (m, 2H), 1.71 (m, 4H), 1.78 (m, 2H), 1.92 (m, 1H), 2.13 (m, 3H), 2.25 (m, 2H), 2.38 (m, 6H), 3.43 (m, 1H), 3.53 (m, 1H), 3.65 (m, 1H), 3.75 (m, 1H), 3.80 (m, 1H), 4.73 (s, 1H), 5.22 (m, 1H), 5.52 (m, 1H), 6.83 (m, 1H).

EXAMPLE 44

1-carbamoyl-4-adamantyl 3-(5-methoxypyrimidin-2-yl)pyrrolidine-1-carboxylate

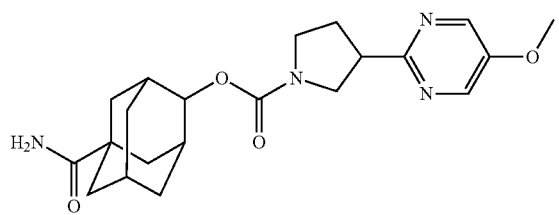 [SMILES: COc1cnc(C2CCN(C(=O)OC3C4CC5CC3CC(C(N)=O)(C5)C4)C2)nc1]

The title compound was prepared was prepared following the procedure of Example 19 using 5-methoxy-2-(pyrrolidin-3-yl)pyrimidine in Step 1. Two isomers were isolated.

Isomer 1: trans-1-carbamoyl-4-adamantyl 3-(5-methylpyridin-2-yl)pyrrolidine-1-carboxylate. LC-MS Method 3 $t_R$=0.97 min, m/z=401.1; $^1$H NMR (CDCl$_3$) 1.44 (m, 2H), 1.82 (m, 2H), 1.89 (m, 5H), 1.92 (m, 2H), 2.01 (m, 1H), 2.11 (m, 2H), 2.26 (m, 2H), 3.45 (m, 1H), 3.63 (m, 3H), 3.83 (s, 3H), 4.79 (s, 1H), 5.16 (m, 1H), 5.51 (m, 1H), 8.29 (s, 2H).

Isomer 2: cis-1-carbamoyl-4-adamantyl 3-(5-methylpyridin-2-yl)pyrrolidine-1-carboxylate. LC-MS Method 3 $t_R$=0.92 min, m/z=423.1; $^1$H NMR (CDCl$_3$) 1.63 (m, 2H), 1.71 (m, 4H), 1.79 (m, 2H), 1.93 (m, 2H), 2.14 (m, 4H), 2.22 (m, 2H), 3.45 (m, 1H), 3.63 (m, 3H), 3.81 (s, 3H), 4.76 (s, 1H), 5.11 (m, 1H), 5.51 (m, 1H), 8.28 (s, 2H).

EXAMPLE 45

1-carbamoyl-4-adamantyl 2-(5-chloropyrimidin-2-yl)pyrrolidine-1-carboxylate

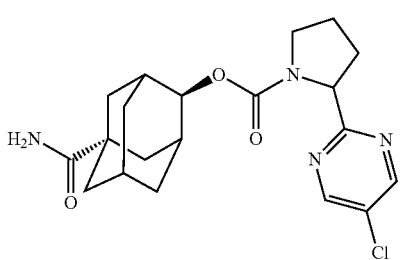 [SMILES: NC(=O)[C@]12CC3CC(C1)[C@@H](OC(=O)N1CCCC1c1ncc(Cl)cn1)C(C3)C2]

The title compound was prepared was prepared following the procedure of Example 19 using 5-chloro-2-(pyrrolidin-2-yl)pyrimidine in Step 1. The longer $t_R$ isomer was isolated by prep HPLC. LC-MS Method 1 $t_R$=1.35 min, m/z=405.

EXAMPLE 46

4-((3-(5-chloropyrimidin-2-yl)pyrrolidine-1-carbonyl)oxy)adamantane-1-carboxylic acid

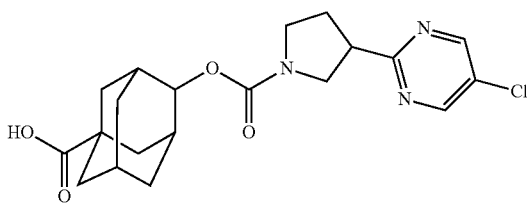 [SMILES: O=C(OC1C2CC3CC1CC(C(=O)O)(C3)C2)N1CCC(c2ncc(Cl)cn2)C1]

The product of Example 26 Step 2 was separated into two isomers by prep HPLC.

Isomer 1: trans-4-((3-(5-chloropyrimidin-2-yl)pyrrolidine-1-carbonyl)oxy)adamantane-1-carboxylic acid. LC-MS Method 1 $t_R$=1.63 min, m/z=406; $^1$H NMR (CD$_3$OD) 1.52-1.62 (m, 2H), 1.90-2.15 (m, 11H), 2.20-2.35 (m, 1H), 2.35-2.45 (m, 1H), 3.45-3.95 (m, 5H), 4.78 (s, 1H), 8.77 (s, 2H).

Isomer 2: cis-4-((3-(5-chloropyrimidin-2-yl)pyrrolidine-1-carbonyl)oxy)adamantane-1-carboxylic acid. LC-MS Method 1 $t_R$=1.52 min, m/z=406; $^1$H NMR (CD$_3$OD) 1.70-2.00 (m, 9H), 2.10-2.50 (m, 6H), 3.45-3.95 (m, 5H), 4.77 (s, 1H), 8.76 (s, 2H).

EXAMPLE 47

1-carbamoyl-4-adamantyl 3-(5-carbamoylpyrimidin-2-yl)pyrrolidine-1-carboxylate

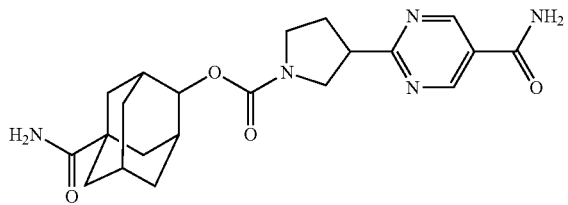 [SMILES: NC(=O)c1cnc(C2CCN(C(=O)OC3C4CC5CC3CC(C(N)=O)(C5)C4)C2)nc1]

The title compound was prepared was prepared following the procedure of Example 19 using methyl 2-(pyrrolidin-3-yl)pyrimidine-5-carboxylate in Step 1. Two isomers were isolated.

Isomer 1: cis-1-carbamoyl-4-adamantyl 3-(5-methylpyridin-2-yl)pyrrolidine-1-carboxylate. LC-MS Method 3 $t_R$=0.828 min, m/z=436.1; $^1$H NMR (CD$_3$OD) 1.72 (m, 2H), 1.82 (m, 2H), 1.88 (m, 4H), 2.03 (m, 1H), 2.17 (m, 4H), 2.34 (m, 1H), 2.42 (m, 1H), 3.55 (m, 1H), 3.62 (m, 1H), 3.81-3.99 (m, 3H), 4.79 (s, 1H), 9.16 (s, 2H).

Isomer 2: trans-1-carbamoyl-4-adamantyl 3-(5-methylpyridin-2-yl)pyrrolidine-1-carboxylate. LC-MS Method 3 $t_R$=0.845 min, m/z=436; $^1$H NMR (CD$_3$OD) 1.61 (m, 2H), 1.92 (m, 2H), 2.05 (m, 5H), 2.16 (m, 4H) 2.35 (m, 1H), 2.48

(m, 1H), 3.51 (m, 1H), 3.62 (m, 1H), 3.72 (m, 1H), 3.81-3.99 (m, 3H), 4.82 (m, 1H), 9.16 (m, 2H).

EXAMPLE 48

1-carbamoyl-4-adamantyl 3-(4-(trifluoromethyl)pyrimidin-2-yl)pyrrolidine-1-carboxylate

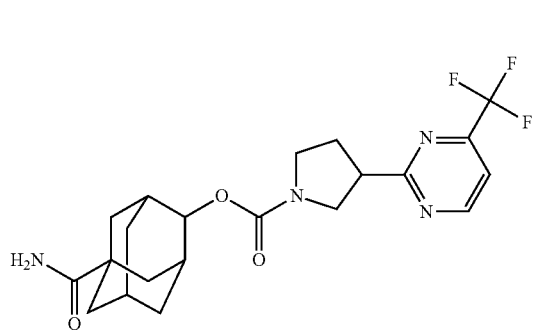 [SMILES: NC(=O)C12CC3CC(C1)C(OC(=O)N1CCC(c4nccc(C(F)(F)F)n4)C1)C(C3)C2]

The title compound was prepared was prepared following the procedure of Example 19 using 2-(pyrrolidin-3-yl)-4-(trifluoromethyl)pyrimidine in Step 1. Two isomers were isolated.

Isomer 1: trans-1-carbamoyl-4-adamantyl 3-(4-(trifluoromethyl)pyrimidin-2-yl)pyrrolidine-1-carboxylate. LC-MS Method 3 $t_R$=1.236 min, m/z=439.3; $^1$H NMR (CDCl$_3$) 1.48 (m, 2H), 1.82 (m, 2H), 1.88 (m, 4H), 1.95 (m, 3H), 2.11 (m, 2H), 2.32 (m, 2H), 3.48 (m, 1H), 3.68 (m, 1H), 3.72 (m, 2H), 3.88 (m, 1H), 4.79 (s, 1H), 5.23 (s, 1H), 5.52 (s, 1H), 7.46 (t, 1H), 8.89 (t, 1H).

Isomer 2: cis-1-carbamoyl-4-adamantyl 3-(4-(trifluoromethyl)pyrimidin-2-yl)pyrrolidine-1-carboxylate. LC-MS Method 3 $t_R$=1.113 min, m/z=461; $^1$H NMR (CDCl$_3$) 1.63 (m, 2H), 1.72 (m, 4H), 1.78 (m, 2H), 1.95 (m, 1H), 2.11 (m, 4H), 2.35 (m, 2H), 3.48 (m, 1H), 3.61 (m, 1H), 3.72 (m, 2H), 3.88 (m, 1H), 4.77 (s, 1H), 5.16 (m, 1H), 5.51 (m, 1H), 7.45 (t, 1H), 8.88 (t, 1H).

EXAMPLE 49 trans-1-carbamoyl-4-adamantyl 3-(2-hydroxy-2-methylpropyl)-3-phenylpyrrolidine-1-carboxylate

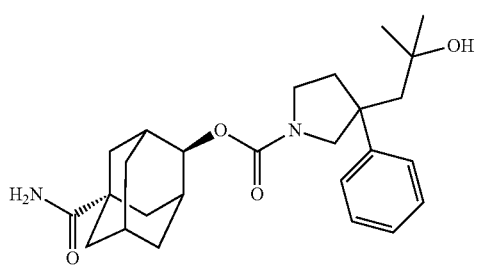 [SMILES: CC(C)(O)CC1(c2ccccc2)CCN(C(=O)O[C@H]2C3CC4CC2C[C@](C(N)=O)(C4)C3)C1]

The title compound was prepared following the procedure of Example 19 using 2-methyl-1-(3-phenylpyrrolidin-3-yl)propan-2-ol in Step 1. LC-MS Method 1 $t_R$=1.52 min, m/z=441; $^1$H NMR (CD$_3$OD) 0.74 (d, 3H), 0.94 (d, 3H), 1.45-1.67 (m, 2H) 1.85-2.38 (m, 15H), 2.94-3.08 (m, 1H), 3.35-3.60 (m, 2H), 4.18-4.32 (m, 1H), 4.73-4.82 (m, 1H), 7.18-7.40 (m, 5H).

EXAMPLE 50

(R)-2-adamantyl 2-(4-(pyridin-4-yl)thiazol-2-yl)pyrrolidine-1-carboxylate

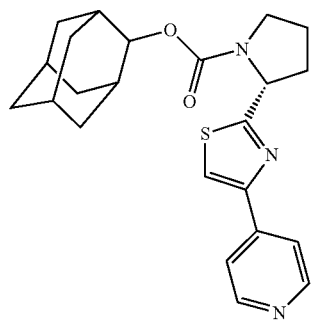 [SMILES: O=C(OC1C2CC3CC(C2)CC1C3)N1CCC[C@@H]1c1nc(-c2ccncc2)cs1]

The title compound was prepared following the procedure of Example 7 using (R)-4-(pyridin-4-yl)-2-(pyrrolidin-2-yl)thiazole. LC-MS Method 1 $t_R$=1.53 min, m/z=410.

EXAMPLE 51

2-adamantyl 3-(4-(pyridin-4-yl)thiazol-2-yl)pyrrolidine-1-carboxylate

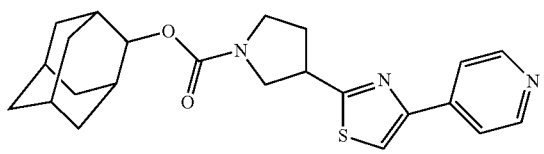 [SMILES: O=C(OC1C2CC3CC(C2)CC1C3)N1CCC(c2nc(-c3ccncc3)cs2)C1]

The title compound was prepared following the procedure of Example 7 using 4-(pyridin-4-yl)-2-(pyrrolidin-3-yl)thiazole. LC-MS Method 1 $t_R$=1.53 min, m/z=410; $^1$H NMR (CD$_3$OD) 1.53-1.68 (m, 2H), 1.75-2.15 (m, 12H), 2.30-2.42 (m, 1H), 2.44-2.57 (m, 1H), 3.50-4.10 (m, 5H), 4.81 (s, 1H), 8.54 (d, 2H), 8.66 (s, 1H), 8.83 (d, 2H).

EXAMPLE 52

(R)-4-(2-(1-((2-adamantyloxy)carbonyl)pyrrolidin-2-yl)thiazol-4-yl)pyridine 1-oxide

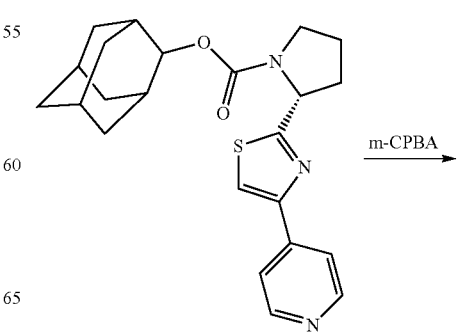

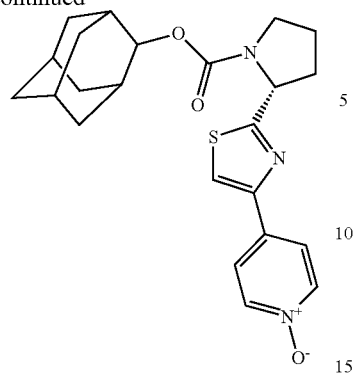

A stirred solution of 2-(4-(pyridin-4-yl)thiazol-2-yl)pyrrolidine-1-carboxylate (22 mg, 0.054 mmol) in CH₂Cl₂ (5 mL) was treated with m-CPBA (15 mg, ≤70% by wt, ≤0.061 mmol). The mixture was stirred at rt for 18 h. A ChemElut cartridge was wetted with satd aq NaHCO₃ (5 mL) and allowed to stand for 5 min. The reaction mixture was applied to the cartridge and eluted with CH₂Cl₂ (50 mL). The eluate was concentrated to afford an oil (23 mg) which was purified by prep HPLC to afford the title compound (7.4 mg, 32%) as an oil. LC-MS Method 1 $t_R$=1.75 min, m/z=426.

EXAMPLE 53

(R)-2-adamantyl 2-(4-(1-methyl-2-oxo-1,2-dihydropyridin-4-yl)thiazol-2-yl)pyrrolidine-1-carboxylate

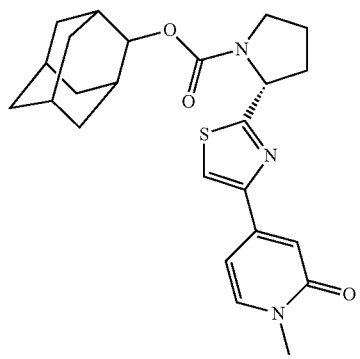 [SMILES: Cn1ccc(-c2csc([C@H]3CCCN3C(=O)OC3C4CC5CC(C4)CC3C5)n2)cc1=O]

The title compound was prepared following the procedure of Example 7 using (R)-1-methyl-4-(2-(pyrrolidin-2-yl)thiazol-4-yl)pyridin-2(1H)-one. LC-MS Method 1 $t_R$=1.82 min, m/z=440.

EXAMPLE 54

(R)-trans-1-carbamoyl-4-adamantyl 2-(4-(2-oxo-1,2-dihydropyridin-4-yl)thiazol-2-yl)pyrrolidine-1-carboxylate

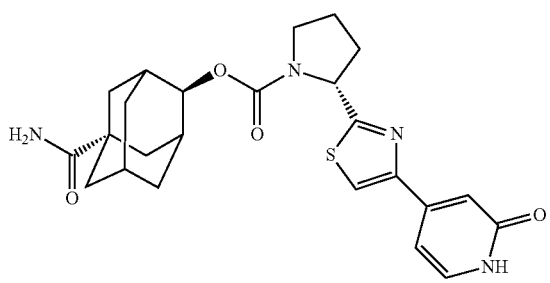 [SMILES: NC(=O)[C@]12CC3CC(C1)[C@@H](OC(=O)N1CCC[C@@H]1c1nc(-c4cc[nH]c(=O)c4)cs1)C(C3)C2]

The title compound was prepared following the procedure of Example 19 using (R)-4-(2-(pyrrolidin-2-yl)thiazol-4-yl)pyridin-2(1H)-one in Step 1. LC-MS Method 2 $t_R$=4.6 min, m/z=469; ¹H NMR (CD₃OD, 40° C.) [selected resonances] 6.90-7.96 (d, 1H), 7.13 (s, 1H), 7.46 (d, 1H), 8.04 (s, 1H).

EXAMPLE 55

(R)-trans-1-carbamoyl-4-adamantyl 2-(4-(1-methyl-2-oxo-1,2-dihydropyridin-4-yl)thiazol-2-yl)pyrrolidine-1-carboxylate

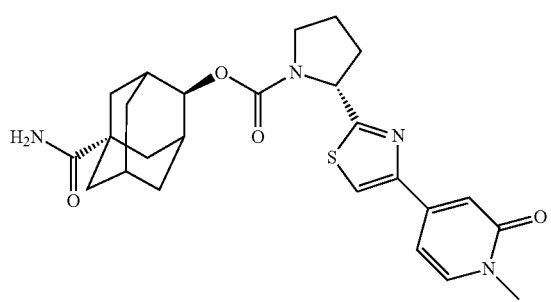 [SMILES: Cn1ccc(-c2csc([C@H]3CCCN3C(=O)O[C@H]3C4CC5CC3C[C@](C(N)=O)(C5)C4)n2)cc1=O]

The title compound was prepared following the procedure of Example 19 using (R)-1-methyl-4-(2-(pyrrolidin-2-yl)thiazol-4-yl)pyridin-2(1H)-one in Step 1. LC-MS Method 2 $t_R$=4.93 min, m/z=483; ¹H NMR (CD₃OD, 50° C.) [selected resonances] 3.58 (s, 3H), 4.77 (s, 1H), 5.25-5.35 (m, 1H), 7.91 (d, 1H), 7.14 (s, 1H), 7.64 (d, 1H), 8.00 (s, 1H).

EXAMPLE 56 trans-1-carbamoyl-4-adamantyl 3-(4-(1-methyl-2-oxo-1,2-dihydropyridin-4-yl)thiazol-2-yl)pyrrolidine-1-carboxylate

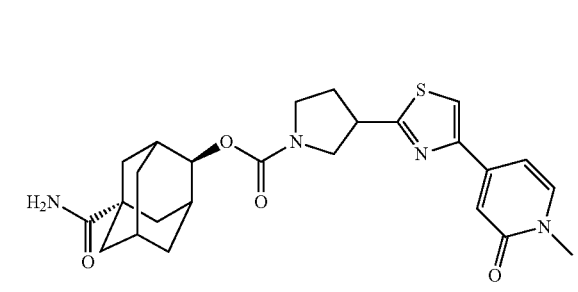 [SMILES: Cn1ccc(-c2csc(C3CCN(C(=O)O[C@H]4C5CC6CC4C[C@](C(N)=O)(C6)C5)C3)n2)cc1=O]

The title compound was prepared following the procedure of Example 19 using 1-methyl-4-(2-(pyrrolidin-3-yl)thiazol-4-yl)pyridin-2(1H)-one in Step 1. LC-MS Method 2 $t_R$=5.23 min, m/z=483; $^1$H NMR (CD$_3$OD) 1.50-163 (m, 2H), 1.80-2.20 (11H), 2.22-2.38 (m, 1H), 2.40-2.55 (m, 1H), 3.59 (s, 3H), 3.45-4.00 (5H), 4.80 (s, 1H), 6.97 (d, 1H), 7.18 (s, 1H), 7.72 (d, 1H), 8.08 (s, 1H).
EXAMPLE 57
1-carbamoyl-4-adamantyl 3-(5-(1-methyl-2-oxo-1,2-dihydropyridin-4-yl)pyrimidin-2-yl)pyrrolidine-1-carboxylate
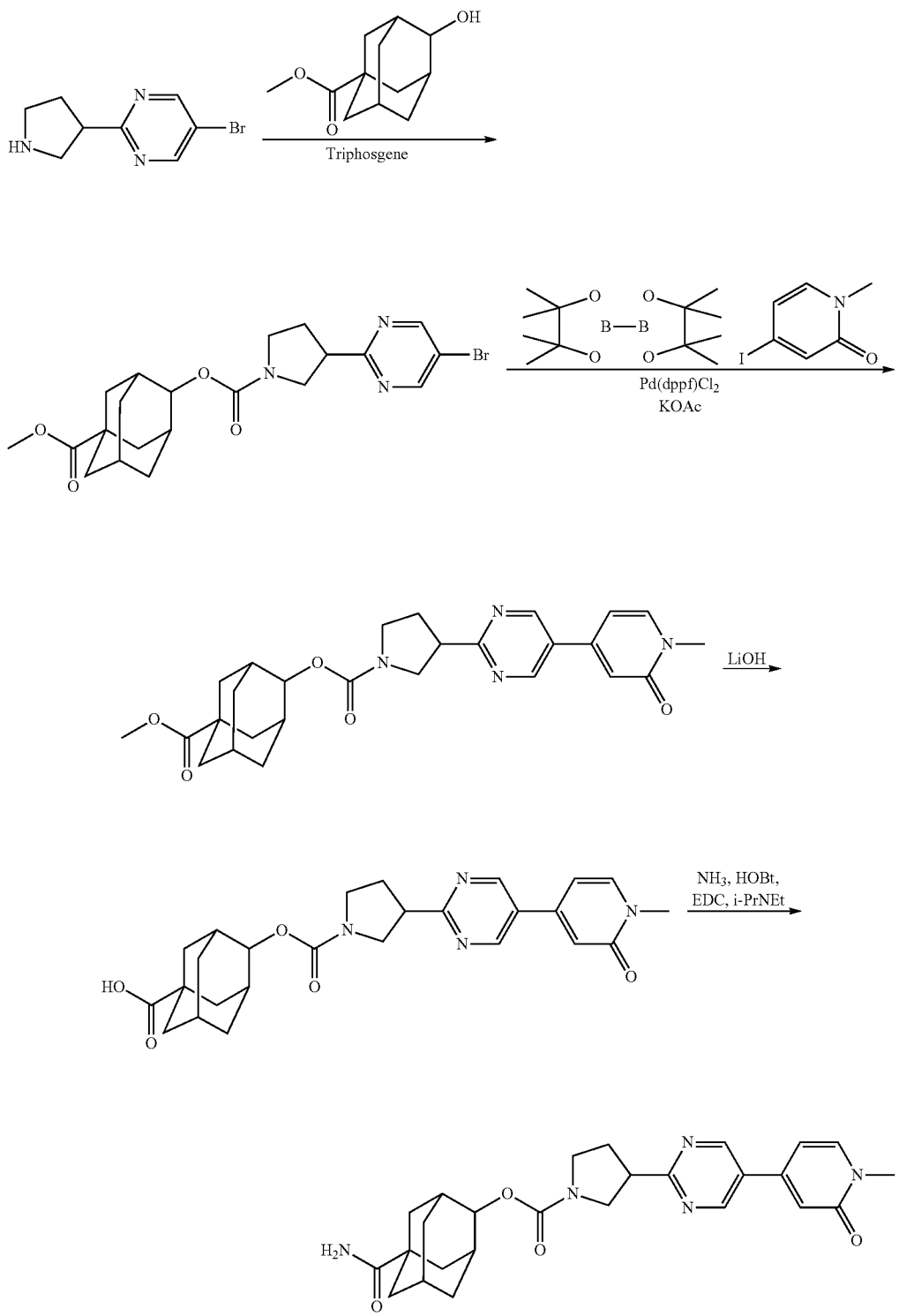

Step 1

A procedure analogous to that described in Example 19 Step 1 was followed using 5-bromo-2-(pyrrolidin-3-yl)pyrimidine to afford 1-(methoxycarbonyl)adamantan-4-yl 3-(5-bromopyrimidin-2-yl)pyrrolidine-1-carboxylate.

Step 2

To a solution of 1-(methoxycarbonyl)adamantan-4-yl 3-(5-bromopyrimidin-2-yl)pyrrolidine-1-carboxylate (24 mg, 0.05 mmol), 4-iodo-1-methylpyridin-2(1H)-one (25 mg, 0.1 mmol), 4,4,4',4',5,5,5',5'-octamethyl-2,2'-bi(1,3,2-dioxaborolane) (38.1 mg, 0.15 mmol), KOAc (49 mg, 0.5 mmol) and Pd(dppf)Cl$_2$ (1 mg, 0.001 mmol) in DMSO (5 mL) under nitrogen was heated to 100 C for 2 h. The reaction mixture was treated with water and extracted with EtOAc (10 mL×3). The combined organic layers were dried over sodium sulfate, filtered and concentrated to afford an oil which was purified by preparative TLC to afford 1-(methoxycarbonyl)adamantan-4-yl 3-(5-(1-methyl-2-oxo-1,2-dihydropyridin-4-yl)pyrimidin-2-yl)pyrrolidine-1-carboxylate (36 mg, 36%).

Step 3

To a solution of 1-(methoxycarbonyl)adamantan-4-yl 3-(5-(1-methyl-2-oxo-1,2-dihydropyridin-4-yl)pyrimidin-2-yl)pyrrolidine-1-carboxylate (36 mg, 0.073 mmol) in MeOH (6 mL)/water (2 mL) was added LiOH (22 mg, 0.73 mmol). The reaction mixture was heated to reflux for 1 h. The formed mixture was concentrated to give an oil which was adjusted pH=5 by 0.5 M HCl and extracted with EtOAc (10 mL×3). The combined organic layers were dried over sodium sulfate, filtered and concentrated to afford 4-((3-(5-(1-methyl-2-oxo-1,2-dihydropyridin-4-yl)pyrimidin-2-yl)pyrrolidine-1-carbonyl)oxy)adamantane-1-carboxylic acid (20 mg, 55%).

Step 4

A solution of 4-((3-(5-(1-methyl-2-oxo-1,2-dihydropyridin-4-yl)pyrimidin-2-yl)pyrrolidine-1-carbonyl)oxy)adamantane-1-carboxylic acid (20 mg, 0.04 mmol), HOBt (11.3 mg, 0.08 mmol), EDCl (16.5 mg, 0.08 mmol) and i-Pr$_2$NEt (27 mg, 0.21 mmol) in dichloromethane (5 mL) was stirred overnight under ammonia gas. The reaction mixture was concentrated to afford an oil which was purified by basic preparative HPLC to afford two isomers:

Isomer 1: trans-1-carbamoyl-4-adamantyl 3-(5-(1-methyl-2-oxo-1,2-dihydropyridin-4-yl)pyrimidin-2-yl)pyrrolidine-1-carboxylate. (1.5 mg, yield: 7.5%) LC-MS Method 3 $t_R$=0.771 min, m/z=478.2; $^1$H NMR (CDCl$_3$) 1.19 (m, 1H), 1.41 (m, 1H), 1.58 (m, 1H), 1.82 (m, 2H), 1.89 (m, 3H), 1.93 (m, 2H), 2.11 (m, 4H), 2.31 (m, 1H), 3.46 (m, 1H), 3.57 (s, 3H), 3.66 (m, 1H), 3.72 (m, 2H), 3.88 (m, 1H), 4.79 (s, 1H), 5.11 (m, 1H), 5.51 (m, 1H), 6.30 (m, 1H), 6.73 (d, 1H), 7.37 (d, 1H), 8.81 (d, 2H)

Isomer 2: cis-1-carbamoyl-4-adamantyl 3-(5-(1-methyl-6-oxo-1,6-dihydropyridin-3-yl)pyrimidin-2-yl)pyrrolidine-1-carboxylate (0.7 mg, 3.5%). LC-MS Method 3 $t_R$=0.753 min, m/z=478.2; $^1$H NMR (CDCl$_3$) 1.28 (m, 2H), 1.38 (m, 1H), 1.62 (m, 1H), 1.72 (s, 3H), 1.78 (s, 1H), 1.95 (m, 2H), 2.15 (m, 3H), 2.33 (m, 1H), 3.48 (m, 1H), 3.55 (s, 3H), 3.65 (m, 1H), 3.72 (m, 2H), 3.89 (m, 1H), 4.77 (s, 1H), 5.13 (m, 1H), 5.52 (m, 1H), 6.32 (d, 1H), 6.72 (s, 1H), 7.38 (d, 1H), 8.80 (s, 2H).

EXAMPLE 58

1-carbamoyl-4-adamantyl 3-(5-(1-methyl-6-oxo-1,6-dihydropyridin-3-yl)pyrimidin-2-yl)pyrrolidine-1-carboxylate

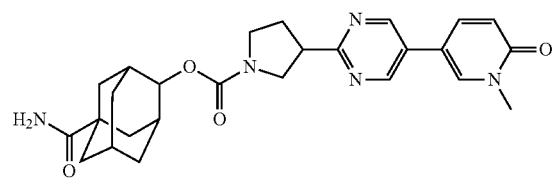 [SMILES: Cn1cc(-c2cnc(C3CCN(C(=O)OC4C5CC6CC4CC(C(N)=O)(C6)C5)C3)nc2)ccc1=O]

The title compound was prepared following procedures analogous to those described in Example 57 using 5-bromo-1-methylpyridin-2(1H)-one in Step 2. Two isomers were isolated.

Isomer 1: trans-1-carbamoyl-4-adamantyl 3-(5-(1-methyl-6-oxo-1,6-dihydropyridin-3-yl)pyrimidin-2-yl)pyrrolidine-1-carboxylate. LC-MS Method 3 $t_R$=0.829 min, m/z=478.3; $^1$H NMR (CDCl$_3$) 1.53 (m, 2H), 1.89-2.09 (m, 9H), 2.13 (m, 2H), 2.38 (m, 2H), 3.55 (m, 1H), 3.62 (s, 3H), 3.73 (m, 3H), 3.91 (m, 1H), 4.87 (s, 1H), 5.21 (m, 1H), 5.57 (m, 1H), 6.73 (d, 1H), 7.53 (m, 2H), 8.72 (d, 2H)

Isomer 2: cis-1-carbamoyl-4-adamantyl 3-(5-(1-methyl-2-oxo-1,2-dihydropyridin-4-yl)pyrimidin-2-yl)pyrrolidine-1-carboxylate. LC-MS Method 3 $t_R$=0.778 min, m/z=478.1; $^1$H NMR (CDCl$_3$) 1.71 (m, 2H), 1.83 (m, 6H), 2.02 (m, 1H), 2.16 (m, 4H), 2.38 (m, 2H), 3.52 (m, 1H), 3.63 (s, 3H), 3.71 (m, 3H), 3.92 (m, 1H), 4.83 (s, 1H), 5.19 (m, 1H), 5.58 (m, 1H), 6.73 (d, 1H), 7.57 (m, 2H), 8.74 (s, 2H).

EXAMPLE 59

(R)-1-carbamoyl-4-adamantyl 3-(7-chloro-2-methyl-1H-benzo[d]imidazol-1-yl)pyrrolidine-1-carboxylate

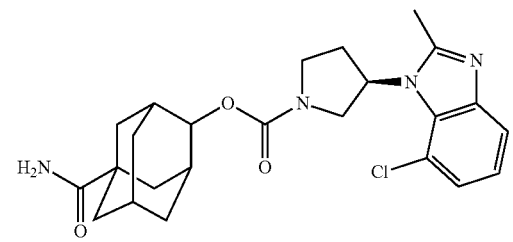 [SMILES: Cc1nc2cccc(Cl)c2n1[C@@H]1CCN(C(=O)OC2C3CC4CC2CC(C(N)=O)(C4)C3)C1]

The title compound was prepared following the procedure of Example 19 using (R)-7-chloro-2-methyl-1-(pyrrolidin-3-yl)-1H-benzo[d]imidazole in Step 1. The product was isolated as a mixture of cis and trans isomers. LC-MS Method 2 $t_R$=4.53 min, m/z=457; $t_R$=4.78 min, m/z=457.

EXAMPLE 60

(S)-trans-1-carbamoyl-4-adamantyl 3-(2-oxo-2,3-dihydro-1H-benzo[d]imidazol-1-yl)pyrrolidine-1-carboxylate

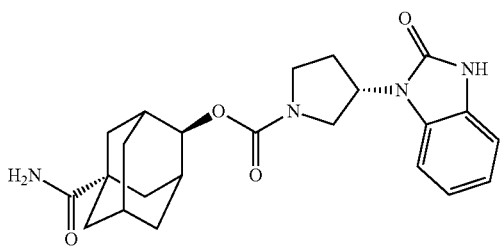 [SMILES: NC(=O)[C@]12CC3CC(C1)[C@@H](OC(=O)N1CC[C@H](n4c(=O)[nH]c5ccccc54)C1)C(C3)C2]

The title compound was prepared following the procedure of Example 19 using (S)-1-(pyrrolidin-3-yl)-1H-benzo[d]imidazol-2(3H)-one in Step 1. LC-MS Method 1 $t_R$=1.25 min, m/z=425; $^1$H NMR (CD$_3$OD) 1.50-1.65 (m, 2H), 1.85-2.20 (m, 11H), 2.23-2.33 (m, 1H), 2.54-2.72 (m, 1H), 3.45-4.05 (m, 4H), 4.83 (s, 1H), 5.08-5.19 (m, 1H), 7.08-7.14 (m, 3H), 7.16-7.21 (m, 1H).

EXAMPLE 61

(R)-trans-1-carbamoyl-4-adamantyl 3-(2-oxo-2,3-dihydro-1H-benzo[d]imidazol-1-yl)pyrrolidine-1-carboxylate

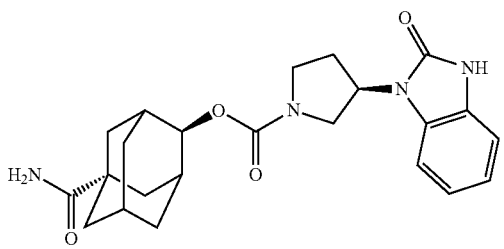 [SMILES: NC(=O)[C@]12CC3CC(C1)[C@@H](OC(=O)N1CC[C@@H](n4c(=O)[nH]c5ccccc54)C1)C(C3)C2]

The title compound was prepared following the procedure of Example 19 using (R)-1-(pyrrolidin-3-yl)-1H-benzo[d]imidazol-2(3H)-one in Step 1. LC-MS Method 2 $t_R$=5.15 min, m/z=425; $^1$H NMR (CDCl$_3$) 1.45-1.60 (m, 2H), 1.80-2.40 (m, 12H), 2.60-2.74 (m, 1H), 3.48-3.61 (m, 1H), 4.80-4.95 (m, 3H), 4.89 (s, 3H), 5.07-5.20 (m, 1H), 5.68 (br s, 1H), 5.89 (br s, 1H), 7.01-7.17 (m, 4H), 9.37-9.47 (m, 1H).

EXAMPLE 62

(R)-trans-1-carbamoyl-4-adamantyl 3-(3-methyl-2-oxo-2,3-dihydro-1H-benzo[d]imidazol-1-yl)pyrrolidine-1-carboxylate

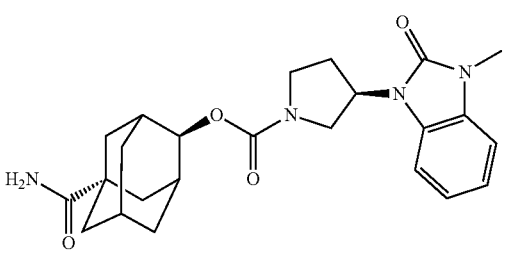 [SMILES: Cn1c(=O)n([C@@H]2CCN(C(=O)O[C@H]3C4CC5CC3C[C@](C(N)=O)(C5)C4)C2)c2ccccc21]

The title compound was prepared following the procedure of Example 19 using (R)-1-methyl-3-(pyrrolidin-3-yl)-1H-benzo[d]imidazol-2(3H)-one in Step 1. LC-MS Method 1 $t_R$=1.38 min, m/z=439; $^1$H NMR (CD$_3$OD) 1.50-1.65 (m, 2H), 1.85-2.35 (m, 12H), 2.55-2.70 (m, 1H), 3.41 (s, 3H), 3.45-3.65 (m, 1H), 3.75-4.00 (m, 3H), 4.82 (s, 1H), 5.07-5.18 (m, 1H), 7.10-7.22 (m, 4H).

EXAMPLE 63

(S)-trans-1-carbamoyl-4-adamantyl 3-(5-fluoro-2-oxo-2,3-dihydro-1H-benzo[d]imidazol-1-yl)pyrrolidine-1-carboxylate

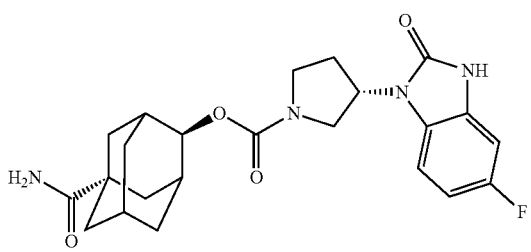 [SMILES: NC(=O)[C@]12CC3CC(C1)[C@@H](OC(=O)N1CC[C@H](n4c(=O)[nH]c5cc(F)ccc54)C1)C(C3)C2]

The title compound was prepared following the procedure of Example 19 using (S)-5-fluoro-1-(pyrrolidin-3-yl)-1H-benzo[d]imidazol-2(3H)-one in Step 1. LC-MS Method 2 $t_R$=5.45 min, m/z=443; $^1$H NMR (CD$_3$OD, 40° C.) 1.48-1.63 (m, 2H), 1.85-2.20 (m, 11H), 2.23-2.38 (m, 1H), 2.50-2.70 (m, 1H), 3.45-3.65 (m, 1H), 3.72-3.98 (m, 3H), 4.82 (s, 1H), 5.00-5.15 (m, 1H), 6.77-6.88 (m, 2H), 7.02-7.10 (m, 1H).

EXAMPLE 64

(S)-trans-1-carbamoyl-4-adamantyl 3-(5-cyano-2-oxo-2,3-dihydro-1H-benzo[d]imidazol-1-yl)pyrrolidine-1-carboxylate

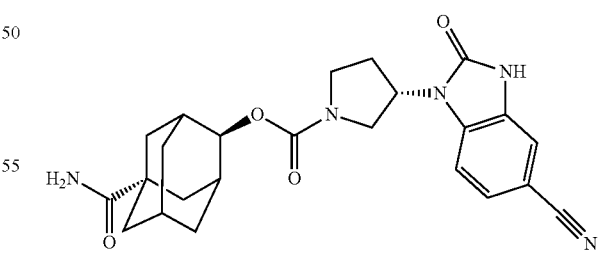

The title compound was prepared following the procedure of Example 19 using (S)-2-oxo-1-(pyrrolidin-3-yl)-2,3-dihydro-1H-benzo[d]imidazole-5-carbonitrile in Step 1. LC-MS Method 1 $t_R$=1.23 min, m/z=450; $^1$H NMR (CD$_3$OD) 1.50-1.65 (m, 2H), 1.80-2.20 (m, 11H), 2.25-2.38 (m, 1H), 2.55-2.70 (m, 1H), 3.45-4.05 (m, 4H), 4.83 (s, 1H), 5.05-5.18 (m, 1H), 7.33-7.39 (m, 2H), 7.43-7.47 (d, 1H).

EXAMPLE 65

(R)-trans-1-carbamoyl-4-adamantyl 3-(6-cyano-2-oxo-2,3-dihydro-1H-benzo[d]imidazol-1-yl)pyrrolidine-1-carboxylate

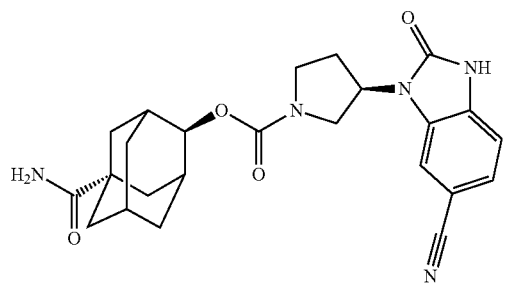 [SMILES: N#Cc1ccc2[nH]c(=O)n([C@@H]3CCN(C(=O)O[C@H]4C5CC6CC4C[C@](C(N)=O)(C6)C5)C3)c2c1]

The title compound was prepared following the procedure of Example 19 using (R)-2-oxo-3-(pyrrolidin-3-yl)-2,3-dihydro-1H-benzo[d]imidazole-5-carbonitrile in Step 1. LC-MS Method 1 $t_R$=1.23 min, m/z=450; $^1$H NMR (CD$_3$OD) 1.52-1.67 (m, 2H), 1.85-2.20 (m, 11H), 2.25-2.38 (m, 1H), 2.53-2.70 (m, 1H), 3.45-4.05 (m, 4H), 4.83 (s, 1H), 5.04-5.17 (m, 1H), 7.18 (d, 1H), 7.43 (d, 1H), 7.56 (s, 1H).

EXAMPLE 66

(R)-trans-1-carbamoyl-4-adamantyl 3-(5-cyano-2-oxo-2,3-dihydro-1H-benzo[d]imidazol-1-yl)pyrrolidine-1-carboxylate

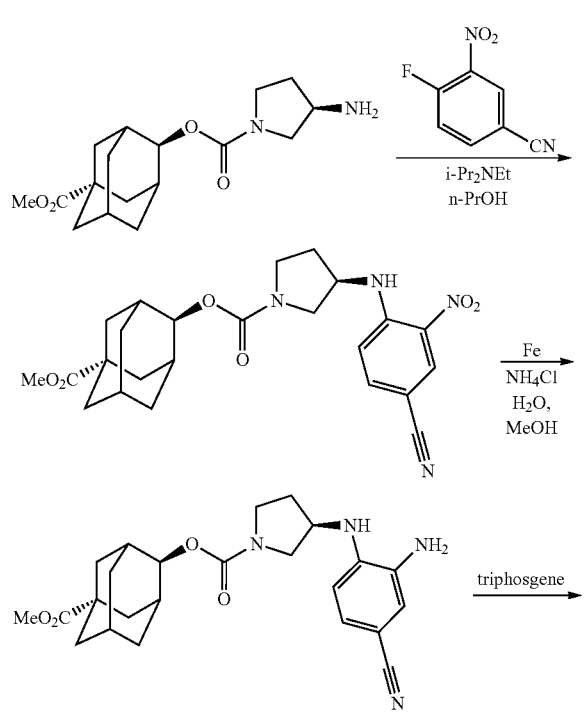

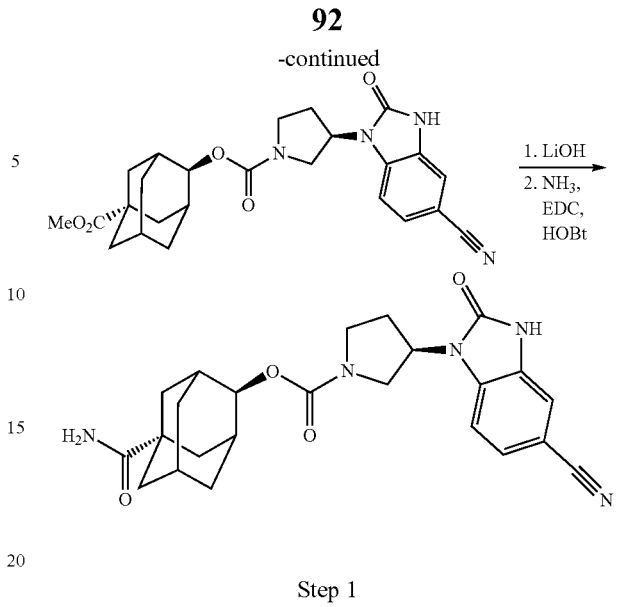

Step 1

A mixture of (R)-1-(methoxycarbonyl)adamantan-4-yl 3-aminopyrrolidine-1-carboxylate HCl salt (166 mg, 0.46 mmol), prepared as described in WO 2009/131669, 4-fluoro-3-nitrobenzonitrile (115 mg, 0.69 mmol), i-Pr$_2$NEt (0.25 mL, 1.4 mmol) and n-PrOH (3 mL) was heated at 120° C. for 1 h in the microwave. The mixture was diluted with EtOAc (100 mL), washed with water (10 mL), 2% aq HCl (10 mL) and brine (10 mL), and dried over Na$_2$SO$_4$. Removal of the solvent left an orange oil (293 mg) which was purified by prep HPLC to afford (R)-1-(methoxycarbonyl)adamantan-4-yl 3-((4-cyano-2-nitrophenyl)amino)pyrrolidine-1-carboxylate (80 mg, 37%) as a yellow oil. LC-MS Method 1 $t_R$=1.93 min, m/z=469.

Step 2

A stirred mixture of (R)-1-(methoxycarbonyl)adamantan-4-yl 3-((4-cyano-2-nitrophenyl)amino)pyrrolidine-1-carboxylate (80 mg, 0.17 mmol), iron powder (143 mg, 2.56 mmol), NH$_4$Cl (91 mg, 1.71 mmol), H$_2$O (5 mL) and MeOH (5 mL) was heated at reflux for 4 h. The mixture was filtered through Celite, washing with EtOAc and MeOH. The filtrate was concentrated. The aqueous residue was basified with K$_2$CO$_3$ and extracted with CH$_2$Cl$_2$ (100 mL). The organic layer was washed with brine (10 mL), dried over Na$_2$SO$_4$ and concentrated to afford crude (R)-1-(methoxycarbonyl)adamantan-4-yl 3-((2-amino-4-cyanophenyl)amino)pyrrolidine-1-carboxylate (75 mg, quant) which was used in the next step without purification. LC-MS Method 1 $t_R$=1.73 min, m/z=439.

Step 3

To a stirred, ice-cold solution of (R)-1-(methoxycarbonyl)adamantan-4-yl 3-((2-amino-4-cyanophenyl)amino)pyrrolidine-1-carboxylate (75 mg, 0.17 mmol) and i-Pr2NEt (0.095 mL, 0.53 mmol) in CH$_2$Cl$_2$ (5 mL) was added triphosgene (17.5 mg, 0.06 mmol). The mixture was allowed to warm slowly to rt, stirred overnight, diluted with EtOAc (90 mL), washed with 5% aq HCl (15 mL), satd aq NaHCO$_3$ (15 mL) and brine (15 mL), and dried over Na$_2$SO$_4$. Removal of the solvent afforded (R)-1-(methoxycarbonyl)adamantan-4-yl 3-(5-cyano-2-oxo-2,3-dihydro-1H-benzo[d]imidazol-1-yl)pyrrolidine-1-carboxylate (78 mg, 94%). LC-MS Method 1 $t_R$=1.65 min, m/z=465.

Steps 4 and 5

Procedures analogous to those described in Example 19 Steps 2 and 3 were employed to afford the title compound. LC-MS Method 1 $t_R$=1.23 min, m/z=450; $^1$H NMR (CD$_3$OD) 1.50-1.65 (m, 2H), 1.85-2.20 (m, 11H), 2.26-2.38 (m, 1H), 2.57-2.72 (m, 1H), 3.50-4.05 (m, 4H), 4.84 (s, 1H), 5.07-5.18 (m, 1H), 7.32-7.48 (m, 3H).

EXAMPLE 67

(S)-trans-1-carbamoyl-4-adamantyl 3-(7-chloro-2-oxo-2,3-dihydro-1H-benzo[d]imidazol-1-yl)pyrrolidine-1-carboxylate

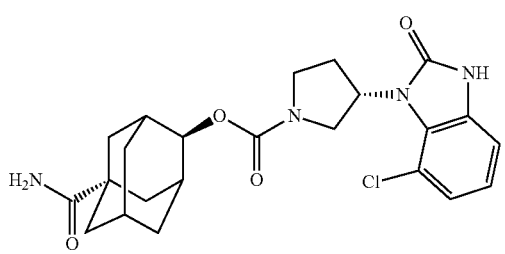 [SMILES: NC(=O)[C@]12CC3CC(C1)[C@@H](OC(=O)N1CC[C@H](n4c(=O)[nH]c5cccc(Cl)c54)C1)C(C3)C2]

The title compound was prepared following the procedure of Example 19 using (S)-7-chloro-1-(pyrrolidin-3-yl)-1H-benzo[d]imidazol-2(3H)-one in Step 1. LC-MS Method 1 $t_R$=1.47 min, m/z=459; $^1$H NMR (CD$_3$OD) 1.50-1.65 (m, 2H), 1.80-2.20 (m, 11H), 2.22-2.38 (m, 1H), 2.70-2.90 (m, 1H), 3.42-3.62 (m, 1H), 3.70-3.90 (m, 2H), 3.95-4.15 (m, 1H), 4.80 (s, 1H), 5.78-5.90 (m, 1H), 6.93-7.08 (m, 3H).

EXAMPLE 68

(R)-trans-1-carbamoyl-4-adamantyl 3-(7-chloro-2-oxo-2,3-dihydro-1H-benzo[d]imidazol-1-yl)pyrrolidine-1-carboxylate

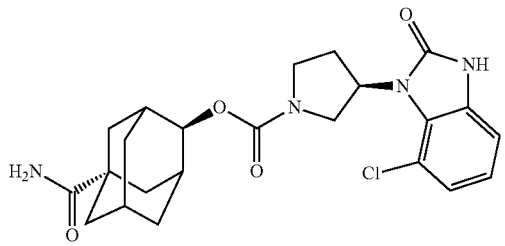 [SMILES: NC(=O)[C@]12CC3CC(C1)[C@@H](OC(=O)N1CC[C@@H](n4c(=O)[nH]c5cccc(Cl)c54)C1)C(C3)C2]

The title compound was prepared following the procedure of Example 19 using (R)-7-chloro-1-(pyrrolidin-3-yl)-1H-benzo[d]imidazol-2(3H)-one in Step 1. LC-MS Method 1 $t_R$=1.47 min, m/z=459; $^1$H NMR (CD$_3$OD) 1.49-1.62 (m, 2H), 1.85-2.15 (m, 11H), 2.23-2.37 (m, 1H), 2.71-2.88 (m, 1H), 3.45-4.15 (m, 4H), 4.81 (s, 1H), 5.78-5.89 (m, 1H), 6.98-7.09 (m, 3H).

EXAMPLE 69

(R)-trans-1-carbamoyl-4-adamantyl 3-(6-chloro-2-oxo-1H-imidazo[4,5-b]pyridin-3(2H)-yl)pyrrolidine-1-carboxylate

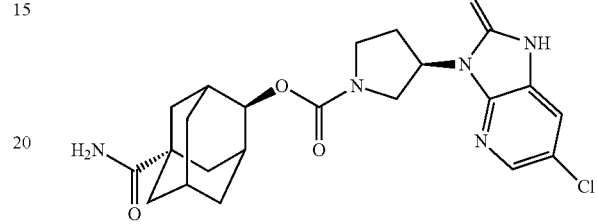

The title compound was prepared following the procedure of Example 19 using (R)-6-chloro-3-(pyrrolidin-3-yl)-1H-imidazo[4,5-b]pyridin-2(3H)-one in Step 1. LC-MS Method 1 $t_R$=1.35 min, m/z=460.

EXAMPLE 70

(S)-trans-1-carbamoyl-4-adamantyl 3-(5-cyano-3-methyl-2-oxo-2,3-dihydro-1H-benzo[d]imidazol-1-yl)pyrrolidine-1-carboxylate

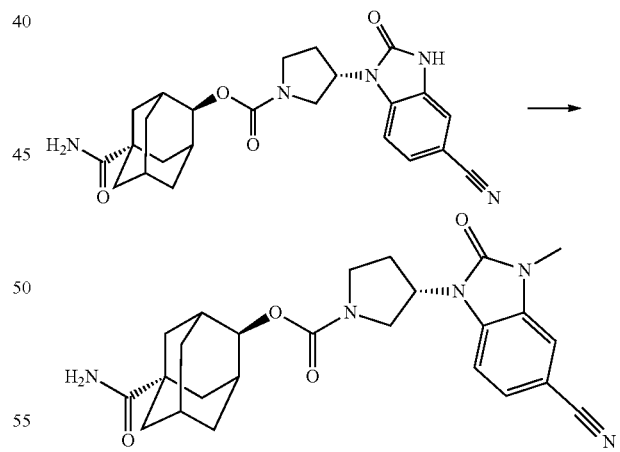

A stirred mixture of (S)-trans-1-carbamoyl-4-adamantyl 3-(5-cyano-2-oxo-2,3-dihydro-1H-benzo[d]imidazol-1-yl)pyrrolidine-1-carboxylate (13 mg, 0.029 mmol), Cs$_2$CO$_3$ (10.5 mg, 0.033 mmol), MeI (0.01 mL, 0.16 mmol) and MeCN (2 mL) was heated at reflux for 2 h. The reaction mixture was purified by prep HPLC to afford the title compound (8.1 mg, 60%) as a white solid. LC-MS Method 2 $t_R$=5.7 min, m/z=464; $^1$H NMR (CD$_3$OD) 1.50-1.65 (m, 2H), 1.85-2.20 (m, 11H), 2.28-2.38 (m, 1H), 2.55-2.68 (m, 1H), 3.42 (s, 3H), 3.45-4.05 (m, 4H), 4.84 (s, 1H), 5.10-5.22 (m, 1H), 7.38-7.41 (d, 1H), 7.48-7.53 (d, 1H), 7.58 (s, 1H).

EXAMPLE 71

(S)-trans-1-carbamoyl-4-adamantyl 3-(7-chloro-3-methyl-2-oxo-2,3-dihydro-1H-benzo[d]imidazol-1-yl)pyrrolidine-1-carboxylate

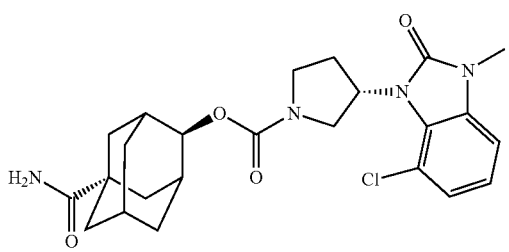 [SMILES: Cn1c(=O)n([C@H]2CCN(C(=O)O[C@H]3C4CC5CC3C[C@](C(N)=O)(C5)C4)C2)c2c(Cl)cccc21]

The title compound was prepared following the procedure of Example 70 using (S)-trans-1-carbamoyl-4-adamantyl 3-(7-chloro-2-oxo-2,3-dihydro-1H-benzo[d]imidazol-1-yl)pyrrolidine-1-carboxylate. LC-MS Method 2 $t_R$=7.2 min, m/z=473; $^1$H NMR (CDCl$_3$) 1.45-1.60 (m, 2H), 1.80-2.25 (m, 12H), 2.85-3.00 (m, 1H), 3.38 (s, 3H), 3.43-3.62 (m, 1H), 3.78-3.90 (m, 2H), 3.95-4.15 (m, 1H), 4.87 (s, 1H), 5.75-5.90 (m, 1H), 6.08 (br s, 1H), 6.87-6.92 (m, 1H), 7.02-7.12 (m, 2H), 7.41 (br s, 1H).

EXAMPLE 72

(S)-trans-1-carbamoyl-4-adamantyl 3-(5-fluoro-3-(2-methoxy-2-oxoethyl)-2-oxo-2,3-dihydro-1H-benzo[d]imidazol-1-yl)pyrrolidine-1-carboxylate

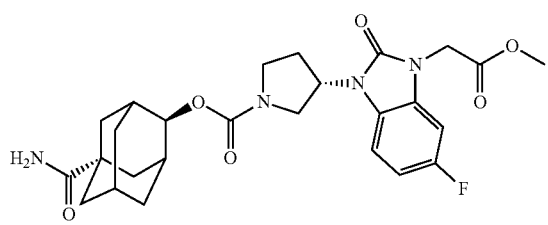 [SMILES: COC(=O)Cn1c(=O)n([C@H]2CCN(C(=O)O[C@H]3C4CC5CC3C[C@](C(N)=O)(C5)C4)C2)c2ccc(F)cc21]

The title compound was prepared following the procedure of Example 70 using (S)-trans-1-carbamoyl-4-adamantyl 3-(5-fluoro-2-oxo-2,3-dihydro-1H-benzo[d]imidazol-1-yl)pyrrolidine-1-carboxylate and methyl bromoacetate. LC-MS Method 1 $t_R$=1.45 min, m/z=515; $^1$H NMR (CDCl$_3$) 1.40-1.55 (m, 2H), 1.80-2.28 (m, 13H), 2.45-2.62 (m, 1H), 3.40-3.52 (m, 1H), 3.72 (s, 3H), 3.73-3.82 (m, 3H), 4.55 (s, 2H), 4.82 (s, 1H), 4.99-5.13 (m, 1H), 5.58-5.68 (m, 2H), 6.60-6.66 (m, 1H), 6.72-6.82 (m, 1H), 6.87-6.97 (m, 1H).

EXAMPLE 73

(S)-trans-1-carbamoyl-4-adamantyl 3-(5-fluoro-3-(2-hydroxyethyl)-2-oxo-2,3-dihydro-1H-benzo[d]imidazol-1-yl)pyrrolidine-1-carboxylate

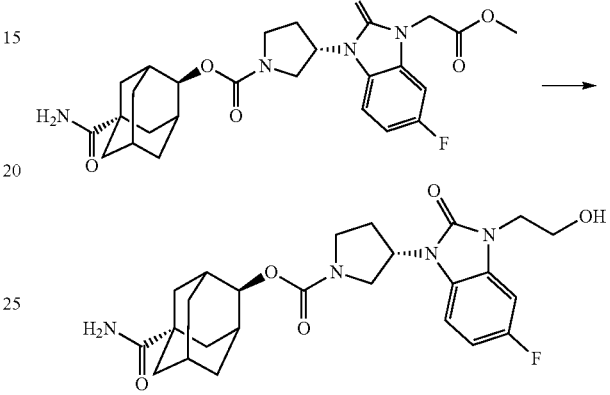

A stirred solution of (S)-trans-1-carbamoyl-4-adamantyl 3-(5-fluoro-3-(2-methoxy-2-oxoethyl)-2-oxo-2,3-dihydro-1H-benzo[d]imidazol-1-yl)pyrrolidine-1-carboxylate (13 mg, 0.025 mmol) in dry THF (1 mL) was cooled in an ice bath and 2 M LiBH$_4$ in THF (1 mL, 2 mmol) was added. The mixture was stirred for 3 h and water (0.5 mL) was added. The mixture was concentrated, diluted with 5% aq HCl (0.5 mL) and MeOH (2 mL), and filtered. The filtrate was purified by prep HPLC to afford the title compound (6 mg, 48%) as a solid. LC-MS Method 1 $t_R$=1.26 min, m/z=487; $^1$H NMR (CDCl$_3$) 1.44-1.60 (m, 2H), 1.70-2.35 (13H), 2.58 (m, 1H), 3.48-3.59 (m, 1H), 3.77-3.90 (m, 3H), 3.90-4.05 (m, 4H), 4.89 (s, 1H), 5.05-5.20 (m, 1H), 5.70 (s, 1H), 5.80 (s, 1H), 6.78-6.83 (m, 1H), 6.83-6.91 (m, 1H), 6.92-6.98 (m, 1H).

EXAMPLE 74

(S)-1-carbamoyl-4-adamantyl 3-(5-fluoro-2-methyl-1H-benzo[d]imidazol-1-yl)pyrrolidine-1-carboxylate

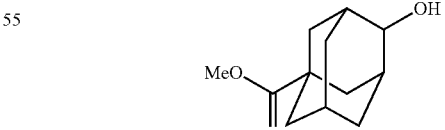

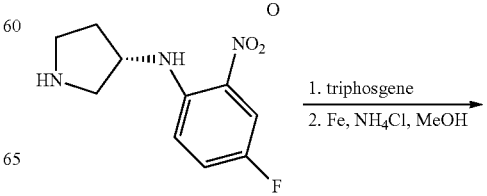

-continued

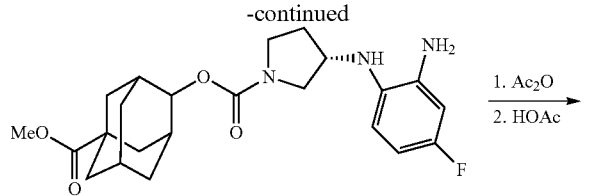

1. Ac₂O
2. HOAc

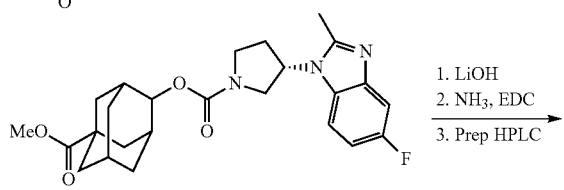

1. LiOH
2. NH₃, EDC
3. Prep HPLC

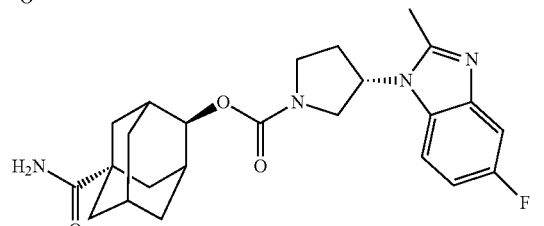

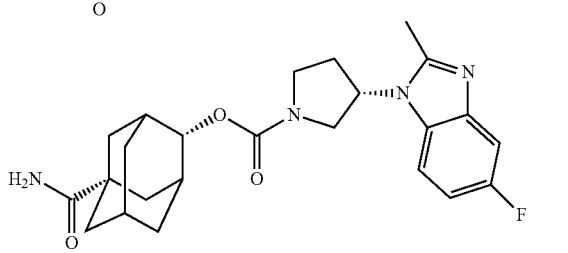

Step 1

A procedure analogous to that of Example 19 Step 1 was employed using (S)—N-(4-fluoro-2-nitrophenyl)pyrrolidin-3-amine to afford (3S)-1-(methoxycarbonyl)adamantan-4-yl 3-((4-fluoro-2-nitrophenyl)amino)pyrrolidine-1-carboxylate. LC-MS Method 1 $t_R$=2.07 min, m/z=462.

Step 2

A procedure analogous to that of Example 66 Step 2 was employed to afford (3S)-1-(methoxycarbonyl)adamantan-4-yl 3-((2-amino-4-fluorophenyl)amino)pyrrolidine-1-carboxylate. LC-MS Method 1 $t_R$=1.77 min, m/z=432.

Step 3

A procedure analogous to that of Preparation 11 Step 1 was employed. LC-MS Method 1 $t_R$=1.72 min, m/z=474.

Step 4

A procedure analogous to that of Preparation 11 Step 2 was employed to afford (3S)-1-(methoxycarbonyl)adamantan-4-yl 3-(5-fluoro-2-methyl-1H-benzo[d]imidazol-1-Apyrrolidine-1-carboxylate. LC-MS Method 1 $t_R$=1.37 min, m/z=456.

Step 5

A procedure analogous to that of Example 19 Step 1 was employed to afford 4-(((S)-3-(5-fluoro-2-methyl-1H-benzo[d]imidazol-1-yl)pyrrolidine-1-carbonyl)oxy)adamantane-1-carboxylic acid. LC-MS Method 1 $t_R$=1.17 min, m/z=442.

Step 6

A procedure analogous to that of Example 19 Step 2 was employed to afford the title compound. Prep HPLC afforded two isomers.

Isomer 1: (S)-trans-1-carbamoyl-4-adamantyl 3-(5-fluoro-2-methyl-1H-benzo[d]imidazol-1-yl)pyrrolidine-1-carboxylate. LC-MS Method 2 $t_R$=3.83 min, m/z=441; ¹H NMR (CD₃OD) 1.50-1.70 (m, 2H), 1.80-2.25 (m, 11H), 2.55-2.65 (m, 1H), 2.65-2.80 (m, 1H), 2.92 (s, 3H), 3.55-3.75 (m, 1H), 3.90-4.20 (m, 3H), 4.84 (s, 1H), 5.48-5.58 (m, 1H), 7.37-7.42 (m, 1H), 7.56-7.60 (m, 1H), 7.84-7.92 (m, 1H).

Isomer 2: (S)-cis-1-carbamoyl-4-adamantyl 3-(5-fluoro-2-methyl-1H-benzo[d]imidazol-1-yl)pyrrolidine-1-carboxylate. LC-MS Method 2 $t_R$=3.93 min, m/z=441; ¹H NMR (CD₃OD) 1.60-2.25 (m, 13H), 2.55-2.65 (m, 1H), 2.65-2.80 (m, 1H), 2.94 (s, 3H), 3.55-3.75 (m, 1H), 3.85-4.15 (m, 3H), 4.83 (s, 1H), 5.48-5.57 (m, 1H), 7.35-7.42 (m, 1H), 7.56-7.60 (m, 1H), 7.84-7.92 (m, 1H).

EXAMPLE 75

(S)-1-carbamoyl-4-adamantyl 3-(5-cyano-2-methyl-1H-benzo[d]imidazol-1-yl)pyrrolidine-1-carboxylate

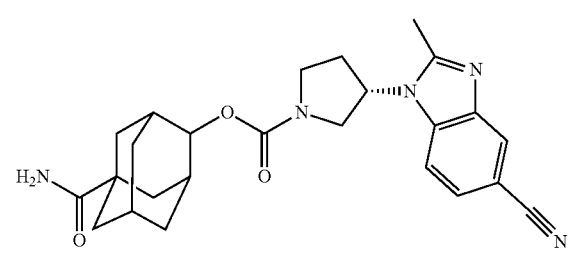 [SMILES: Cc1nc2cc(C#N)ccc2n1[C@H]1CCN(C(=O)OC2C3CC4CC2CC(C(N)=O)(C4)C3)C1]

The title compound was prepared following the procedure of Example 19 using (S)-2-methyl-1-(pyrrolidin-3-yl)-1H-benzo[d]imidazole-5-carbonitrile in Step 1. The product was isolated as a mixture of cis and trans isomers. LC-MS Method 2 $t_R$=4.37 m/z=448; $t_R$=4.54 min, m/z=448.

EXAMPLE 76

(S)-1-carbamoyl-4-adamantyl 3-(7-chloro-2-methyl-1H-benzo[d]imidazol-1-yl)pyrrolidine-1-carboxylate

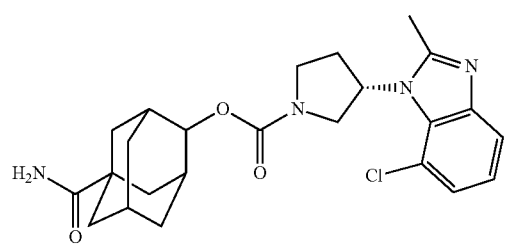 [SMILES: Cc1nc2cccc(Cl)c2n1[C@H]1CCN(C(=O)OC2C3CC4CC2CC(C(N)=O)(C4)C3)C1]

The title compound was prepared following the procedure of Example 19 using (S)-7-chloro-2-methyl-1-(pyrrolidin-3-yl)-1H-benzo[d]imidazole in Step 1. LC-MS Method 1

$t_R$=1.2 min, m/z=457; $^1$H NMR (CD$_3$OD) 1.53 1.67 (m, 2H), 1.85-2.20 (m, 11H), 1.81-1.87 (m, 1H), 1.87-1.93 (m, 1H), 2.96 (s, 3H), 3.55-4.25 (m, 4H), 4.85 (s, 1H), 5.85-6.00 (m, 1H), 7.54-7.7.60 (m, 1H), 7.66-7.70 (d, 1H), 7.73-7.77 (d, 1H).

EXAMPLE 77

(R)-3-(5-Cyano-2-oxo-2H-pyridin-1-yl)-pyrrolidine-1-carboxylic acid 5-hydroxy-adamantan-2-yl ester (ca. 1:1 mixture of cis- and trans-isomer)

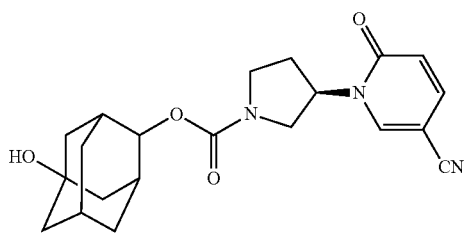 [SMILES: N#Cc1ccc(=O)n([C@@H]2CCN(C(=O)OC3C4CC5CC3CC(O)(C5)C4)C2)c1]

Diethyl azodicarboxylate (40% in toluene, 1.7 mL) is added to a mixture of (S)-3-hydroxy-pyrrolidine-1-carboxylic acid 5-hydroxy-adamantan-2-yl ester (ca. 1:1 mixture of cis- and trans-isomer, 0.50 g), 6-oxo-1,6-dihydro-pyridine-3-carbonitrile (0.22 g), triphenylphosphine (0.97 g), and tetrahydrofuran (10 ml) at room temperature. The resulting mixture is stirred for 2 h and then concentrated. The residue is chromatographed on silica gel (ethyl acetate/methanol 95:5→80:20) and then on reversed phase (HPLC, acetonitrile/water containing 1.36% trifluoroacetic acid) to give the title compound as a mixture of two diastereomers (cis/trans ca. 1:1). Yield: 8 mg (1% of theory); LC (method 1): $t_R$=1.03/1.06 min; Mass spectrum (ESI$^+$): m/z=384 [M+H]$^+$.

EXAMPLE 78

(R)-3-(4-Cyano-2-oxo-2H-pyridin-1-yl)-pyrrolidine-1-carboxylic acid 5-hydroxy-adamantan-2-yl ester

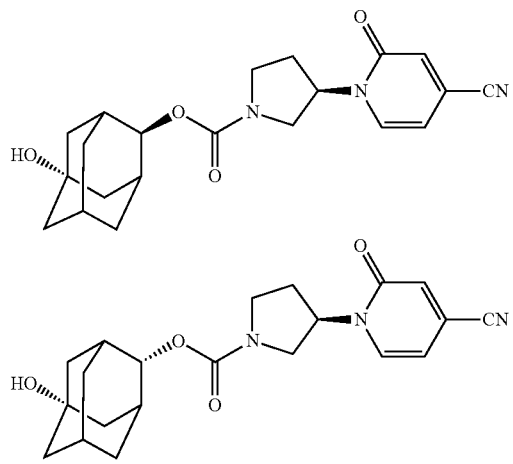

The title compounds were prepared from (S)-3-hydroxy-pyrrolidine-1-carboxylic acid 5-hydroxy-adamantan-2-yl ester (ca. 1:1 mixture of cis- and trans-isomer) and 2-oxo-1,6-dihydro-pyridine-4-carbonitrile following a procedure analogous to that described in Example 77. The isomers were separated by HPLC on reversed phase (acetonitrile/water containing 1.36% trifluoroacetic acid).

Isomer 1: cis-(R)-3-(4-Cyano-2-oxo-2H-pyridin-1-yl)-pyrrolidine-1-carboxylic acid 5-hydroxy-adamantan-2-yl ester (ca. 3:1 mixture with Isomer 2): Yield: 2% of theory; LC-MS Method 4 $t_R$=1.03 min; Mass spectrum (ESI$^+$): m/z=384 [M+H]$^+$.

Isomer 2: trans-(R)-3-(4-Cyano-2-oxo-2H-pyridin-1-yl)-pyrrolidine-1-carboxylic acid 5-hydroxy-adamantan-2-yl ester (3): Yield: 2% of theory; LC-MS Method 4 $t_R$=1.06 min; Mass spectrum (ESI$^+$): m/z=384 [M+H]$^+$.

EXAMPLE 79

(R)-3-(4-Cyano-hyridin-2-yloxy)-pyrrolidine-1-carboxylic acid 5-hydroxy-adamantan-2-yl ester

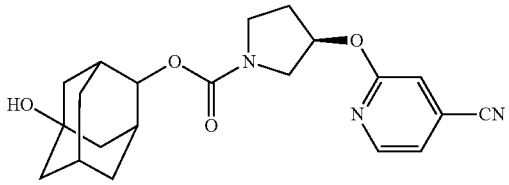 [SMILES: N#Cc1ccnc(O[C@@H]2CCN(C(=O)OC3C4CC5CC3CC(O)(C5)C4)C2)c1]

The title compounds was isolated as a byproduct from the procedure described in Example 78. Yield: 6% of theory; LC-MS Method 4 $t_R$=1.29 min; Mass spectrum (ESI$^+$): m/z=384 [M+H]$^+$.

BIOLOGICAL TEST EXAMPLE 1

The inhibition of a microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxyseroid Dehydrogenase Type 1 in Scintillation Proximity Assay Format. Assay Drug Dev Technol 3 (2005) 377-384). All reactions were carried out at rt in 96 well clear flexible PET Microbeta plates (PerkinElmer). The assay begins by dispensing 49 μl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) and mixing in 1 μL of the test compounds in DMSO previously diluted in half-log increments (8 points) starting at 0.1 mM. After a 10 minute pre-incubation, 50 μL of enzyme solution containing microsomes isolated from CHO cells overexpressing human 11-HSD1 (10-20 μg/ml of total protein) was added, and the plates were incubated for 90 minutes at rt. The reaction was stopped by adding 50 μl of the SPA beads suspension containing 10 μM 18ε-glycyrrhetinic acid, 5 mg/ml protein A coated YSi SPA beads (GE Healthcare) and 3.3 μg/ml of anti-cortisol antibody (East Coast Biologics) in Superblock buffer (Bio-Rad). The plates were shaken for 120 minutes at rt, and the SPA signal corresponding to [$^3$H]cortisol was measured on a Microbeta plate reader.

BIOLOGICAL TEST EXAMPLE 2

The inhibition of 11β-HSD1 by compounds of this invention was measured in whole cells as follows. Cells for the assay were obtained from two sources: fully differentiated human omental adipocytes from Zen-Bio, Inc.; and human omental pre-adipocytes from Lonza Group Ltd. Pre-differentiated omental adipocytes from Zen-Bio Inc. were purchased in 96-well plates and were used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% $CO_2$.

Pre-adipocytes were purchased from Lonza Group Ltd. and placed in culture in Preadipocyte Growth Medium-2 supplemented with fetal bovine serum, penicillin, and streptomycin (supplied by Lonza) at 37° C., 5% $CO_2$. Pre-adipocytes were differentiated by the addition of insulin, dexamethasone, indomethacin and isobutyl-methylxanthine (supplied by Lonza) to the Preadipocyte Growth Medium-2. Cells were exposed to the differentiating factors for 7 days, at which point the cells were differentiated and ready for the assay. One day before running the assay, the differentiated omental adipocytes were transferred into serum- and phenol-red-free medium for overnight incubation. The assay was performed in a total volume of 200 µL. The cells were pre-incubated with serum-free, phenol-red-free medium containing 0.1% (v/v) of DMSO and various concentrations of the test compounds at least 1 h before [$^3$H] cortisone in ethanol (50 Ci/mmol, ARC, Inc.) was added to achieve a final concentration of cortisone of 100 nM. The cells were incubated for 3-4 hrs at 37° C., 5% $CO_2$. Negative controls were incubated without radioactive substrate and received the same amount of [$^3$H] cortisone at the end of the incubation. Formation of [$^3$H] cortisol was monitored by analyzing 25 µL of each supernatant in a scintillation proximity assay (SPA). (Solly, K.; Mundt, S. S.; Zokian, H. J.; Ding, G. J.; Hermanowski-Vosatka, A.; Strulovici, B.; Zheng, W. Assay Drug Dev. Technol. 2005, 3, 377-384). Many compounds of the invention showed significant activity in this assay.

BIOLOGICAL TEST EXAMPLE 3

The inhibition of purified 11β-HSD1 by compounds of Formula I is measured using a Scintillation Proximity Assay. All reactions are carried out at room temperature in 96 well flexible Microbeta reaction plates. First, 1 µL of a 0.1 mM solution of a compound of Formula I is mixed in DMSO diluted in half-log increments (8 points) starting at 1 µM final concentration. To this dot is added 50 µL of substrate solution (50 mM HEPES, pH 7.4, 100 mM KCl, 5 mM NaCl, 2 mM $MgCl_2$ containing 20 µM $^3$H cortisone, 1 mM NADPH). After a 10 minute incubation, 50 µL of enzyme solution containing 20 nM recombinant 11β-HSD1 (expressed in *E. coli*, and affinity purified) is added. The reaction is then incubated for 90 minutes, and stopped by adding 50 µl of SPA bead mix (18-β-glycyrrhetinic acid, 10 µM final, 5 mg/ml protein A coated YSi SPA beads, and 1 ug/ml α-cortisol antibody (East Coast Biologics)). The plate is shaken for 120 minutes, and the radioactivity corresponding to $^3$H cortisol is measured on a Wallac Microbeta.

| Compound | $IC_{50}$ Range[a] | Average % inhibition at 100 nM | $IC_{50}$ (nM) |
|---|---|---|---|
| EXAMPLE 1 | ++ | 95.53 | 1.54 |
| EXAMPLE 2 | ++ | 96.20 | 0.68 |
| EXAMPLE 3 | ++ | 92.10 | 6.39 |
| EXAMPLE 4 | ++ | 90.28 | 2.63 |
| EXAMPLE 5 | ++ | 94.90 | 0.99 |
| EXAMPLE 6 | ++ | 96.93 | 0.54 |

| Compound | Biological Test Example 1 | | | | Biological Test Example 3 |
|---|---|---|---|---|---|
| | $IC_{50}$ Range[a] | Average % inhibition at 100 nM | Average % inhibition at 111 nM | $IC_{50}$ (nM) | $IC_{50}$ Range[a] |
| EXAMPLE 7 | | | | | ++ |
| EXAMPLE 8 | | | | | ++ |
| EXAMPLE 9 | | | | | ++ |
| EXAMPLE 10 | | | | | ++ |
| EXAMPLE 11 | ++ | | 86.3 | 6.65 | |
| EXAMPLE 12 | | | | | + |
| EXAMPLE 13 | | | | | ++ |
| EXAMPLE 14 | ++ | | 87.6 | 7.15 | |
| EXAMPLE 15 | ++ | | 80.6 | 5.39 | |
| EXAMPLE 16 | ++ | | 72.3 | 43.78 | |
| EXAMPLE 17 | ++ | 94.2 | | 1.96 | |
| EXAMPLE 18 | ++ | | 82.2 | 27.79 | |
| EXAMPLE 19 | ++ | 93.2 | | 6.74 | |
| EXAMPLE 20 | # | 28.6 | | 100.00 | |
| EXAMPLE 21 | ++ | 81.4 | | 20.78 | |
| EXAMPLE 22 | # | 3.7 | | 100.00 | |
| EXAMPLE 23 | ++ | 79.3 | | 17.62 | |
| EXAMPLE 24 Isomer 1 | ++ | 98.6 | | 2.29 | |
| EXAMPLE 24 Isomer 2 | # | 34.7 | | 100.00 | |
| EXAMPLE 25 | ++ | 69.9 | | 39.46 | |
| EXAMPLE 26 | ++ | 94.5 | | 1.12 | |
| EXAMPLE 26 Isomer 1a | ++ | 102.6 | | 1.15 | |
| EXAMPLE Isomer 1b | ++ | 84.2 | | 1.91 | |
| EXAMPLE 26 Isomer 2 | # | 26.3 | | >100 | |
| EXAMPLE 27 | | | | | ++ |
| EXAMPLE 28 | ++ | 84.8 | | 3.69 | |
| EXAMPLE 29 | ++ | 99.2 | | 1.00 | |
| EXAMPLE 30 | ++ | [80.1][b] | | 13.22 | |
| EXAMPLE 30 | ++ | 87.4 | | 4.44 | |
| EXAMPLE 31 | ++ | 44.1 | | 91.7 | |
| EXAMPLE 32 | ++ | 94.7 | | 1.08 | |

| Compound | $IC_{50}$ Range[a] | Average % inhibition at 100 nM | $IC_{50}$ (nM) |
|---|---|---|---|
| EXAMPLE 33 | ++ | 84.0 | 7.46 |
| EXAMPLE 34 | ++ | 96.8 | 0.52 |
| EXAMPLE 35 Isomer 1 | ++ | 91.6 | 1.61 |
| EXAMPLE 35 Isomer 2 | # | 8.1 | >100 |
| EXAMPLE 36 Isomer 1 | ++ | 59.1 | 83.73 |
| EXAMPLE 36 Isomer 2 | # | 1.5 | >100 |
| EXAMPLE 37 Isomer 1 | ++ | 76.6 | 16.26 |
| EXAMPLE 37 Isomer 2 | # | 13.3 | >100 |
| EXAMPLE 38 Isomer 1 | ++ | 93.1 | 3.34 |
| EXAMPLE 38 Isomer 2 | # | 10.7 | >100 |
| EXAMPLE 39 Isomer 1 | ++ | 59.7 | 2.99 |

-continued

| Compound | Biological Test Example 1 | | |
|---|---|---|---|
| | IC$_{50}$ Range$^a$ | Average % inhibition at 100 nM | IC$_{50}$ (nM) |
| EXAMPLE 39 Isomer 2 | # | 1.8 | >100 |
| EXAMPLE 40 Isomer 1 | ++ | 90.8 | 6.88 |
| EXAMPLE 40 Isomer 2 | # | 5.2 | >100 |
| EXAMPLE 41 Isomer 1 | ++ | 92.3 | 2.99 |
| EXAMPLE 41 Isomer 2 | ++ | 69.0 | 48.80 |
| EXAMPLE 42 Isomer 1 | ++ | 91.8 | 2.08 |
| EXAMPLE 42 Isomer 2 | # | 21.8 | >100 |
| EXAMPLE 43 Isomer 1 | ++ | 86.5 | 5.72 |
| EXAMPLE 43 Isomer 2 | # | −1.8 | >100 |
| EXAMPLE 44 Isomer 1 | ++ | 95.2 | 3.11 |
| EXAMPLE 44 Isomer 2 | # | 2.4 | >100 |
| EXAMPLE 45 | ++ | 87.5 | 13.49 |
| EXAMPLE 46 Isomer 1 | # | 22.4 | >100 |
| EXAMPLE 46 Isomer 2 | # | 3.8 | >100 |
| EXAMPLE 47 Isomer 1 | # | 6.1 | >100 |
| EXAMPLE 47 Isomer 2 | ++ | 55.6 | 91.6 |
| EXAMPLE 48 Isomer 1 | ++ | 94.5 | 2.70 |
| EXAMPLE 48 Isomer 2 | # | 16.1 | >100 |
| EXAMPLE 49 | ++ | 91.6 | 2.07 |
| EXAMPLE 50 | ++ | 98.2 | 0.91 |
| EXAMPLE 51 | ++ | 96.8 | 0.70 |
| EXAMPLE 52 | ++ | 95.1 | 1.19 |
| EXAMPLE 53 | ++ | 95.8 | 0.47 |
| EXAMPLE 54 | ++ | 95.4 | 2.67 |
| EXAMPLE 55 | ++ | 93.1 | 2.07 |
| EXAMPLE 56 | ++ | 96.7 | 1.95 |
| EXAMPLE 57 Isomer 1 | ++ | 65.0 | 50.5 |
| EXAMPLE 57 Isomer 2 | # | 18.1 | >100 |
| EXAMPLE 58 Isomer 1 | ++ | 69.4 | 33.3 |
| EXAMPLE 58 Isomer 2 | # | 3.8 | >100 |
| EXAMPLE 59 | ++ | 96.7 | 1.92 |
| EXAMPLE 60 | ++ | 93.9 | 0.76 |
| EXAMPLE 61 | ++ | 89.9 | 4.17 |
| EXAMPLE 62 | ++ | 92.7 | 3.07 |
| EXAMPLE 63 | ++ | 91.2 | 1.01 |
| EXAMPLE 64 | ++ | 94.2 | 1.71 |
| EXAMPLE 65 | ++ | 69.0 | 33.10 |
| EXAMPLE 66 | ++ | 93.9 | 2.48 |
| EXAMPLE 67 | ++ | 97.7 | 0.68 |
| EXAMPLE 68 | ++ | 96.9 | 0.46 |
| EXAMPLE 69 | ++ | 97.0 | 1.04 |
| EXAMPLE 70 | ++ | 91.3 | 3.14 |
| EXAMPLE 71 | ++ | 96.6 | 0.67 |
| EXAMPLE 72 | ++ | 84.9 | 7.11 |
| EXAMPLE 73 | ++ | 93.0 | 4.52 |
| EXAMPLE 74 Isomer 1 | ++ | 91.9 | 2.22 |
| EXAMPLE 74 Isomer 2 | ++ | 83.2 | 16.61 |
| EXAMPLE 75 | ++ | 39.1 | 5.03 |
| EXAMPLE 76 | ++ | 93.6 | 1.11 |

$^a$ ++ means IC$_{50}$ = <100 nM, + means IC$_{50}$ = 100-1000 nM, # means IC$_{50}$ >100 nM, − means IC$_{50}$ >1000 nM;
$^b$ Dose = 63 nM.

BIOLOGICAL TEST EXAMPLE 4

In vitro inhibition of 11β-HSD1 by test compounds is determined with HTRF (Homogeneous Time-Resolved Fluorescence) technology (cisbio international, France) detecting cortisol generated from cortisterone by human liver microsomes. Briefly, compounds are incubated for 1 hour at 37° C. in Tris buffer (20 mM tris, 5 mM EDTA, pH 6.0) containing NADPH (200 µM) and cortisone (80 nM). Cortisol generated in the reaction is then detected with a competitive immunoassay, involving two HTRF conjugates: cortisol linked to XL665 and anti-cortisol antibody labeled with Europium cryptate. The incubation period for detection reaction is typically 2 hours. The amount of cortisol is determined by reading the time-resolved fluorescence of the wells (Ex 320/75 nm; Em 615/8.5 nm and 665/7.5 nm). The ratio of the two emission signals is then calculated (Em665*10000/Em615). Each assay contains incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contains a calibration curve with cortisol to transform the fluorescent data into cortisol concentrations. Percent inhibition (% CTL) of each compound is determined relative to the carbenoxolone signal and IC$_{50}$ curves are generated.

| Compound | Biological Test Example 4 IC$_{50}$ [nM] |
|---|---|
| Example 77 | >10000 |
| Example 78 Isomer 1 | >10000 |
| Example 78 Isomer 2 | 1168 |
| Example 79 | >10000 |

The compounds of the invention are useful for ameliorating or treating disorders or diseases in which decreasing the level of cortisol is effective in treating a disease state. Thus, the compounds of the invention can be used in the treatment or prevention of diabetes mellitus, obesity, symptoms of metabolic syndrome, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypretriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X.

The disclosed compounds can be used alone (i.e. as a monotherapy) or in combination with another therapeutic agent effective for treating any of the above indications. Alternatively, a pharmaceutical composition of the invention may comprise a compounds of the invention or a pharmaceutical salt thereof as the only pharmaceutically active agent in the pharmaceutical composition. The disclosed 11β-HSD1 inhibitors can be used alone or in a combination therapy with one or more additional agents for the treatment of diabetes, dyslipidemia, cardiovascular disease, hypertension, obesity, cancer or glaucoma.

A pharmaceutical composition of the invention may, alternatively or in addition to a compounds of the invention comprise a pharmaceutically acceptable salt of a compounds of the invention or a prodrug or pharmaceutically active metabolite of such a compound or salt and one or more pharmaceutically acceptable carriers therefore. Alternatively, a pharmaceutical composition of the invention may comprise a compounds of the invention or a pharmaceutical salt thereof as the only pharmaceutically active agent in the pharmaceutical composition.

The invention includes a therapeutic method for treating or ameliorating an 11β-HSD1 mediated disorder in a subject in need thereof comprising administering to a subject in need thereof an effective amount of a compound of the invention, or an enantiomer, diastereomer, or pharmaceutically acceptable salt thereof of composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compounds of the invention or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin® (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza® (metformin HCl, Depomed); thiazolidinediones; amylin analogs, GLP-1 analogs; DPP-IV inhibitors, such as Januvia™ (sitagliptin, Merck); PTB-1B inhibitors; protein kinase inhibitors (including AMP-activated protein kinase inhibitors); glucagon antagonists, glycogen synthase kinase-3 beta inhibitors; glucose-6-phosphatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitor, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of the invention or composition thereof in a combination therapy with one or more other 11β-HSD1 inhibitors (whether such inhibitors are also compounds of the invention or are compounds of a different class/genus), or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

What is claimed is:

1. A compound of Formula I:

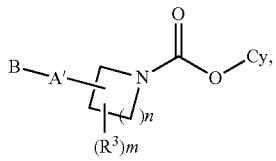

wherein

Cy is adamantyl, optionally substituted with 1-3 groups independently selected from halogen, cyano, hydroxy, hydroxy($C_1$-$C_3$)alkyl, $N(R^4)_2$, $CO_2R^4$, $CON(R^4)_2$, $CH_2CON(R^4)_2SO_2N(R^4)_2$, $SO_2R^4$, $NR^4COR^4$ and $OC(=O)N(R^4)_2$;

B is aryl, heterocyclyl or heteroaryl, each optionally substituted with 1-4 groups represented by $R^6$;

$R^3$ is ($C_1$-$C_8$)alkyl, ($C_2$-$C_8$)alkenyl, ($C_2$-$C_8$)alkynyl, cycloalkyl($C_0$-$C_3$)alkyl, heterocyclyl($C_0$-$C_3$)alkyl, aryl($C_0$-$C_3$)alkyl, or heteroaryl($C_0$-$C_3$)alkyl, each optionally substituted by 1-4 groups independently selected from halogen, nitro, cyano, ($C_1$-$C_3$)alkyl, halo($C_1$-$C_3$)alkyl, halo($C_1$-$C_3$)alkoxy, hydroxy($C_1$-$C_3$)alkyl, $OR^4$, $N(R^4)_2$, $(CH_2)_xC(=NOH)NH_2$, $(CH_2)_xNR^4CON(R^4)_2$, $(CH_2)_xCON(R^4)_2$, $(CH_2)_xSO_2N(R^4)_2$, $(CH_2)_xSO_2R^4$, $(CH_2)_xNR^4COR^4$, $(CH_2)_xNR^4SO_2R^4$, $(CH_2)_xOC(=O)N(R^4)_2$, $(CH_2)_xOR^4$, $(CH_2)_xO(CH_2)_xCO_2R^4$, optionally substituted aryl, optionally substituted heteroaryl, optionally substituted heterocyclyl and optionally substituted cycloalkyl, wherein aryl, heteroaryl, heterocyclyl and cycloalkyl are optionally substituted with one to three groups represented by $R^7$, wherein the ($C_2$-$C_8$)alkenyl, ($C_2$-$C_8$)alkynyl, ($C_3$-$C_8$)cycloalkyl, heterocyclyl, heteroaryl, cycloalkyl($C_0$-$C_3$)alkyl, heterocyclyl($C_0$-$C_3$)alkyl, alkyl portion of aryl($C_0$-$C_3$)alkyl and heteroaryl($C_0$-$C_3$)alkyl are further optionally substituted with oxo;

each $R^4$ is independently (a) hydrogen; or (b) ($C_1$-$C_{10}$)alkyl, or aryl($C_0$-$C_3$)alkyl, each optionally substituted with 1-4 groups selected from halogen, ($C_1$-$C_3$)alkoxy, ($C_1$-$C_3$)alkyl, halo($C_1$-$C_3$)alkyl, halo($C_1$-$C_3$)alkoxy, cyano and nitro;

each $R^6$ is independently selected from halogen, nitro, cyano, ($C_1$-$C_3$)alkyl, cyclo($C_3$-$C_6$)alkyl, halo($C_1$-$C_3$)alkyl, hydroxy($C_1$-$C_3$)alkyl, oxo, $OR^4$, halo($C_1$-$C_3$)alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, $(CH_2)_xOR^4$, $(CH_2)_xO(CH_2)_xCO_2R^4$, optionally substituted aryl, optionally substituted heteroaryl, optionally substituted heterocyclyl and optionally substituted cycloalkyl, wherein the aryl, heteroaryl, heterocyclyl and cycloalkyl are further optionally substituted with one to three groups represented by $R^7$;

$R^7$ is halogen, nitro, cyano, ($C_1$-$C_3$)alkyl, halo($C_1$-$C_3$)alkyl, cyclo($C_3$-$C_6$)alkyl, ($C_1$-$C_3$)alkoxy, halo($C_1$-$C_3$)alkoxy, $N(R^4)_2$, or $CON(R^4)_2$, provided that $R^7$ also includes oxo when the heteroaryl, heterocyclyl and cycloalkyl are substituted with $R^7$;

x is 0, 1, 2 or 3;

A' is a bond, $CH_2$, or -AO—, wherein O is connected to B;

A is a bond or $CH_2$;

m is 0; and n is 1 or 2;

or a pharmaceutically acceptable salt thereof.

2. The compound of claim 1, wherein the compound is of the following Formula:

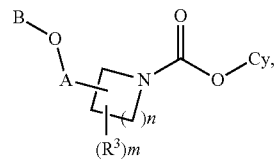

or a pharmaceutically acceptable salt thereof.

3. The compound of claim 2, wherein the compound is of the following Formula:

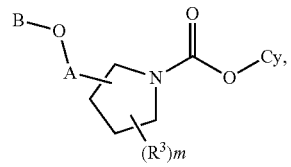

or a pharmaceutically acceptable salt thereof.

4. The compound of claim 3, wherein the compound is of the following Formula:

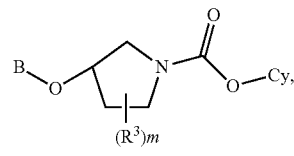

or a pharmaceutically acceptable salt thereof.

5. The compound of claim 4, wherein $R^3$ is ($C_1$-$C_8$)alkyl or aryl($C_0$-$C_3$)alkyl, each optionally substituted by 1-4 groups independently selected from halogen, cyano, ($C_1$-$C_3$)alkyl, halo($C_1$-$C_3$)alkyl, hydroxy($C_1$-$C_3$)alkyl, $OR^4$, $N(R^4)_2$, $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$, wherein the alkyl portion of aryl($C_0$-$C_3$)alkyl is further optionally substituted with oxo; and $R^4$ is independently hydrogen or ($C_1$-$C_3$) alkyl.

6. The compound of claim 2, wherein B is heteroaryl, optionally substituted with 1-4 groups represented by $R^6$; wherein each $R^6$ is independently selected from halogen, cyano, $(C_1-C_3)$alkyl, cyclo$(C_3-C_6)$alkyl, halo$(C_1-C_3)$alkyl, hydroxy$(C_1-C_3)$alkyl, oxo, $OR^4$, halo$(C_1-C_3)$alkoxy, $(CH_2)_xN(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xNR^4CON(R^4)_2$, and $(CH_2)_xOC(=O)N(R^4)_2$.

7. The compound of claim 6, wherein the compound is of the following Formula:

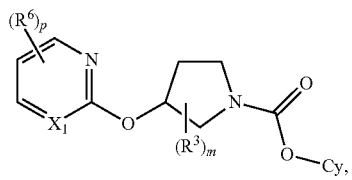

wherein:

$X_1$ is N or $CR^5$;

$R^5$ is hydrogen or $(C_1-C_6)$alkyl;

$R^6$ is halogen, cyano, $(C_1-C_3)$alkyl, cyclo$(C_3-C_6)$alkyl, halo$(C_1-C_3)$alkyl, hydroxy$(C_1-C_3)$alkyl, $OR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, $(CH_2)_xOR^4$, $(CH_2)_xO(CH_2)_xCO_2R^4$, optionally substituted aryl, optionally substituted heteroaryl, optionally substituted heterocyclyl or optionally substituted cycloalkyl, wherein the aryl, heteroaryl, heterocyclyl and cycloalkyl are further optionally substituted with one to three groups represented by $R^7$; and p is 0, 1, 2 or 3;

or a pharmaceutically acceptable salt thereof.

8. The compound of claim 1, wherein the compound is of the following Formula:

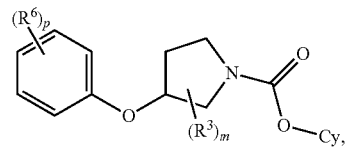

wherein:

$R^6$ is halogen, cyano, $(C_1-C_3)$alkyl, cyclo$(C_3-C_6)$alkyl, halo$(C_1-C_3)$alkyl, hydroxy$(C_1-C_3)$alkyl, $OR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, $(CH_2)_xOR^4$, $(CH_2)_xO(CH_2)_xCO_2R^4$, optionally substituted aryl, optionally substituted heteroaryl, optionally substituted heterocyclyl or optionally substituted cycloalkyl, wherein the aryl, heteroaryl, heterocyclyl and cycloalkyl are further optionally substituted with one to three groups represented by $R^7$; and p is 0, 1, 2 or 3;

or a pharmaceutically acceptable salt thereof.

9. The compound of claim 6, wherein the compound is of the following Formula:

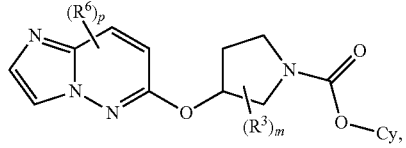

or a pharmaceutically acceptable salt thereof.

10. The compound of claim 6, wherein $R^3$ is $(C_1-C_8)$alkyl or aryl$(C_0-C_3)$alkyl, each optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$, wherein the alkyl portion of aryl$(C_0-C_3)$alkyl is further optionally substituted with oxo;

$R^4$ is independently hydrogen or $(C_1-C_3)$ alkyl; and $R^6$ is halogen, cyano, $(C_1-C_3)$alkyl, cyclo$(C_3-C_6)$alkyl, halo$(C_1-C_3)$alkyl, hydroxy$(C_1-C_3)$alkyl, oxo, $OR^4$, $(CH_2)_xN(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$.

11. The compound of claim 2, wherein the compound is of a formula selected from:

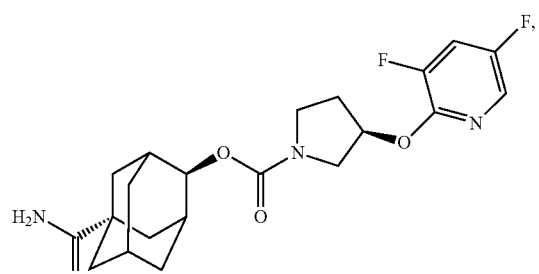

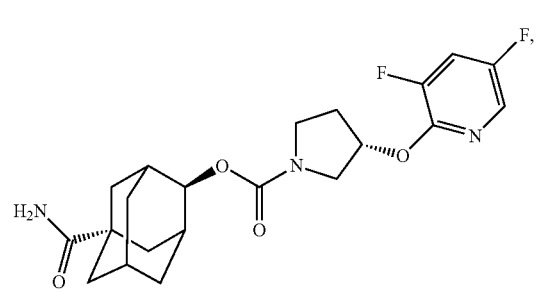

-continued

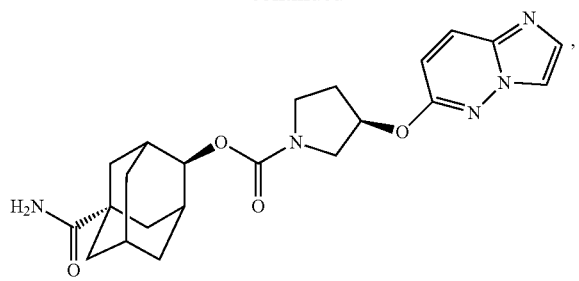

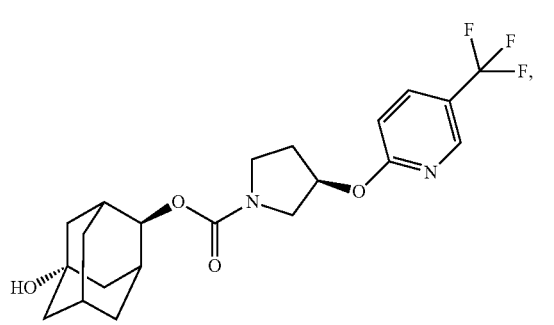

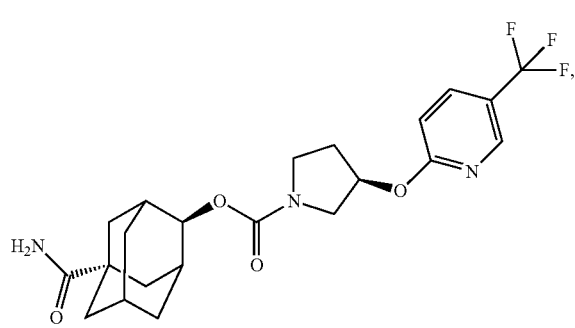

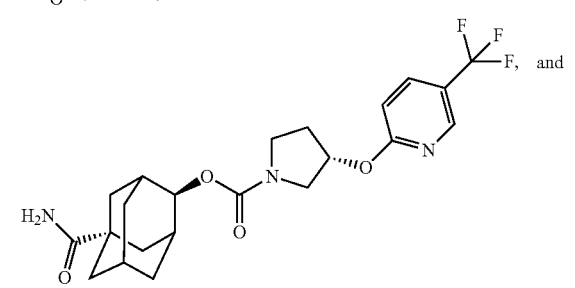

, and

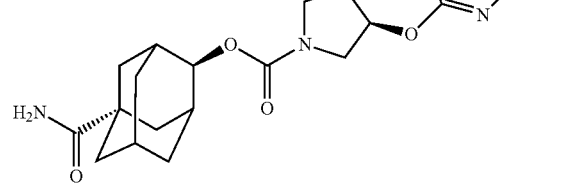

or a pharmaceutically acceptable salt thereof.

12. The compound of claim 1, wherein the compound is of the following Formula,

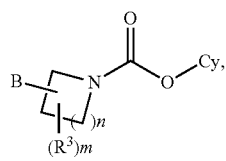

or a pharmaceutically acceptable salt thereof.

13. The compound of claim 12, wherein the compound is of the following Formula:

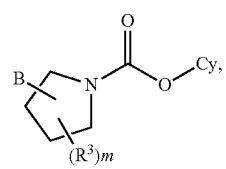

or a pharmaceutically acceptable salt thereof.

14. The compound of claim 13, wherein the compound is of the following Formula:

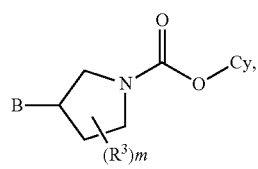

or a pharmaceutically acceptable salt thereof.

15. The compound of claim 14, wherein
$R^3$ is $(C_1-C_8)$alkyl or aryl$(C_0-C_3)$alkyl, each optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CON(R^4)_2$, $CH_2CON(R^4)_2$, $SO_2N(R^4)_2$, $SO_2R^4$, $NR^4COR^4$, $NR^4SO_2R^4$, $NR^4CON(R^4)_2$ and $OC(=O)N(R^4)_2$, wherein the alkyl portion of aryl$(C_0-C_3)$alkyl is further optionally substituted with oxo; and
$R^4$ is independently hydrogen or $(C_1-C_3)$ alkyl.

16. The compound of claim 12, wherein B is heteroaryl, optionally substituted with 1-4 groups represented by $R^6$; wherein each $R^6$ is independently selected from halogen, cyano, $(C_1-C_3)$alkyl, cyclo$(C_3-C_6)$alkyl, halo$(C_1-C_3)$alkyl, hydroxy$(C_1-C_3)$alkyl, oxo, $OR^4$, halo$(C_1-C_3)$alkoxy, $(CH_2)_x N(R^4)_2$, $(CH_2)_xCON(R^4)_2$, $(CH_2)_xCO_2R^4$, $(CH_2)_xSO_2 N(R^4)_2$, $(CH_2)_xSO_2R^4$, $(CH_2)_xNR^4COR^4$, $(CH_2)_x NR^4CO_2R^4$, $(CH_2)_xNR^4SO_2R^4$, $(CH_2)_xNR^4CON(R^4)_2$, and $(CH_2)_xOC(=O)N(R^4)_2$.

17. The compound of claim 16, wherein the compound is of the following Formula:

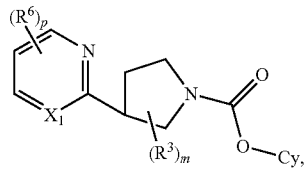

wherein:

$X_1$ is N or $CR^5$;

$R^5$ is hydrogen or $(C_1-C_6)$alkyl;

$R^6$ is halogen, nitro, cyano, $(C_1-C_3)$alkyl, cyclo$(C_3-C_6)$alkyl, halo$(C_1-C_3)$alkyl, hydroxy$(C_1-C_3)$alkyl, $OR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, $(CH_2)_xOR^4$, $(CH_2)_xO(CH_2)_xCO_2R^4$, optionally substituted aryl, optionally substituted heteroaryl, optionally substituted heterocyclyl or optionally substituted cycloalkyl, wherein the aryl, heteroaryl, heterocyclyl and cycloalkyl are further optionally substituted with one to three groups represented by $R^7$; and p is 0, 1, 2 or 3;

or a pharmaceutically acceptable salt thereof.

18. The compound of claim 12, wherein the compound is of the following Formula:

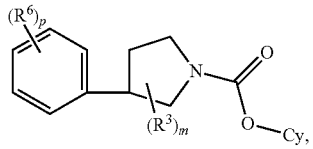

wherein:

$R^6$ is halogen, nitro, cyano, $(C_1-C_3)$alkyl, cyclo$(C_3-C_6)$alkyl, halo$(C_1-C_3)$alkyl, hydroxy$(C_1-C_3)$alkyl, $OR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, $(CH_2)_xOR^4$, $(CH_2)_xO(CH_2)_xCO_2R^4$, optionally substituted aryl, optionally substituted heteroaryl, optionally substituted heterocyclyl or optionally substituted cycloalkyl, wherein the aryl, heteroaryl, heterocyclyl and cycloalkyl are further optionally substituted with one to three groups represented by $R^7$; and p is 0, 1, 2 or 3;

or a pharmaceutically acceptable salt thereof.

19. The compound of claim 16, wherein the compound is of the following Formula:

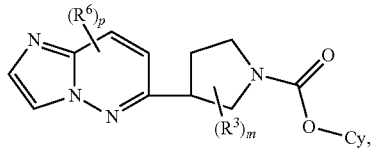

wherein:

$R^6$ is halogen, nitro, cyano, $(C_1-C_3)$alkyl, halo$(C_1-C_3)$alkyl, hydroxy$(C_1-C_3)$alkyl, $OR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)-CON(R^4)_2$, $(CH_2)-CO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, $(CH_2)_xOR^4$, $(CH_2)_xO(CH_2)_xCO_2R^4$, optionally substituted aryl, optionally substituted heteroaryl, optionally substituted heterocyclyl or optionally substituted cycloalkyl, wherein the aryl, heteroaryl, heterocyclyl and cycloalkyl are further optionally substituted with one to three groups represented by $R^7$; and p is 0, 1, 2 or 3;

or a pharmaceutically acceptable salt thereof.

20. The compound of claim 16, wherein $R^3$ is $(C_1-C_8)$alkyl or aryl$(C_0-C_3)$alkyl, each optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$, wherein the alkyl portion of aryl$(C_0-C_3)$alkyl is further optionally substituted with oxo;

$R^4$ is independently hydrogen or $(C_1-C_3)$ alkyl; and $R^6$ is halogen, cyano, $(C_1-C_3)$alkyl, halo$(C_1-C_3)$alkyl, hydroxy$(C_1-C_3)$alkyl, oxo, $OR^4$, $(CH_2)_xN(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ or $OC(=O)N(R^4)_2$.

21. The compound of claim 12, wherein the compound is of a formula selected from:

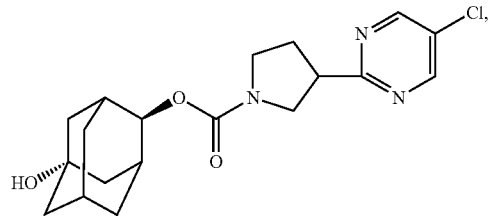

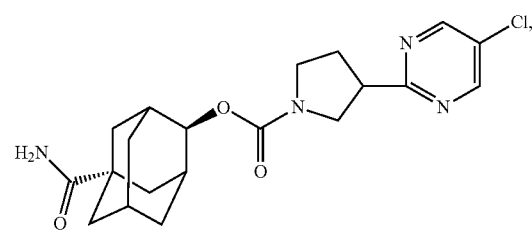

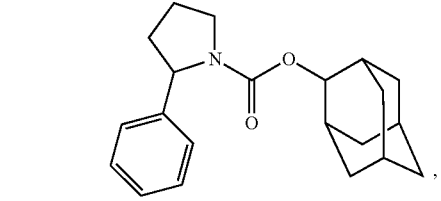

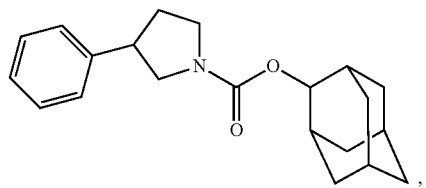

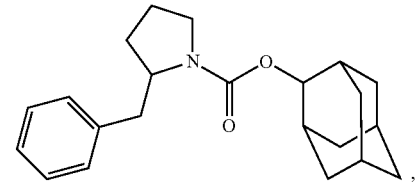

115
-continued
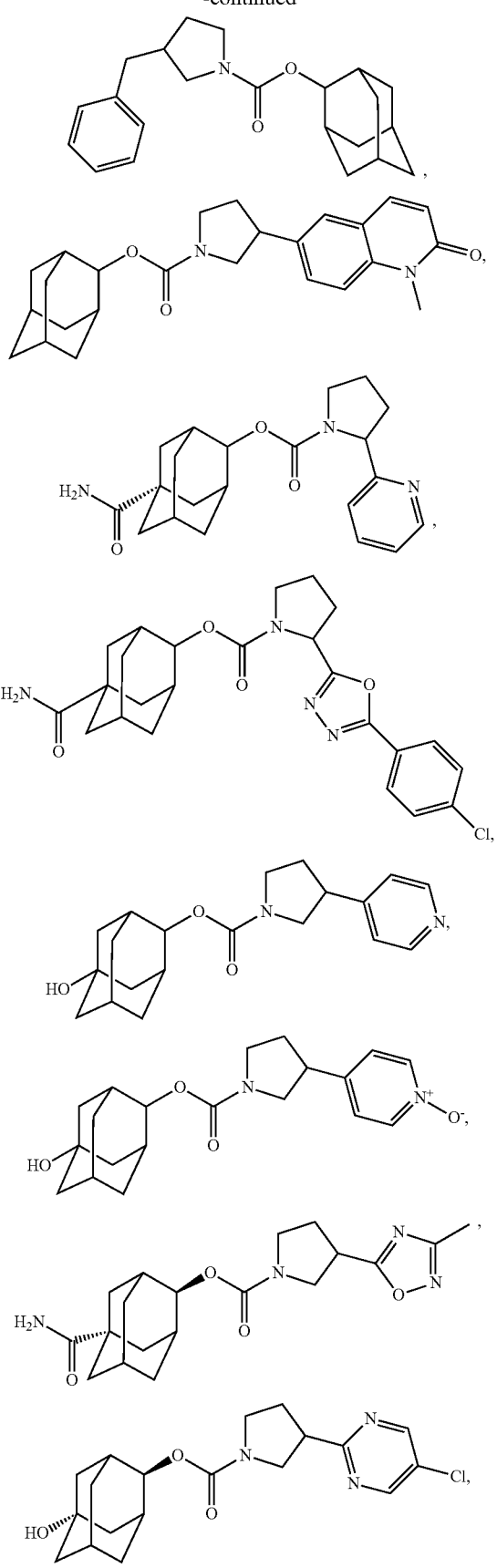
116
-continued
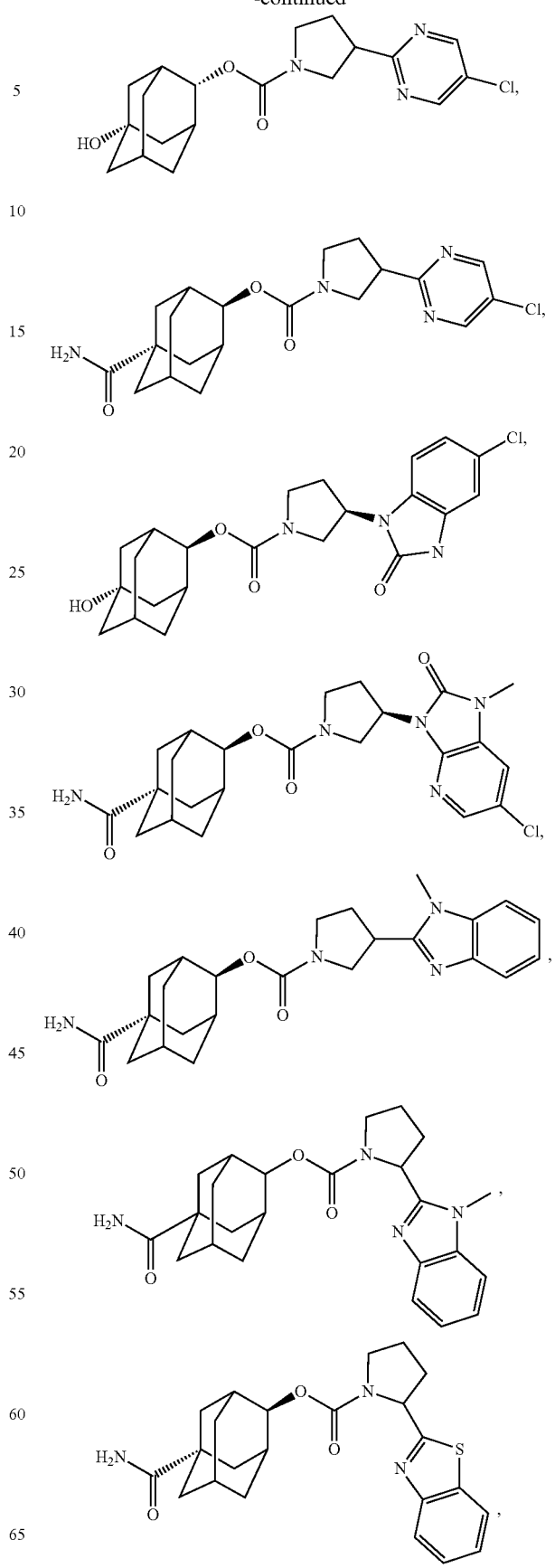

-continued

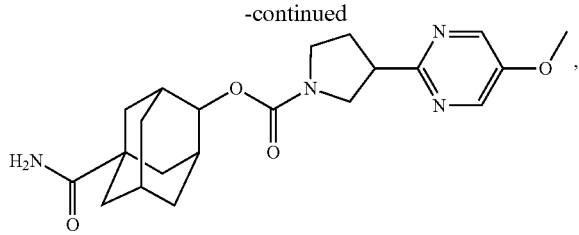

and

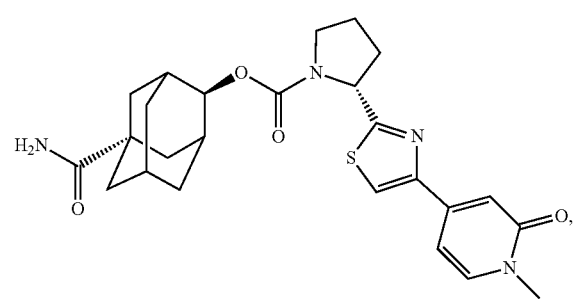

or a pharmaceutically acceptable salt thereof.

22. A pharmaceutical composition comprising: i) a pharmaceutically acceptable carrier or diluent; and ii) a compound of claim 1 or a pharmaceutically acceptable salt thereof.

23. The compound of claim 1, wherein the compound is of the following Formula:

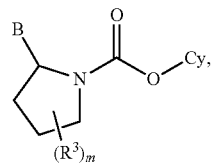

or a pharmaceutically acceptable salt thereof.

24. The compound of claim 23, wherein $R^3$ is $(C_1-C_8)$alkyl or aryl$(C_0-C_3)$alkyl, wherein each group represented by $R^3$ is optionally substituted by 1-4 groups independently selected from halogen, cyano, $(C_1-C_3)$ alkyl, halo$(C_1-C_3)$alkyl, hydroxy$(C_1-C_3)$alkyl, $OR^4$, $N(R^4)_2$, $CON(R^4)_2$, $CH_2CON(R^4)_2$, $SO_2N(R^4)_2$, $SO_2R^4$, $NR^4COR^4$, $NR^4SO_2R^4$, $NR^4CON(R^4)_2$ and $OC(=O)N(R^4)_2$, wherein the alkyl portion of aryl$(C_0-C_3)$alkyl in the group represented by $R^3$ is further optionally substituted with oxo; and $R^4$ is independently hydrogen or $(C_1-C_3)$ alkyl.

25. The compound of claim 24, wherein B is thiazolyl or pyrimidinyl, each of which is optionally substituted with 1-4 groups represented by $R^6$.

26. The compound of claim 1, wherein the compound is of a formula selected from:

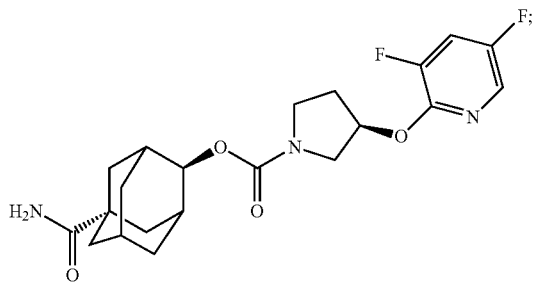

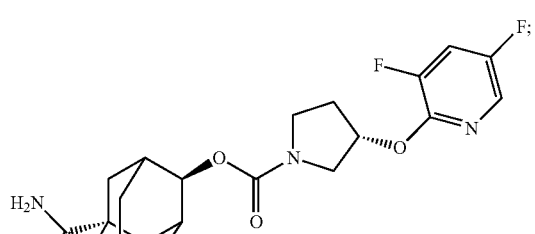

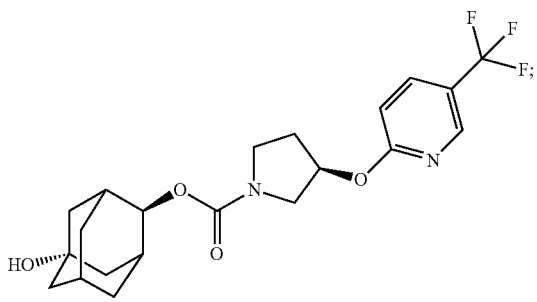

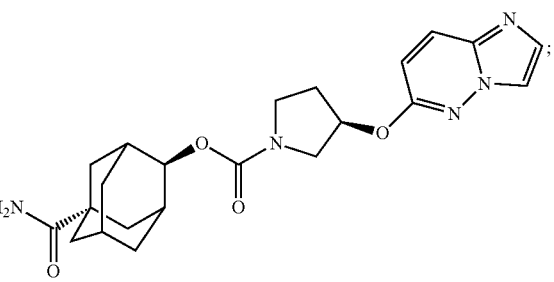

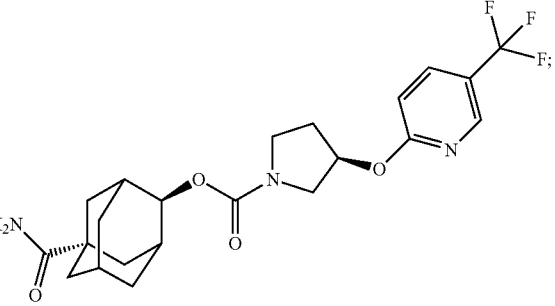

119
-continued
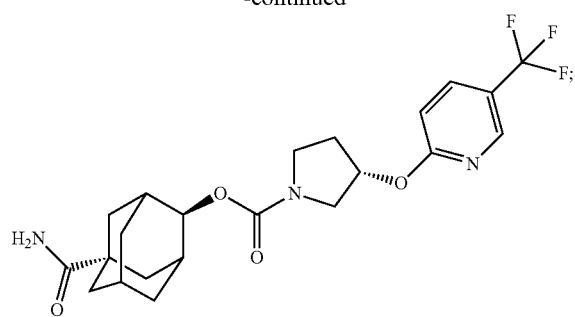
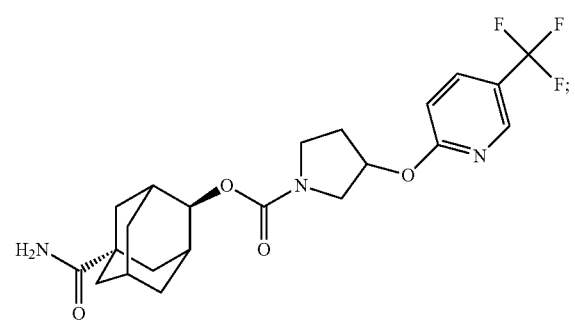
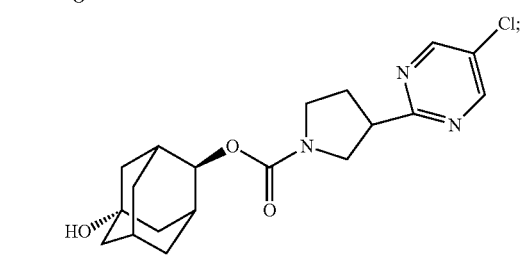
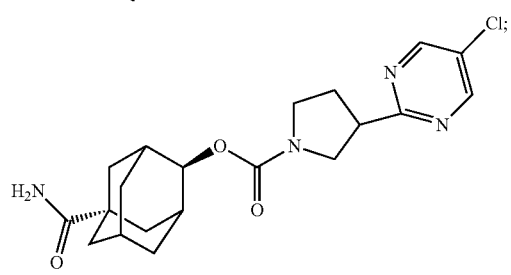
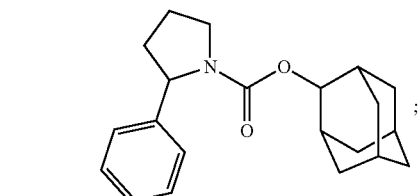
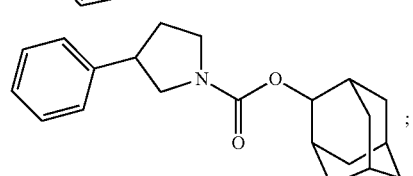
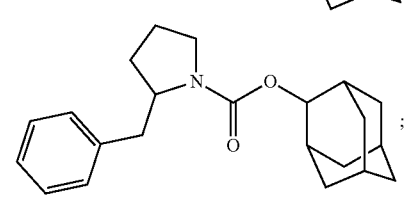
120
-continued
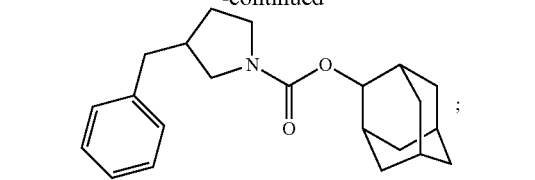
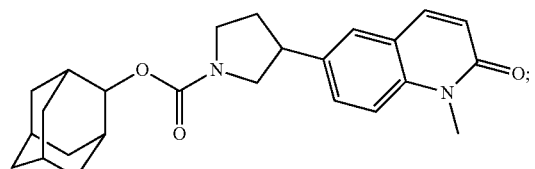
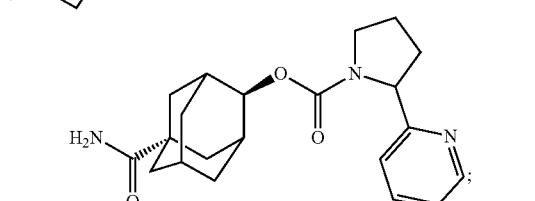
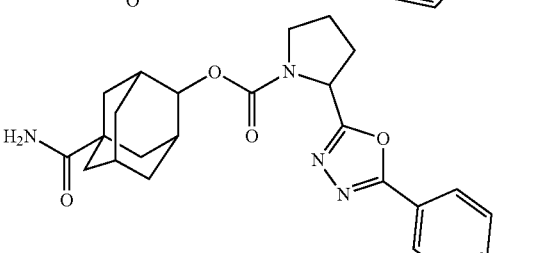
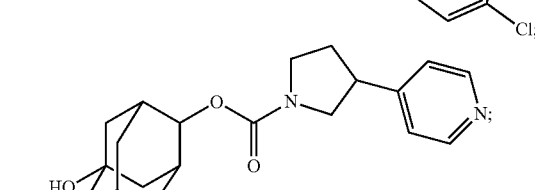
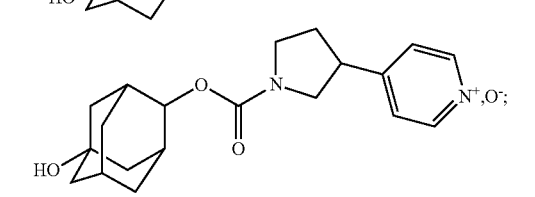
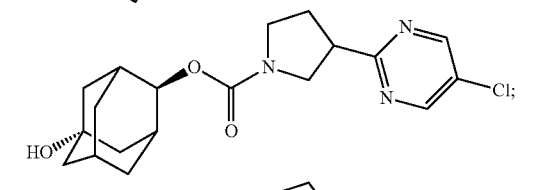
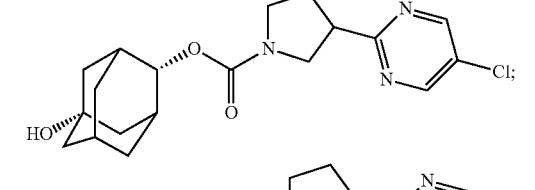
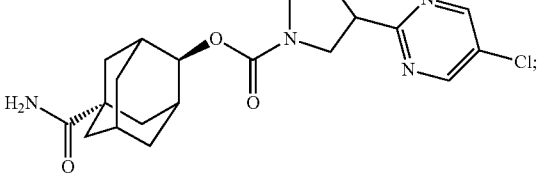

121
-continued
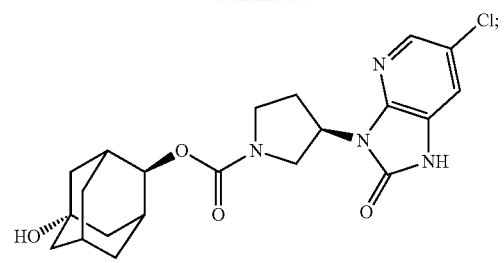
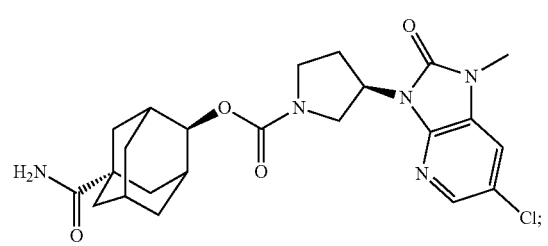
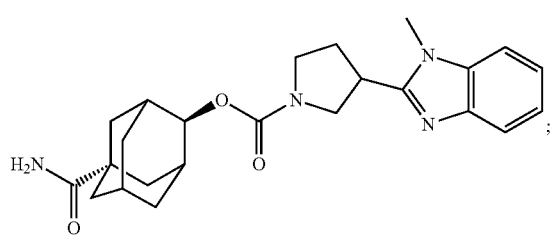
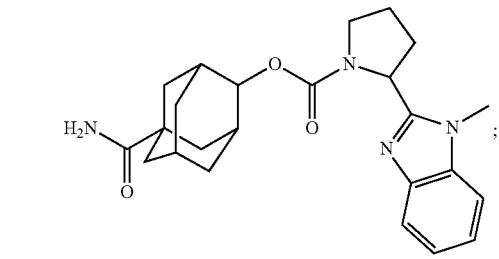
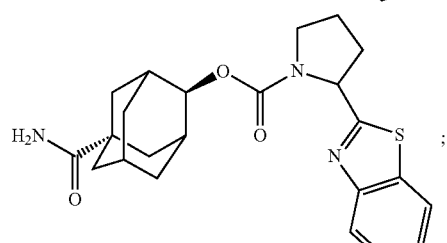
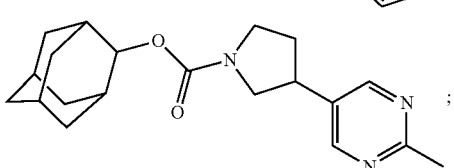
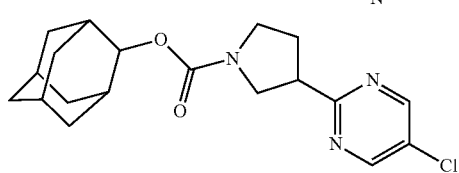
122
-continued
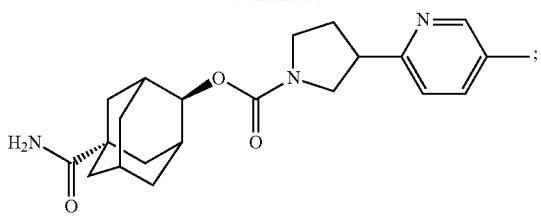
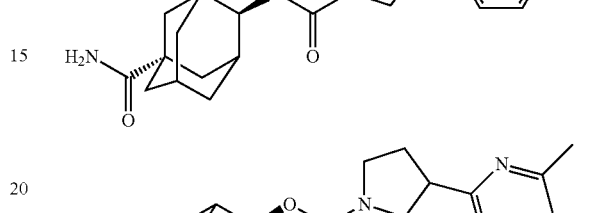
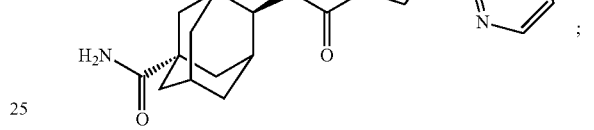
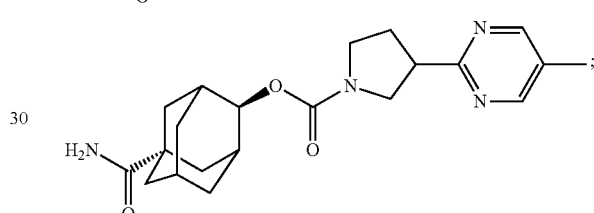
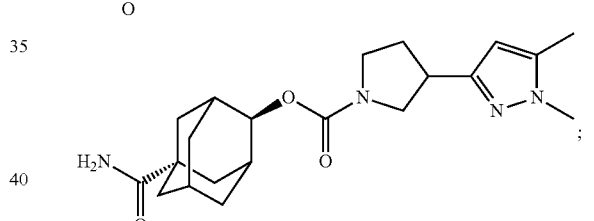
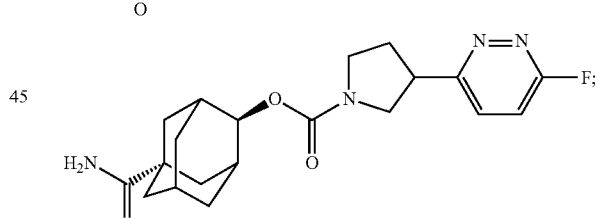
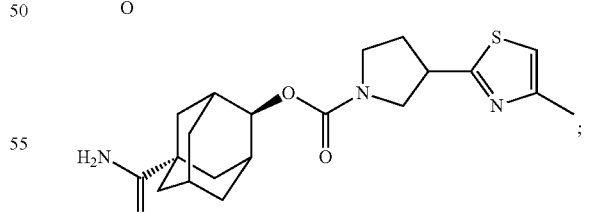
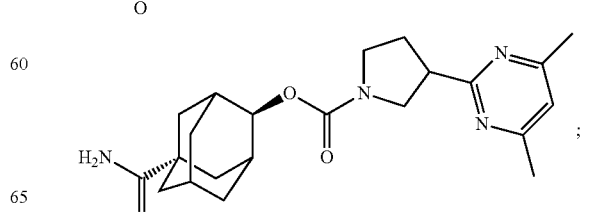

123
-continued
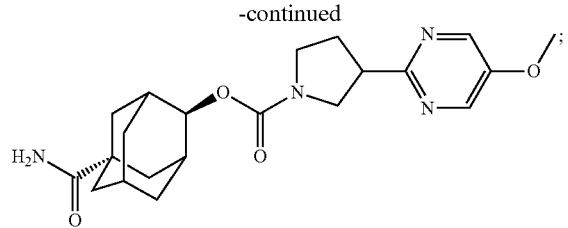
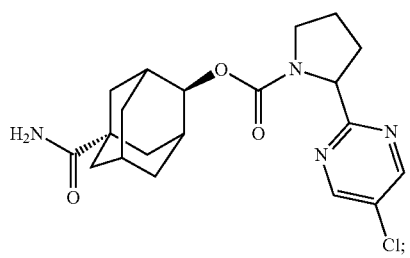
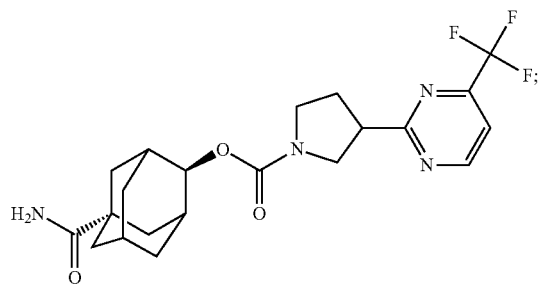
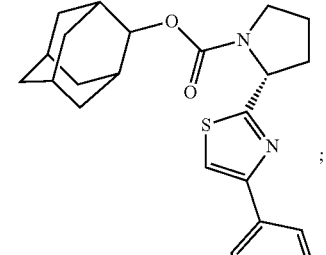
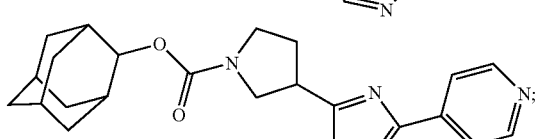
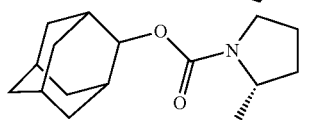
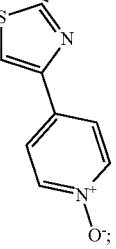
124
-continued
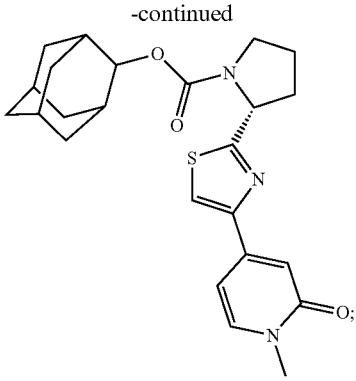
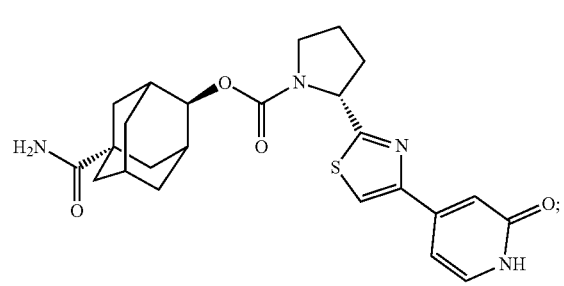
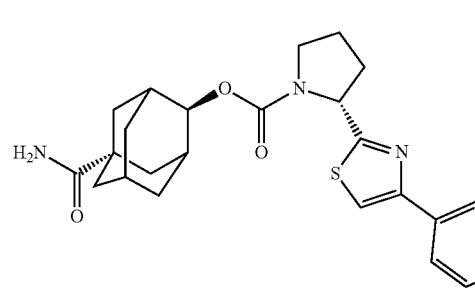
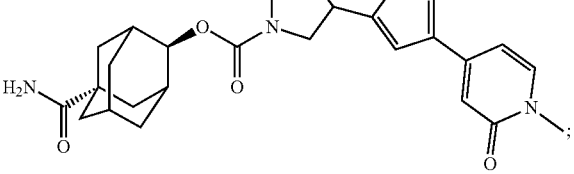
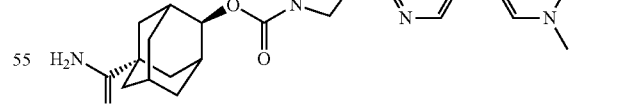
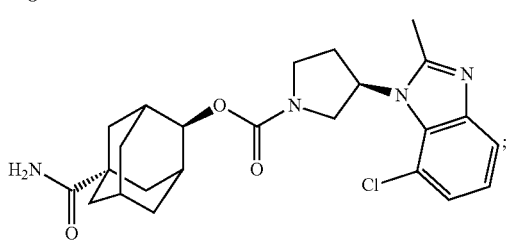

125
-continued
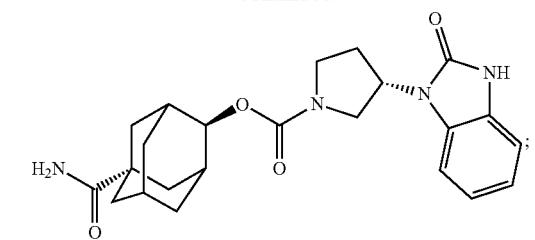
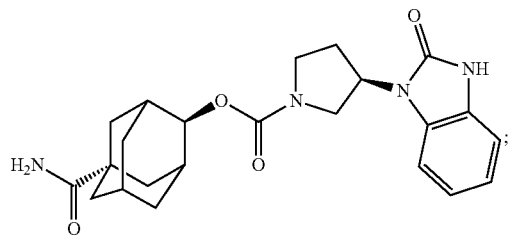
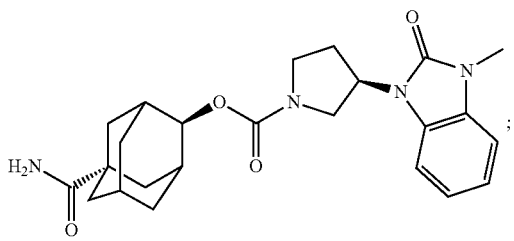
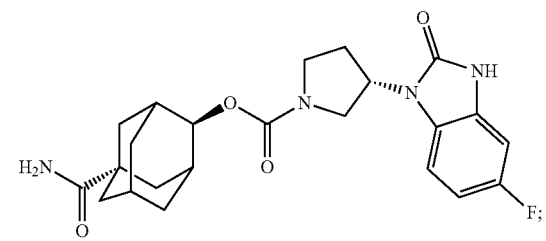
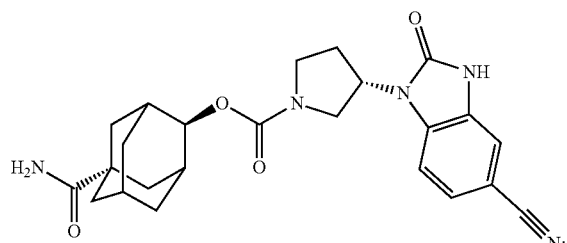
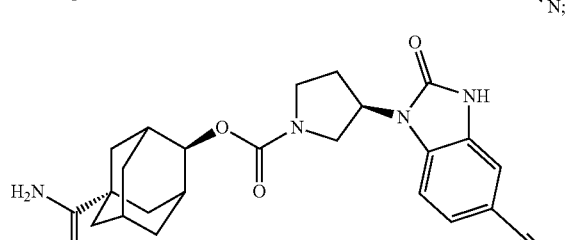
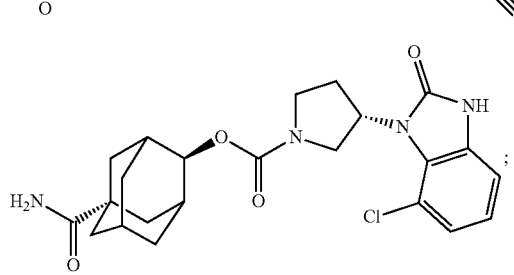
126
-continued
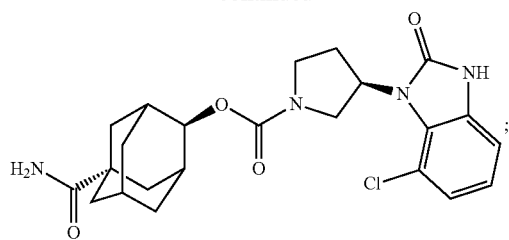
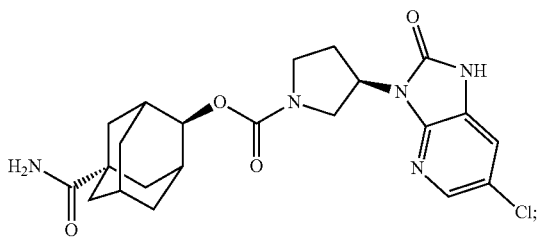
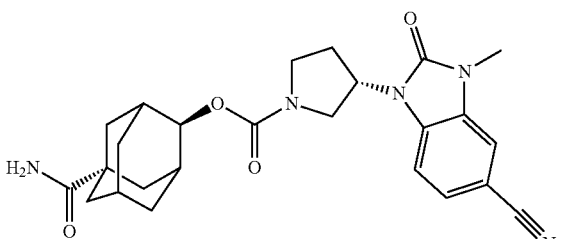
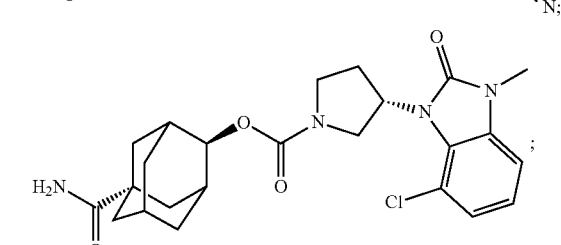
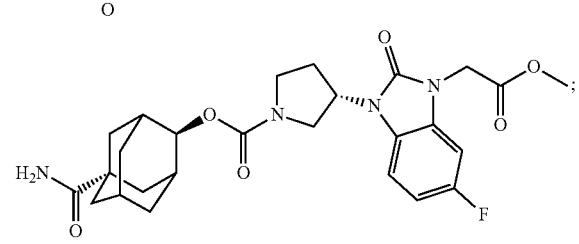
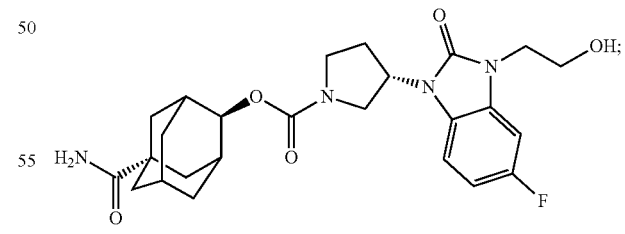
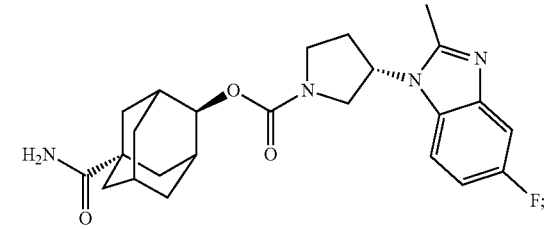

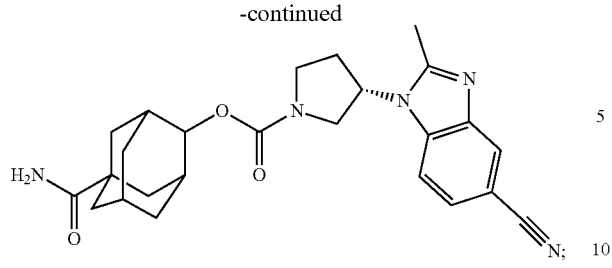

and

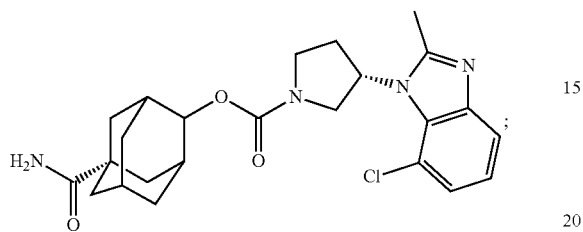

or a pharmaceutically acceptable salt thereof.

27. A method of treating a subject with a disease or disorder selected from diabetes mellitus, obesity, glucose intolerance, hyperglycemia, hypertension, insulin resistance, dyslipidemia, atherosclerosis, Cushing's syndrome, visceral fat obesity associated with glucocorticoid therapy, Alzheimer's disease, cognitive decline, or metabolic syndrome, comprising the step of administering to the subject an effective amount of a compound of claim 1, or a pharmaceutically acceptable salt thereof.

* * * * *